(12) United States Patent
Burnett et al.

(10) Patent No.: US 7,511,146 B2
(45) Date of Patent: Mar. 31, 2009

(54) 2-SUBSTITUTED BENZIMIDAZOLE PIPERIDINES ANALOGS AS SELECTIVE MELANIN CONCENTRATING HORMONE RECEPTOR ANTAGONISTS FOR THE TREATMENT OF OBESITY AND RELATED DISORDERS

(75) Inventors: Duane A. Burnett, Bernardsville, NJ (US); Wen-Lian Wu, Edison, NJ (US); Thavalakulamgara K. Sasikumar, Edison, NJ (US); William J. Greenlee, Teaneck, NJ (US); Mary Ann Caplen, Sayreville, NJ (US); Tao Guo, Dayton, NJ (US); Rachael Catherine Hunter, Princeton, NJ (US)

(73) Assignee: Schering Corporation, Kenilworth, NJ (US)

( * ) Notice: Subject to any disclaimer, the term of this patent is extended or adjusted under 35 U.S.C. 154(b) by 504 days.

(21) Appl. No.: 10/926,557

(22) Filed: Aug. 26, 2004

(65) Prior Publication Data
US 2005/0054628 A1 Mar. 10, 2005

Related U.S. Application Data

(60) Provisional application No. 60/498,876, filed on Aug. 29, 2003.

(51) Int. Cl.
*C07D 211/32* (2006.01)
(52) U.S. Cl. ..................................... 546/199
(58) Field of Classification Search ................... 546/199
See application file for complete search history.

(56) References Cited

U.S. PATENT DOCUMENTS 5,908,830 A 6/1999 Smith et al.

FOREIGN PATENT DOCUMENTS

| WO | WO 02/076947 | 10/2002 |
|----|--------------|---------|
| WO | WO 02/081460 | 10/2002 |
| WO | WO 02/088093 | 11/2002 |
| WO | WO 03/088908 | 10/2003 |

OTHER PUBLICATIONS

CN 109:54704, Saksena et al , Jol. Ind. Chem. Soc.64(7) pp. 446-448 (1987) Chem Abs. Best availble.*
McGraw—Hill Dictionary of Chemical Terms(1990), pp. 282.*
Concise Encyclopedia Chemistry (1993), pp. 490.*
Hawlev's Condensed Chemical Dictionary (1993), pp. 594.*
Shimada et al., "Mice Lacking Melanin-Concentrating Hormone are Hypophagic and Lean", Nature, (Dec. 17, 1998), pp. 670-674, vol. 396.
Borowsky et al., "Antidepressant, Anxiolytic and Anorectic Effects of a Melanin-Concentrating Hormone-1 Receptor Antagonist", Nature Medicine, (Aug. 1, 2002), pp. 825-830, vol. 8.
International Search Report for PCT/US2004/027734—5pgs.

* cited by examiner

*Primary Examiner*—Janet L. Andres
*Assistant Examiner*—Raymond Covington
(74) *Attorney, Agent, or Firm*—Palaiyur S. Kalyanaraman; William Y. Lee

(57) ABSTRACT

The present invention discloses compounds of formula I

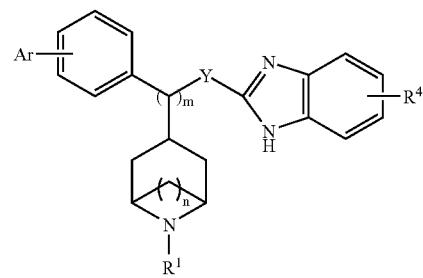

formula I wherein Ar, Y, m, n, $R^1$ and $R^4$ are herein defined, said compounds being novel antagonists for melanin-concentrating hormone (MCH), as well as methods for preparing such compounds. In another embodiment, the invention discloses pharmaceutical compositions comprising such MCH antagonists as well as methods of using them to treat obesity, metabolic disorders, eating disorders such as hyperphagia, and diabetes.

13 Claims, No Drawings

2-SUBSTITUTED BENZIMIDAZOLE PIPERIDINES ANALOGS AS SELECTIVE MELANIN CONCENTRATING HORMONE RECEPTOR ANTAGONISTS FOR THE TREATMENT OF OBESITY AND RELATED DISORDERS

CROSS REFERENCE TO RELATED APPLICATIONS

This application claims the benefit of U.S. Provisional Application No. 60/498,876 filed on Aug. 29, 2003.

FIELD OF THE INVENTION

This invention relates to antagonists for melanin-concentrating hormone (MCH) and their use in the treatment of metabolic and eating disorders, novel compounds having MCH receptor modulatory activity, pharmaceutical compositions containing one or more such modulators, methods of preparing such modulators and methods of using such modulators to treat obesity, diabetes and related disorders.

BACKGROUND OF THE INVENTION

MCH, a cyclic peptide, was first identified over a decade ago in teleost fish where it appears to regulate color change. More recently, MCH has been the subject of investigation for its possible role as a regulator of eating behavior in mammals. As reported by Shimada et al., Nature, Vol. 396 (17 Dec. 1998), pp. 670-673, MCH-deficient mice have reduced body weight and leanness due to hypophagia (reduced feeding). In view of their findings, it was suggested that antagonists of MCH may be effective for the treatment of obesity. U.S. Pat. No. 5,908,830 discloses a combination therapy for the treatment of diabetes or obesity involving the administration of a metabolic rate increasing agent and a feeding behavior modifying agent, an example of the latter being an MCH antagonist. Further, MCH receptor antagonists may also be useful in the treatment of depression and/or anxiety. Borowksy et al., Nature Medicine, 8, pp. 825-830 (01 Aug. 2002).

SUMMARY OF THE INVENTION

In one embodiment, this invention provides novel benzimidazole compounds which can have MCH antagonist activity. These compounds are represented by structural formula I:

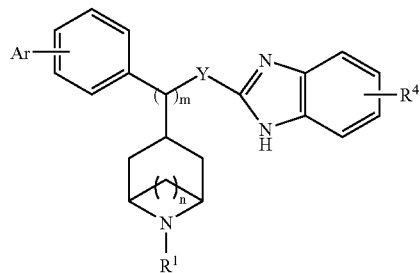

formula I or a pharmaceutically acceptable salt or solvate thereof, wherein

Y is a bond, $-(CR^2R^3)_p NR^8(CH_2)_q-$, $-(CR^2R^3)_t$ $(CHR^{12})-$, $-(CHR^{12})_t(CR^2R^3)-$, $-CHR^{12}CH_2N-$, $-CHR^{12}CH_2S-$, $-CHR^{12}CH_2O-$, $-C(O)(CR^2R^3)_p$ $NR^8-$, $-(CH_2)_pO(CH_2)_q-$, $-(CH_2)_pS(CH_2)_q-$, $-(CR^2R^3)_t-$, $-C(O)(CH_2)_rO-$ or $-C(O)(CH_2)_rS-$;

m is 0 or 1;
n is 0, 2 or 3;
p is 0 to 4;
q is 0 to 4;
r is 1 to 3;
t is 1 to 6;

Ar is aryl, heteroaryl, $R^6$-substituted aryl or $R^6$-substituted heteroaryl;

$R^1$ is hydrogen, alkyl, cycloalkyl, cycloalkylalkyl-, aralkyl, heterocyclyl, heterocyclylalkyl, hydroxyalkyl, heteroaralkyl, $-C(O)R^5$, $-C(O)OR^5$, $-C(O)NR^8R^9$, $-S(O_2)R^5$, $-S(O_2)NR^8R^9$, aryl, heteroaryl, $-CF_3$, $R^{10}$-substituted aralkyl, $R^{10}$-substituted heterocyclyl, $R^{10}$-substituted aryl, $R^{10}$-substituted heteroaryl, $R^{10}$-substituted heterocyclylalkyl, $R^{10}$-substituted heteroaralkyl, $R^{10}$-substituted alkyl, $R^{10}$-substituted cycloalkyl- or $R^{10}$-substituted cycloalkylalkyl-;

$R^2$ and $R^3$ can be the same or different, each being independently hydrogen or alkyl; or $R^2$ and $R^3$ can be joined together and with the carbon to which they are attached form a 3 to 7-membered ring;

$R^4$ is 1 to 4 substituents, each $R^4$ is independently selected from the group consisting of hydrogen, $-OH$, alkoxy, $-OCF_3$, $-CN$, alkyl, halogen, $-NR^8C(O)R^7$, $-C(O)NR^8R^9$, $-NR^8S(O_2)R^7$, $-S(O_2)NR^8R^9$, $-S(O_2)R^7$, $-C(O)R^7$, $-C(O)OR^8$, $-CF_3$, -(alkylene)$NR^8R^9$, -(alkylene)$NR^8C(O)R^7$, CHO, $-C=NOR^8$ or two adjacent $R^4$ groups can be joined together to form a methylene dioxy or ethylene dioxy group;

$R^5$ is alkyl, aryl, aralkyl, heteroaryl, heteroaralkyl, cycloalkyl, heterocyclyl, heterocyclylalkyl, $R^{11}$-substituted heteroaralkyl, $R^{11}$-substituted cycloalkyl, $R^{11}$-substituted heterocyclyl, $R^{11}$-substituted heterocyclylalkyl, $R^{11}$-substituted aryl or $R^{11}$-substituted heteroaryl;

$R^6$ is 1 to 5 substituents, each $R^6$ is independently selected from the group consisting of hydrogen, $-OH$, alkoxy, $-OCF_3$, $-CN$, alkyl, halogen, $-NR^8R^9$, $-NR^8C(O)R^7$, $-C(O)NR^8R^9$, $-NR^8S(O_2)R^7$, $-S(O_2)NR^8R^9$, $-S(O_2)$ $R^7$, $-C(O)R^7$, $-C(O)OR^8$, $-CF_3$, -(alkylene) $NR^8R^9$, -(alkylene)C(O)$NR^8R^9$, -(alkylene)$NR^8$ C(O)$R^7$, -(alkylene)$NR^8S(O_2)R^7$, -(alkylene)$NR^8C(O)$ $NR^8R^9$, -(alkylene)$NR^8C(O)OR^7$, CHO, $-C=NOR^8$ and

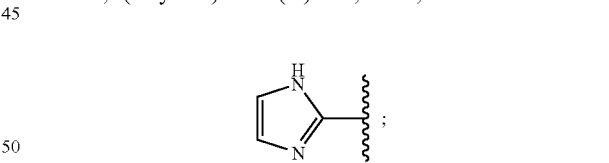

$R^7$ is alkyl, aryl, aralkyl, heteroaryl, heteroaralkyl, $R^{11}$-substituted aryl or $R^{11}$-substituted heteroaryl;

$R^8$ is hydrogen or alkyl;

$R^9$ is hydrogen, alkyl, aryl, aralkyl, cycloalkyl, heteroaralkyl or heteroaryl;

$R^{10}$ is 1 to 5 substituents, each $R^{10}$ is independently selected from the group consisting of $-OH$, alkoxy, $-C(O)$ $NR^8R^9$, $-NR^8R^9$, $-NR^8S(O_2)R^5$, $-NR^8C(O)NR^8R^9$, $-NR^8C(O)R^5$, $-NR^8C(O)OR^5$ and $-C(O)OR^9$;

$R^{11}$ is 1 to 5 substituents, each $R^{11}$ being independently selected from the group consisting of hydrogen, $-OH$, alkoxy, $-OCF_3$, $-CN$, alkyl, halogen or $-CF_3$; and $R^{12}$ is hydroxy or alkoxy.

This invention is also directed to pharmaceutical compositions for the treatment of metabolic disorders such as obesity, those disorders associated with obesity and eating disorders such as hyperphagia. In one aspect, this invention is directed to the method of treatment of metabolic disorders such as obesity, and eating disorders such as hyperphagia. Another embodiment includes a method of treating an eating disorder which comprises administering to a mammal in need of such treatment an amount of a first compound, said first compound being a compound of formula I; and a second compound, said second compound being an antiobesity and/or anorectic agent wherein the amounts of the first and second compounds result in the therapeutic desired effect. In another aspect, this invention is also directed to pharmaceutical compositions for the treatment of obesity which comprise an obesity treating amount of at least one compound of formula I, or a pharmaceutically acceptable salt or solvate of said compound and a pharmaceutically acceptable carrier.

DETAILED DESCRIPTION

The present invention relates to compounds that are represented by structural formula I, or a pharmaceutically acceptable salt or solvate thereof, wherein the various moieties are as described above.

When m is 0, the present invention includes those compounds of formula I wherein, Y and

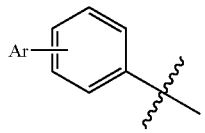

are linked to the adjacent ring to form a compound of the following formula,

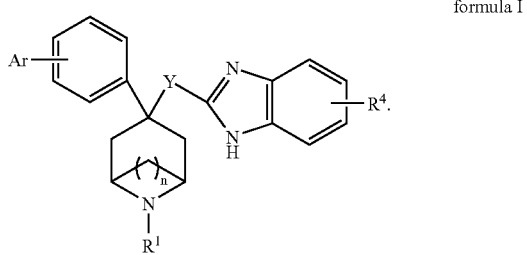

formula I

Further compounds within the scope of the present invention include those compounds of formula I when n is 0, there is no connecting bond between the two carbons adjacent to the nitrogen of the piperidyl ring.

One aspect of the invention are compounds of formula I wherein Y is —$(CR^2R^3)_pNR^8(CH_2)_q$—, p is 1; q is 0; $R^2$ and $R^3$ are hydrogen or alkyl; and $R^8$ is hydrogen or alkyl.

An additional aspect of the invention are compounds of formula I wherein Y is —$(CR^2R^3)_pNR^8(CH_2)_q$—, p is 0; q is 1; $R^2$ and $R^3$ are hydrogen or alkyl; and $R^8$ is hydrogen or alkyl.

Additional preferred aspects of the invention include those compounds of formula I wherein Y is —$(CH_2)_pO(CH_2)_q$—; p is 0; and q is 1. Alternative aspects of the invention also include those compounds wherein Y is —$(CH_2)_pO(CH_2)_q$—; p is 1; and q is 0; or wherein Y is —$(CR^2R^3)_t$—; t is 2; and $R^2$ and $R^3$ are hydrogen or alkyl.

Additional preferred aspects of the invention include those compounds of formula I wherein $R^1$ is hydrogen, alkyl, aralkyl, cycloalkyl, cycloalkylalkyl-, $R^{10}$-substituted alkyl, hydroxyalkyl, —$S(O_2)R^5$, —$C(O)R^5$, —$C(O)NR^8R^9$ or —$C(O)OR^5$.

Another aspect of the invention include those compounds of formula I wherein Ar is $R^6$-substituted aryl; and $R^6$ is 1 to 5 substituents and each $R^6$ is independently selected from the group consisting of halogen, —$CF_3$, —$OCF_3$, —CN, —CHO, —$S(O_2)R^5$, —$C(O)R^5$, —$C(O)NR^8R^9$, -(alkylene)$C(O)NR^8R^9$, -(alkylene)$NR^8R^9$, -(alkylene)$NR^8C(O)R^5$, -(alkylene)$NR^8S(O_2)R^5$ and

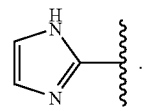

Another aspect of the invention include those compounds of formula I wherein $R^6$ is 1 substituent, wherein said $R^6$ is independently selected from the group consisting of halogen, —CN, -(alkylene)$C(O)NR^8R^9$, -(alkylene)$NR^8R^9$ and -(alkylene)$NR^8C(O)R^5$.

Another aspect of the invention include those compounds of formula I wherein Ar is $R^6$-substituted phenyl and $R^6$ is at the meta or para position of Ar, relative to the position where Ar is attached to the parent moiety.

Another aspect of the invention include those compounds of formula I wherein $R^6$ is at the meta position of Ar, relative to the position where Ar is attached to the parent moiety; preferably $R^6$ is —CN.

Another aspect of the invention include those compounds of formula I wherein $R^4$ is two substituents and each $R^4$ is independently selected from the group consisting of halogen, —CN and —$CF_3$.

Another aspect of the invention include those compounds of formula I wherein $R^4$ is selected from the group consisting of Cl, F and —$CF_3$.

Another aspect of the invention include those compounds of formula I wherein $R^1$ is hydrogen, Boc, methyl, ethyl, hydroxyethyl, hydroxypentyl, cyclobutyl, cyclopentyl,

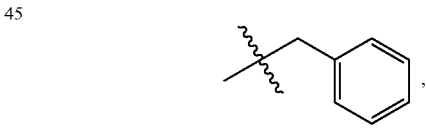

—$S(O_2)CH_3$, —$C(O)CH_3$, —$C(O)CH_2CH_3$, $C(O)NHCH_2CH_3$, isopropyl or cyclopropylmethyl.

Still additional preferred embodiments of formula I include compounds selected from the group consisting of compounds of Examples 8A, 8B, 8C, 8D, 11A, 11B, 11C, 15A, 15B, 16A, 16B, 17A, 17B, 28A, 28B, 33, 34D, 34A, 34B, 34C, 39, 44, 48, 53, 54, 56, 57, 58, 63, 64, 67A, 67B, 75A, 75B and 75C herein.

Other embodiments of the claimed invention include those methods of treatment with the compounds of formula I wherein the eating disorder is hyperphagia and wherein the metabolic disorder is obesity.

Another embodiment is a method of treating a disorder associated with obesity comprising administering to a mammal in need of such treatment a therapeutically effective amount of at least one compound of formula I, or a pharmaceutically acceptable salt or solvate of said compound. Specific examples of disorders associated with obesity include but are not limited to type II diabetes, insulin resistance, hyperlipidemia or hypertension.

Another embodiment includes a method of treating an eating disorder which comprises administering to a mammal in need of such treatment an amount of a first compound, said first compound being a compound of formula I or a pharmaceutically acceptable salt or solvate of said compound; and a second compound, said second compound being an anti-obesity and/or anorectic agent selected from the group consisting of a $\beta_3$ agonist, a thryomimetic agent, an anorectic agent and an NPY antagonist;

wherein the amounts of the first and second compounds result in the desired therapeutic effect (the treatment of obesity, obesity related disorders, metabolic and eating disorders).

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", "cycloalkyl" and so forth.

As used above, and throughout the specification, the following terms, unless otherwise indicated, shall be understood to have the following meanings:

"Alkoxy" means an alkyl-O— group in which the alkyl group is as previously described. Non-limiting examples of suitable alkoxy groups include methoxy, ethoxy, n-propoxy and isopropoxy. The alkyl group is linked to an adjacent moiety through the ether oxygen. Non-limiting examples of suitable alkoxy groups include propoxy, ethoxy and butoxy.

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means an alkyl group having about 1 to about 6 carbon atoms in the chain, which may be straight or branched. The alkyl group can be unsubstituted or substituted with one or more substituents which may be the same or different, each being independently selected from $R^{10}$ groups listed above. Non-limiting examples of suitable alkyl groups include methyl, ethyl, n-propyl, isopropyl, n-butyl, and t-butyl.

"Alkylene" means an alkanediyl group commonly having free valencies on two carbon atoms. Non-limiting examples include methylene, ethylene, propylene and the like.

"Aryl" means an aromatic monocyclic or multicyclic ring system comprising about 6 to about 14 carbon atoms, preferably about 6 to about 10 carbon atoms. Included in the definition of aryl are fused aryls such as indenyl, napthalenyl, anthracenyl and indolinyl. Fused aryls can be attached to the parent moiety either through the saturated or unsaturated portions of the ring. The aryl group can be unsubstituted or substituted on the ring with one or more substituents which may be the same or different, each being independently selected from $R^6$, $R^{10}$ and $R^{11}$ groups listed above. Non-limiting examples of suitable aryl groups include phenyl and naphthyl. The "aryl" group can also be substituted by linking two adjacent carbons on its aromatic ring via a combination of one or more carbon atoms and one or more oxygen atoms such as, for example, methylenedioxy, ethylenedioxy, and the like.

"Aralkyl" means an aryl-alkyl-group in which the aryl and alkyl are as previously described. Preferred aralkyls comprise a lower alkyl group. Non-limiting examples of suitable aralkyl groups include benzyl, 2-phenethyl and a naphthlenylmethyl. The bond to the parent moiety is through the alkyl. The term "substituted aralkyl" means that the aralkyl group may be substituted by one or more substituents which may be the same or different, each substituent being independently selected from $R^{10}$ groups listed above.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted on the ring by replacing an available hydrogen on the ring by one or more substituents which may be the same or different, each being independently selected from $R^{10}$ and $R^{11}$ groups listed above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkylalkyl group in which the cycloalkyl and alkyl groups are as previously described. The cycloalkyl portion of cycloalkylalkyl can be optionally substituted on the ring by replacing an available hydrogen on the ring by one or more substituents which may be the same or different, each being independently selected from $R^{10}$ groups listed above. The bond to the parent moiety is through the alkyl group.

"Halo" means fluoro, chloro, bromo or iodo groups. Preferred are fluoro, chloro or bromo, and more preferred are fluoro and chloro.

"Halogen" means fluorine, chlorine, bromine or iodine. Preferred are fluorine, chlorine or bromine, and more preferred are fluorine and chlorine.

"Haloalkyl" means an alkyl as defined above wherein one or more hydrogen atoms on the alkyl is replaced by a halo group defined above.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted on the ring by replacing an available hydrogen on the ring by one or more substituents which may be the same or different, each being independently selected from $R^6$, $R^{10}$ and $R^{11}$ groups listed above. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrrolyl, triazolyl, and the like.

"Heteroaralkyl" means a heteroaryl-alkyl-group in which the heteroaryl and alkyl are as previously described. Preferred heteroaralkyls contain a lower alkyl group. The heteroaralkyl can be optionally substituted on the ring by replacing an available hydrogen on the ring or hydrogen(s) on any nitrogen(s) suitably by one or more substituents which may be the same or different, each being independently selected from $R^6$ and $R^{10}$ groups listed above. Non-limiting examples of suitable aralkyl groups include pyridylmethyl, 2-(furan-3-yl)ethyl and quinolin-3-ylmethyl. The bond to the parent moiety is through the alkyl.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted on the ring by replacing an available hydrogen on the ring or hydrogen(s) on any nitrogen(s) suitably by one or more substituents which may be the same or different, each being independently selected from $R^{10}$ and $R^{11}$ groups listed above. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, pyranyl, thiophenyl, tetrahydrothiophenyl, morpholinyl and the like.

"Heterocyclylalkyl" means heterocyclyl-alkyl-group in which the heterocyclyl and alkyl are as previously described. The heterocyclyl ring can be optionally substituted on the ring by replacing an available hydrogen on the ring or hydrogen(s) on any nitrogen(s) suitably by one or more substituents which may be the same or different, each being independently selected from $R^{10}$ and $R^{11}$ groups listed above. The nitrogen or sulfur atom of the heterocyclyl can be optionally oxidized to the corresponding N-oxide, S-oxide or S,S-dioxide. Non-limiting examples of suitable heterocyclylalkyl groups include

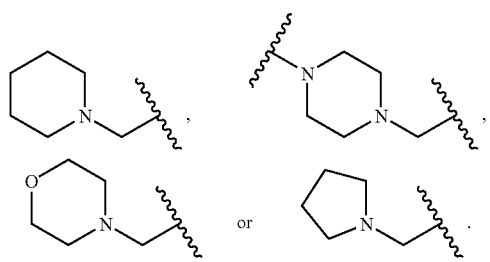

The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Mammal" means humans and other mammalian animals.

"Patient" includes both human and other animals.

It should also be noted that any heteroatom with unsatisfied valences in the text, schemes, examples, structural formulae, and Tables herein is assumed to have the hydrogen atom or atoms to satisfy the valences.

The terms "at least one" compound or "one or more compounds" means one to three compounds, preferably one compound.

When any variable (e.g., aryl, heterocycle, $R^2$, etc.) occurs more than once in any substituent or in Formula I, its definition at each occurrence is independent of its definition at every other occurrence. Also, combinations of substituents and/or variables are permissible only if such combinations result in stable compounds.

The compounds of Formula I can be administered as racemic mixtures or enantiomerically pure compounds within the scope of the present invention.

As used herein, the term "composition" is intended to encompass a product comprising the specified ingredients in the specified amounts, as well as any product which results, directly or indirectly, from combination of the specified ingredients in the specified amounts.

The compounds of formula I can form salts, solvates and prodrugs, which are also within the scope of this invention. Reference to a compound of formula I herein is understood to include reference to salts, solvates and prodrugs thereof, unless otherwise indicated.

Solvates of the compounds of the invention are also contemplated as within the scope of the present invention. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Prodrugs of the compounds of the invention are also contemplated within the scope of this invention. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compound of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulforiates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al,

*Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula I, and salts and solvates thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts and solvates of the compounds), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" and the like, is intended to equally apply to the salt and solvate of enantiomers, stereoisomers, rotamers, tautomers or racemates of the inventive compounds.

Compounds of Formula I can be highly selective, high affinity Melanin Concentrating Hormone (MCH) receptor antagonists useful for the treatment of obesity.

An aspect of this invention is a method of treating a mammal (e.g., human) having a disease or condition mediated by MCH by administering a therapeutically effective amount of at least one compound of Formula I, or a pharmaceutically acceptable salt or solvate of said compound to the mammal.

"Effective amount" or "therapeutically effective amount" is meant to describe an amount of compound of the present invention effective to treat a mammal (e.g., human) having a disease or condition mediated by MCH, and thus producing the desired therapeutic effect (the treatment of obesity, obesity related disorders, metabolic and eating disorders).

A preferred dosage is about 0.001 to 100 mg/kg of body weight/day of the compound of Formula I. An especially preferred dosage is about 0.01 to 30 mg/kg of body weight/day of a compound of Formula I, or a pharmaceutically acceptable salt or solvate of said compound.

Still yet another aspect of this invention is a method of treating obesity comprising administering to a mammal in need of such treatment a therapeutically effective amount of at least one compound of Formula I, or a pharmaceutically acceptable salt or solvate of said compound.

A further aspect of this invention is a method for treating eating and metabolic disorders such as bulimia and anorexia comprising administering to a mammal a therapeutically effective amount of at least one compound of Formula I, or a pharmaceutically acceptable salt or solvate of said compound.

Another aspect of this invention is a method for treating hyperlipidemia comprising administering to a mammal a therapeutically effective amount of at least one compound of Formula I or a pharmaceutically acceptable salt or solvate of said compound.

Another aspect of this invention is a method for treating cellulite and fat accumulation comprising administering to a mammal a therapeutically effective amount of at least one compound of Formula I, or a pharmaceutically acceptable salt or solvate of said compound.

Another aspect of this invention is directed to a method for treating type II diabetes comprising administering to a mammal a therapeutically effective amount of at least one compound of Formula I or a pharmaceutically acceptable salt or solvate of said compound.

In addition to the "direct" effect of the compounds of this invention on the MCH subtype, there are diseases and conditions that can benefit from the weight loss such as, for example, insulin resistance, impaired glucose tolerance, Type II Diabetes, hypertension, hyperlipidemia, cardiovascular disease, gall stones, certain cancers, and sleep apnea.

This invention is also directed to pharmaceutical compositions, which comprise at least one compound of Formula I, or a pharmaceutically acceptable salt or solvate of said compound and at least one pharmaceutically acceptable carrier.

This invention is also directed to pharmaceutical compositions for the treatment of obesity which comprise an obesity treating amount of at least one compound of Formula I, or a pharmaceutically acceptable salt or solvate of said compound and at least one pharmaceutically acceptable carrier.

Still yet other aspects of this invention are combinations of a compound of Formula I, or a pharmaceutically acceptable salt or solvate of said compound and other compounds as described below.

Accordingly, included within the invention is a method for treating obesity comprising administering to a mammal (e.g., a female or male human)

a. an amount of a first compound, said first compound being a compound of Formula I, or a pharmaceutically acceptable salt or solvate of said compound; and b. an amount of a second compound, said second compound being an antiobesity and/or anorectic agent such as a $\beta_3$ agonist, a thyromimetic agent, an anoretic agent, or an NPY antagonist and/or optionally a pharmaceutically carrier, vehicle or diluent, wherein the amounts of the first and second compounds result in a therapeutic effect.

Another aspect of this invention is a kit comprising:

a. an amount of a compound of Formula I, or a pharmaceutically acceptable salt or solvate of said compound and a pharmaceutically acceptable carrier, vehicle or diluent in a first unit dosage form;

b. an amount of an antiobesity and/or anorectic agent such as a $\beta_3$ agonist, a thyromimetic agent, an anoretic agent, or an NPY antagonist and a pharmaceutically acceptable carrier, vehicle or diluent in a second unit dosage form; and c. means for containing said first and second dosage forms wherein the amounts of the first and second compounds result in a therapeutic effect.

Preferred antiobesity and/or anorectic agents (taken singly or in any combination thereof) in the above combination methods, combination compositions and combination kits are:

phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other useful anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Another aspect of this invention is a method of treating diabetes comprising administering to a mammal (e.g., a female or male human)

a. an amount of a first compound, said first compound being a compound of Formula I, or a pharmaceutically acceptable salt or solvate of said compound; and b. an amount of a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide, or chlorpropamide wherein the amounts of the first and second compounds result in a therapeutic effect.

This invention is also directed to a pharmaceutical combination composition comprising: a therapeutically effective amount of a composition comprising a first compound, said first compound being a compound of Formula I, or a pharmaceutically acceptable salt or solvate of said compound;

a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpamide; and optionally a pharmaceutical carrier, vehicle or diluent.

Another aspect of this invention is a kit comprising:

a. an amount of a compound of Formula I, or a pharmaceutically acceptable salt or solvate of said compound and a pharmaceutically acceptable carrier, vehicle or diluent in a first unit dosage form;

b. an amount of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide and a pharmaceutically acceptable carrier, vehicle or diluent in a second unit dosage form; and c. means for containing said first and second dosage forms wherein the amounts of the first and second compounds result in a therapeutic effect.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

Compounds of Formula I can be produced by processes known to those skilled in the art using either solution phase or solid phase synthesis as shown in the following reaction schemes, in the preparations and examples below.

Synthesis

The invention disclosed herein is exemplified by the following preparations and examples which should not be construed to limit the scope of the invention which is defined in the appended claims. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The observed parent ion using electro spray ionization are given.

The following abbreviations are utilized throughout the experimental procedures described below:

SEMCl or SEM-Cl means 2-(trimethylsilyl)ethoxymethyl chloride;
EtONa or NaOEt means sodium ethoxide;
EtOH means ethanol;
MeOH means methanol;
Bu means butyl;
9-BBN means 9-borabicyclo[3.3.1]nonane;
Ac means acetate;
Bn means benzyl;
Me means methyl;
Py means pyridine;
Ph means phenyl;
DEAD means diethylazodicarboxylate;
Ph$_3$P means triphenylphosphine;
CH$_3$CN means acetonitrile;
TBAF means tetrabutylammonium fuoride trihydrate;
TFA means trifluoroacetic acid;
TFAA means trifluoroacetic acid anhydride;
THF means tetrahydrofuran;
Imid means imidazole;
DCM means dichloromethane;
DIBAL means disobutyl aluminum hydride;
DIEA means N,N diisopropylethylamine;
DMA means dimethylacetamide;
DMSO means dimethyl sulfoxide;
DMF means N,N-dimethylformamide;
LAH means lithium aluminum hydride;
PhNTF$_2$ means N-phenyltrifluoromethane sulfonimide;
Boc means Butoxycarbonyl;
(Boc)$_2$O means di-t-butyl carbonate;
NMR means nuclear magnetic resonance spectroscopy;
MS means mass spectrometry;
TLC means Thin layer chromatography;
HPLC means high performance liquid chromatography;
room temperature or rt (ambient) means about 25° C.;
AcOEt or EtOAc means ethyl acetate;
NaBH(OAc$_3$) means sodium triacetoxyborohydride.;
TsOH means toluenesulfonic acid.

Alternative mechanistic pathways and analogous structures within the scope of the invention would be apparent to those skilled in the art.

EXAMPLES

The following examples illustrate the preparation of some of the compounds of the invention and are not to be construed as limiting the scope of the invention disclosed herein.

Experimental Procedures:

Note: These compounds can be prepared via the following schemes:

Aminobenzimidazole Series:

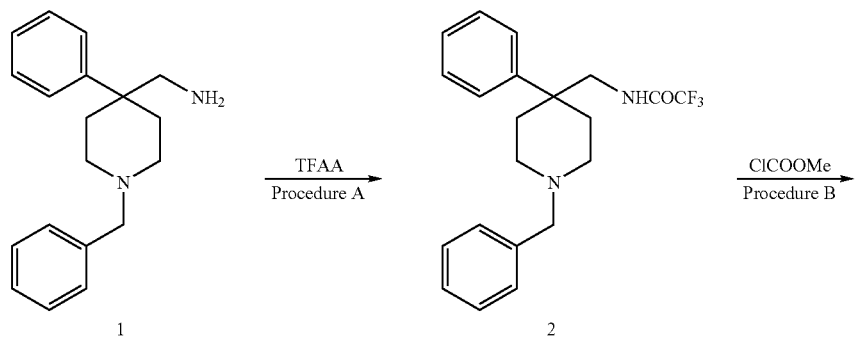

-continued
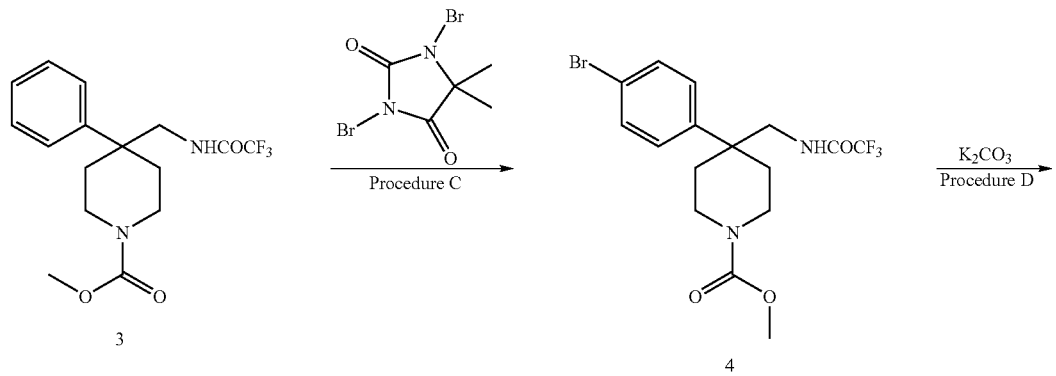
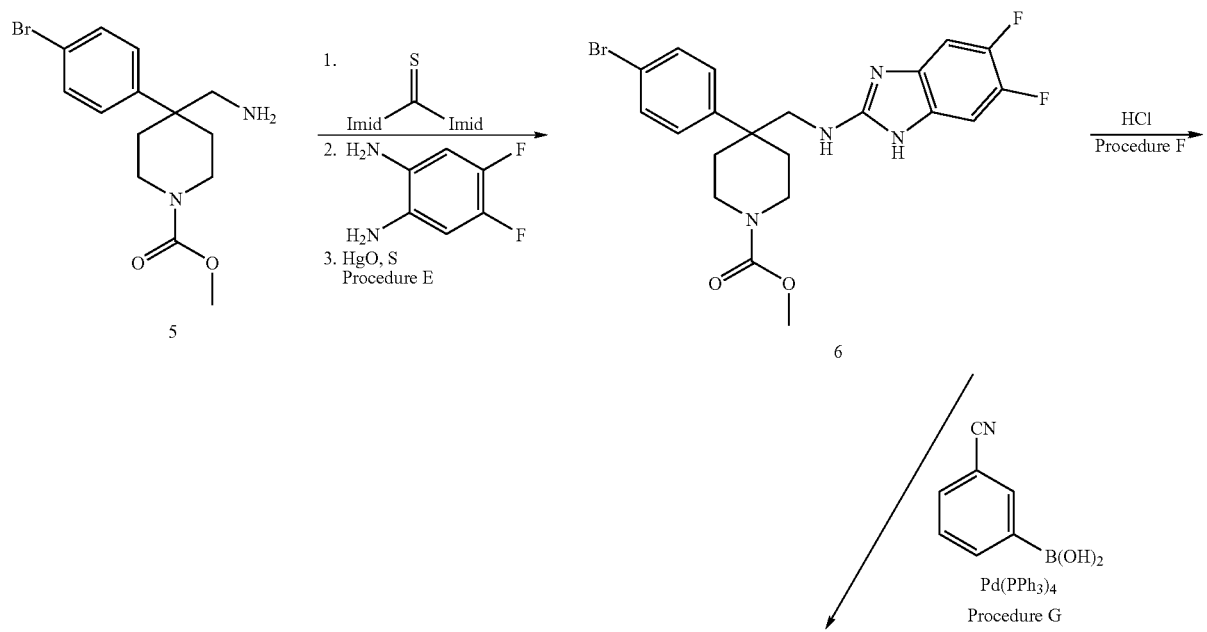
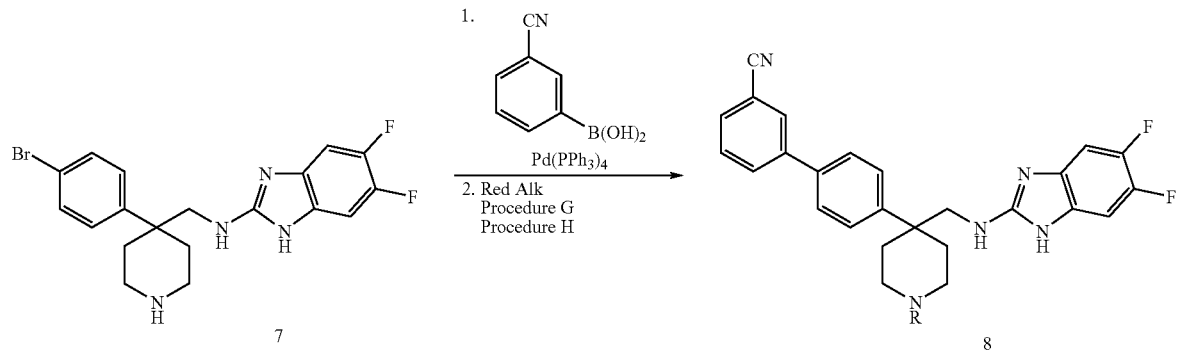

Benzimidazoles-Carbon-Linked Series, 4,4-Disubstituted Piperidine Series:
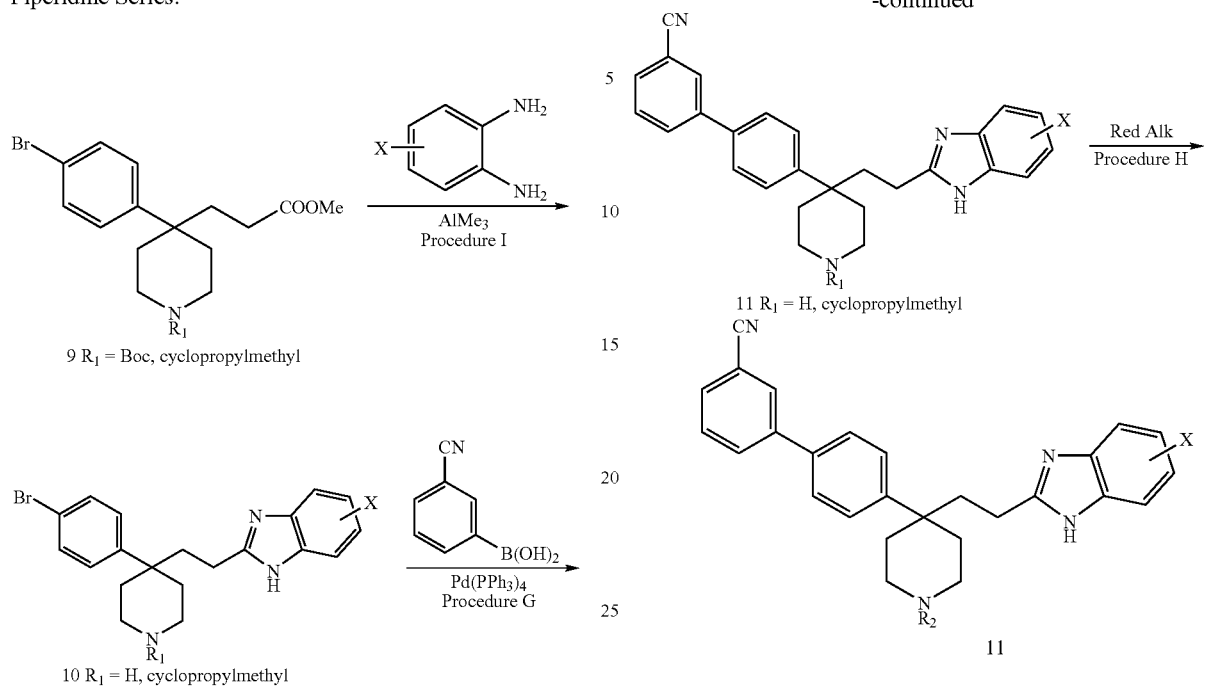
Benzimidazoles-Homolog Series:
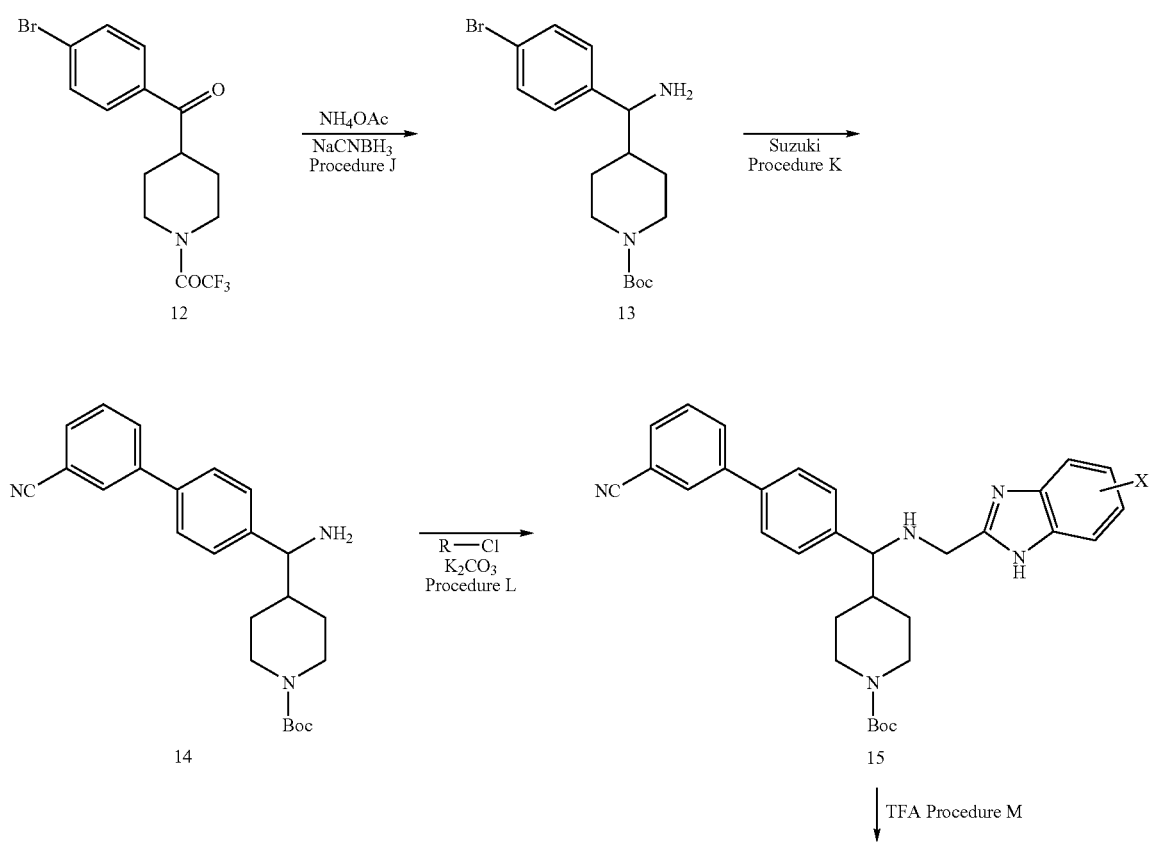

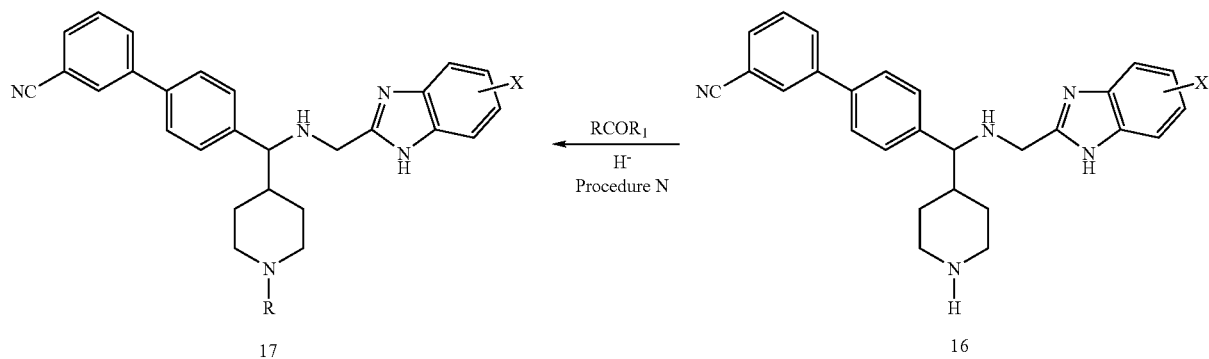
Aminobenzimidazoles-Homolog Series:
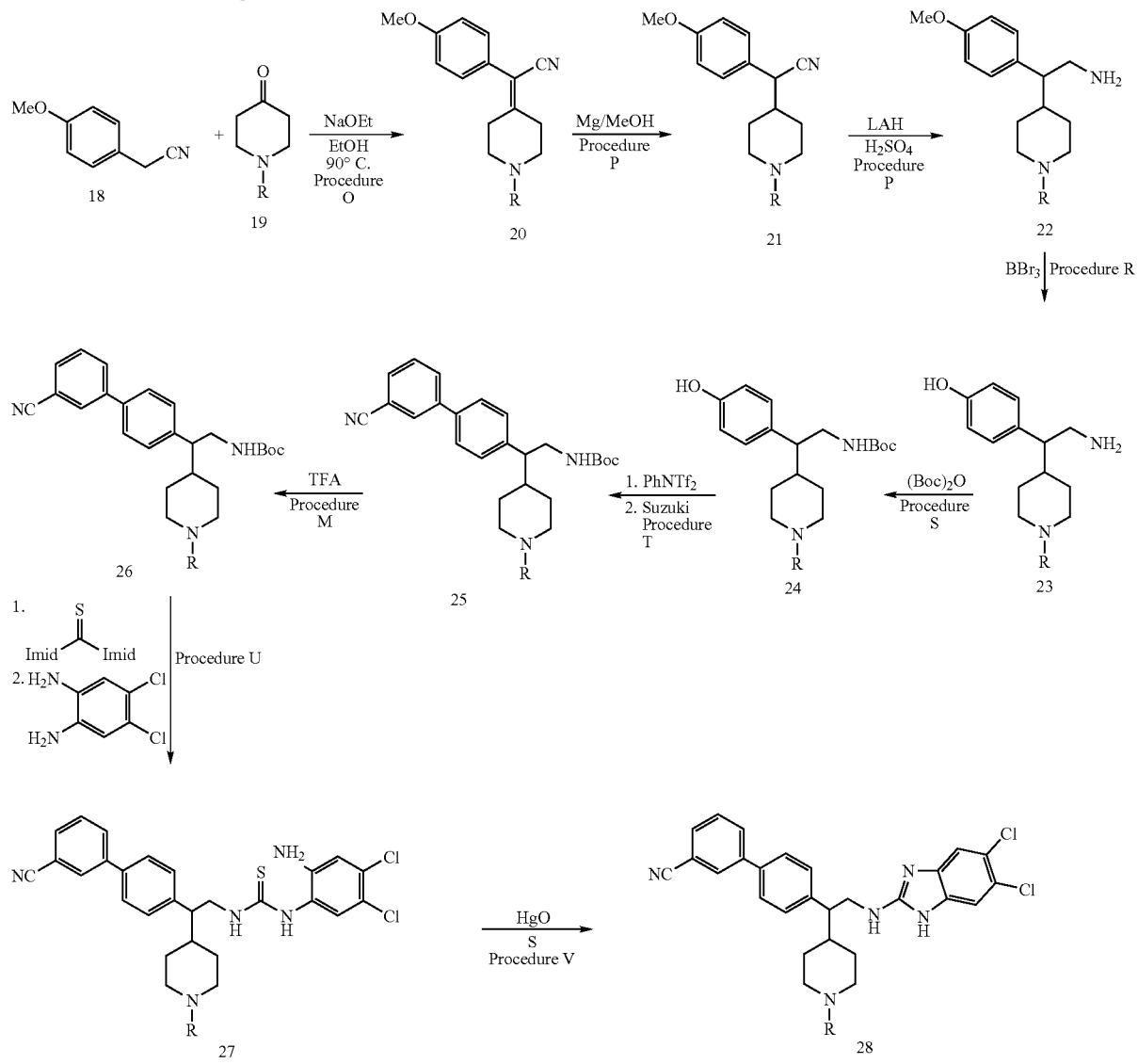

Ether-linked Benzimidazoles-Homolog Series:
NH and N-alkyls
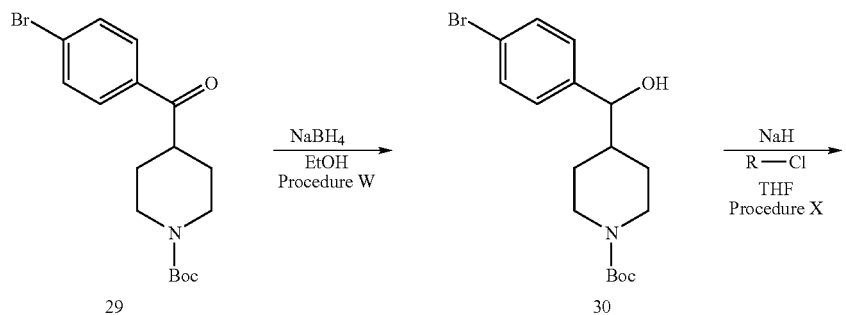
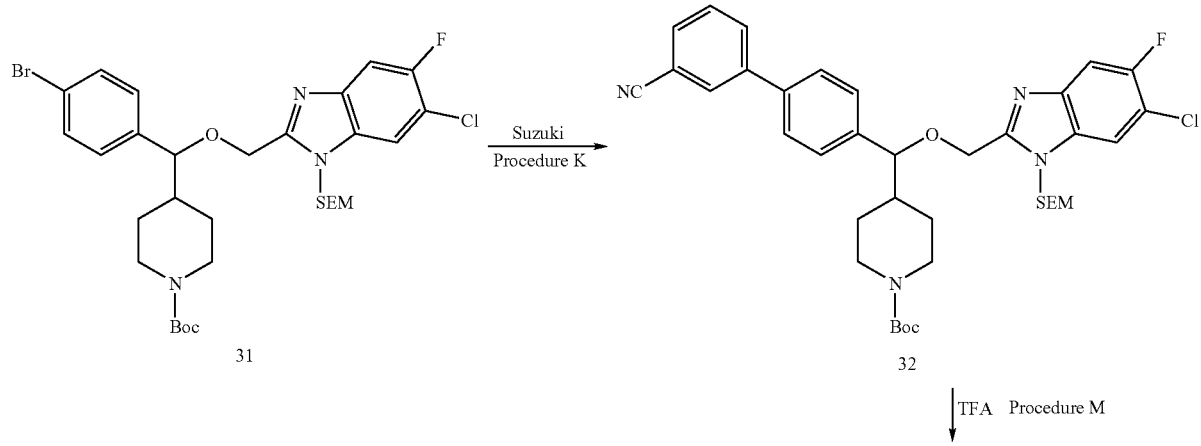
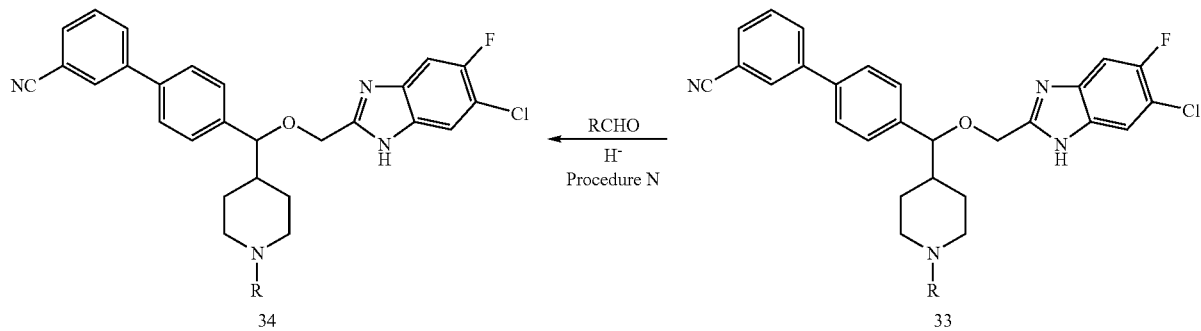

N-Sulfonamides:
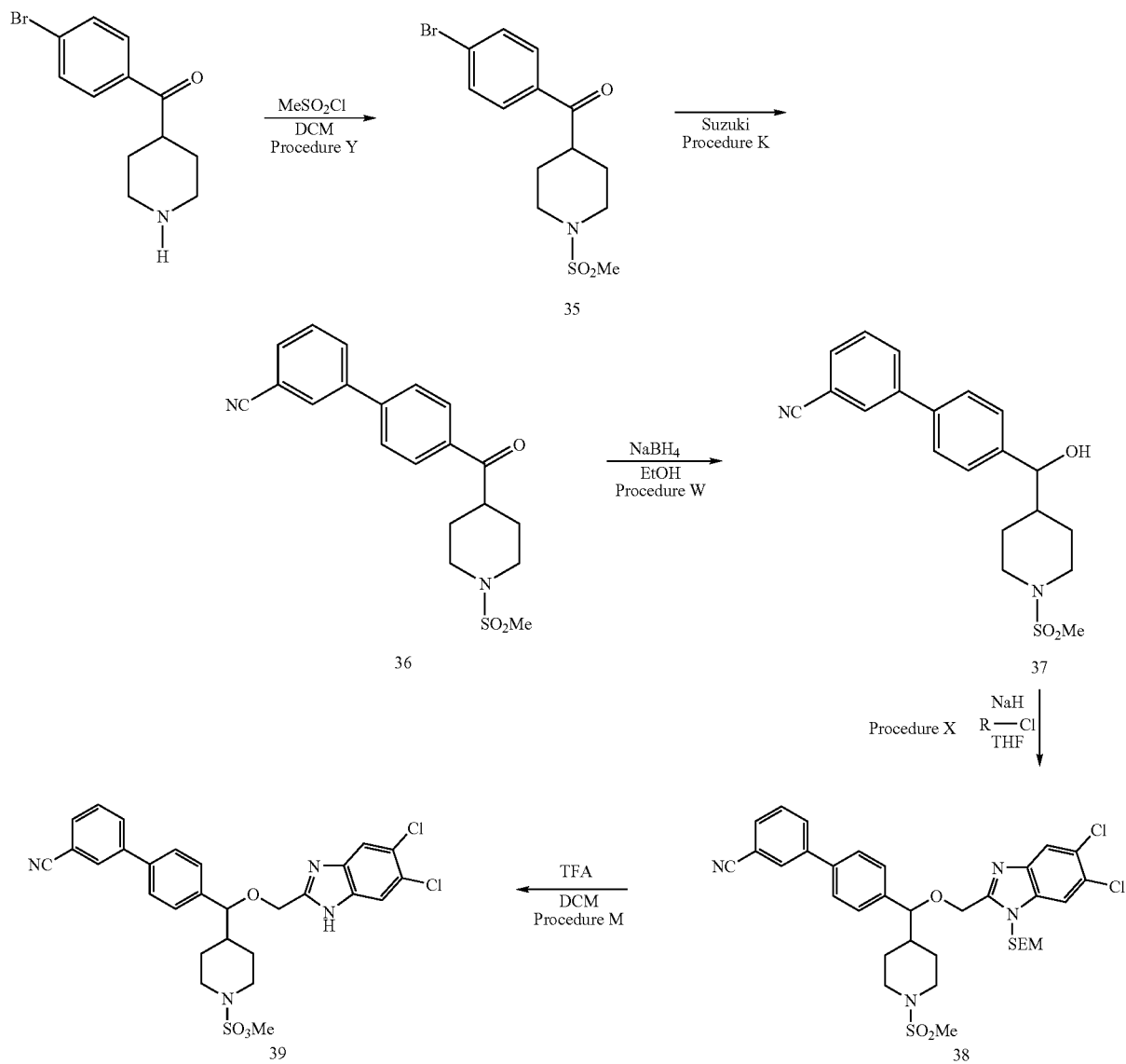
N-Acylated Analogs
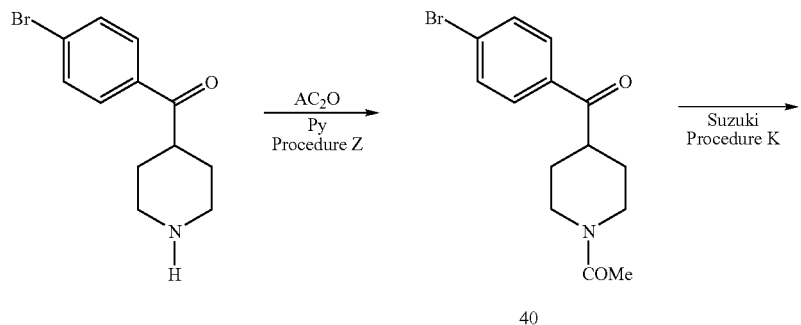

-continued
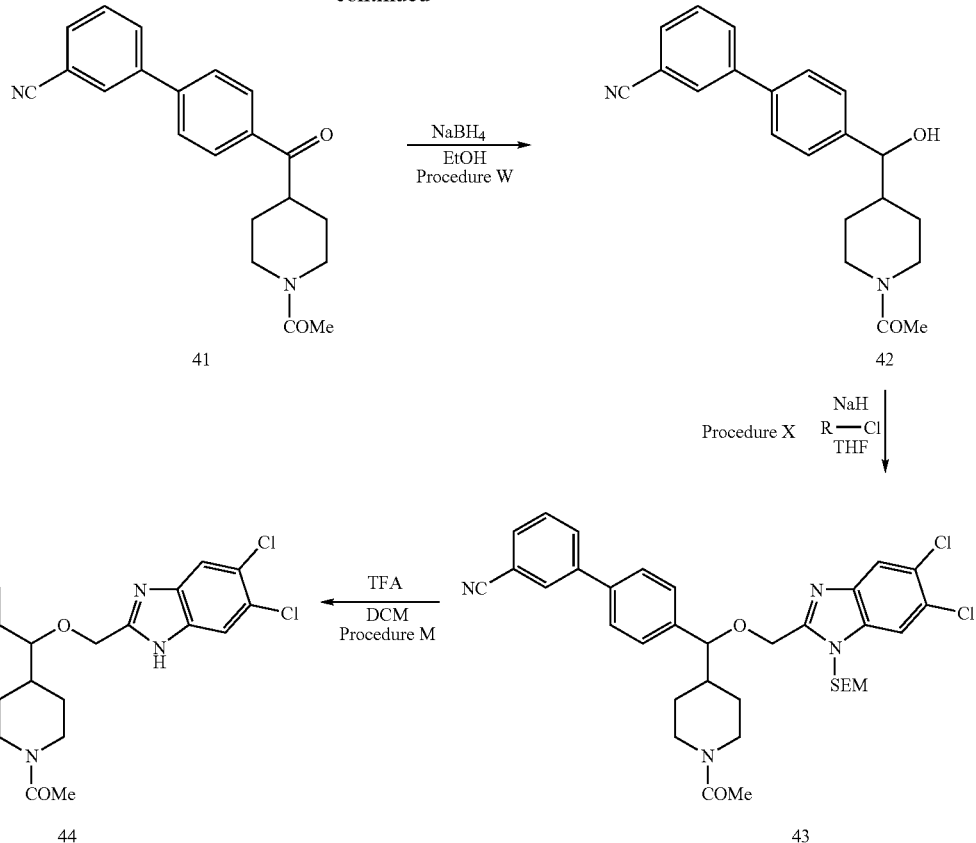
Alkylthiobenzimidazoles:
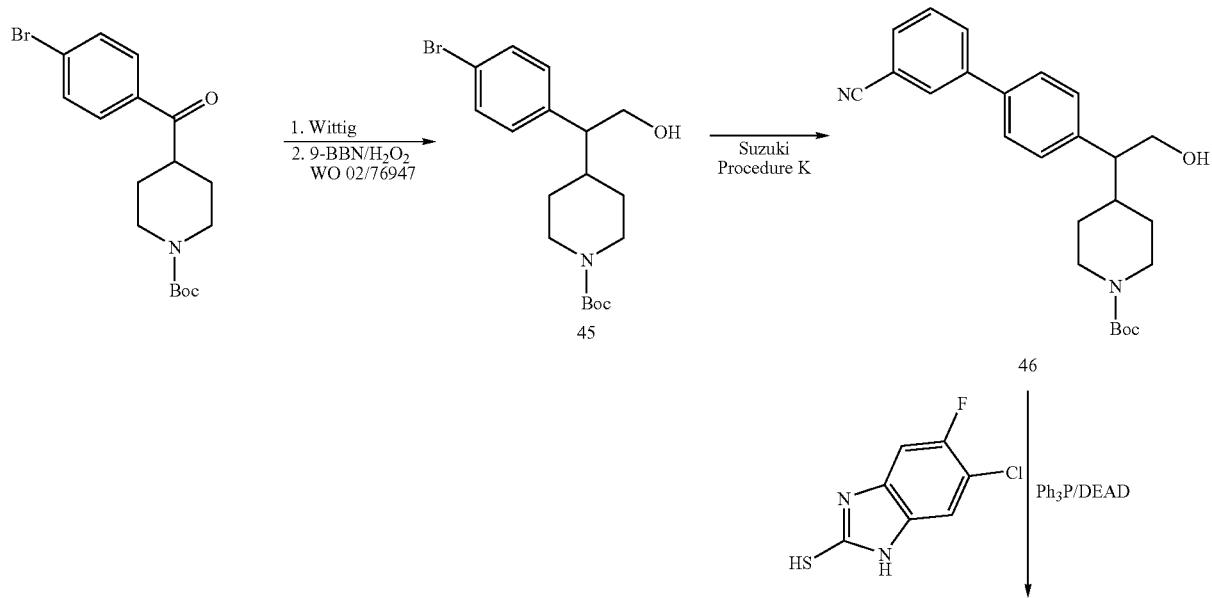

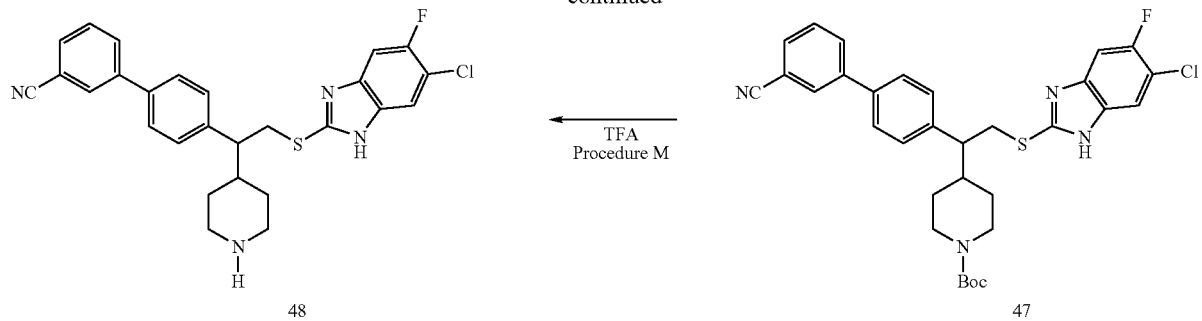
Alkoxybenzimidazoles-4,4-Disubstituted Piperidines:
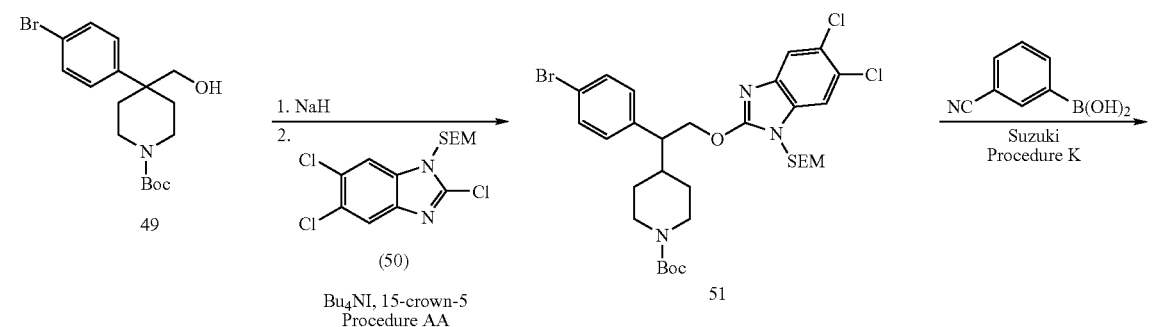
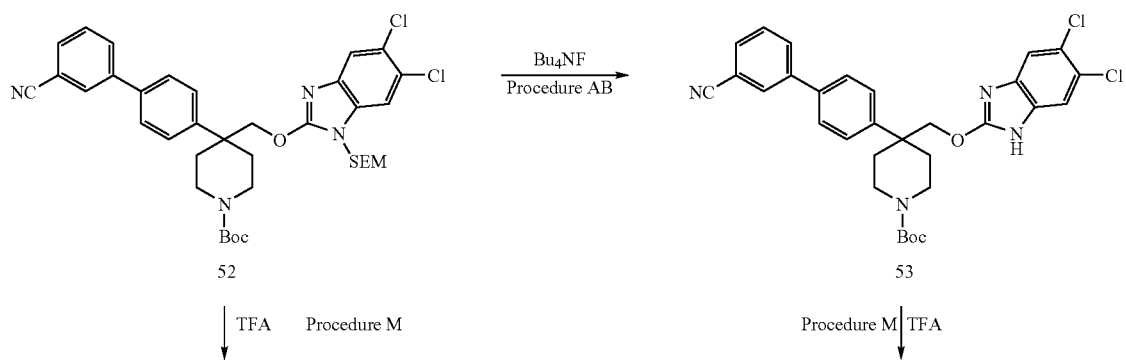
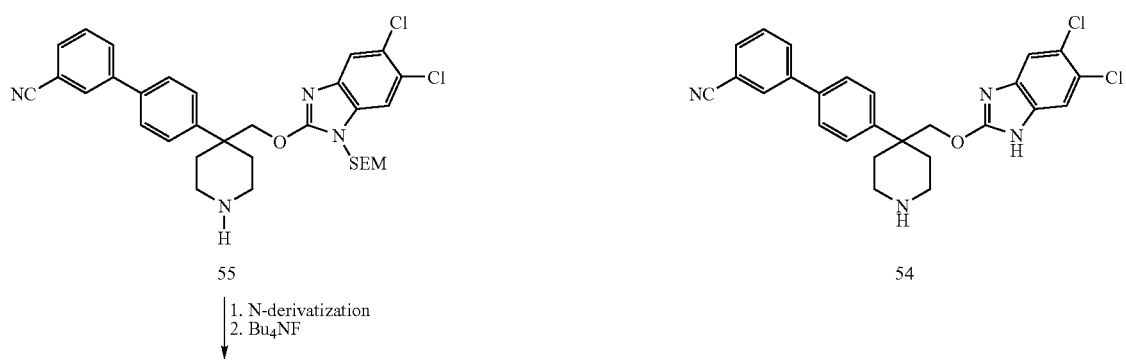

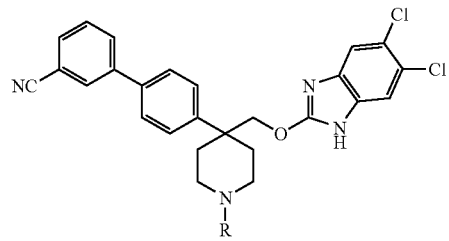
56: R = MeSO₂—
57: R = cyclopropylmethyl-
58: R = EtHNCO—
Ether-linked Alkylbenzimidazoles: 4,4-Disubstituted Piperidines:
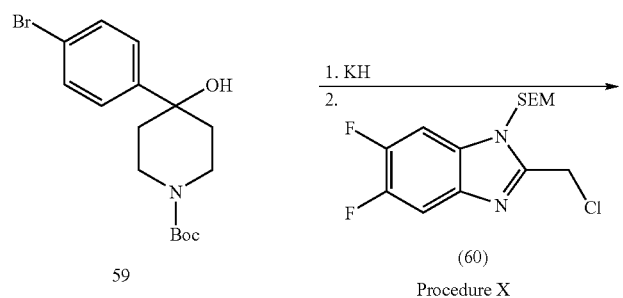
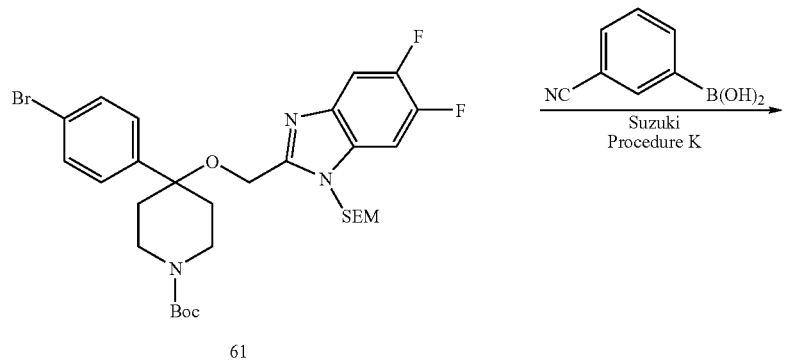
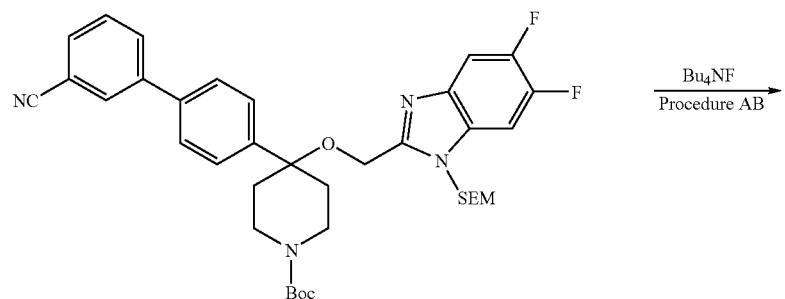

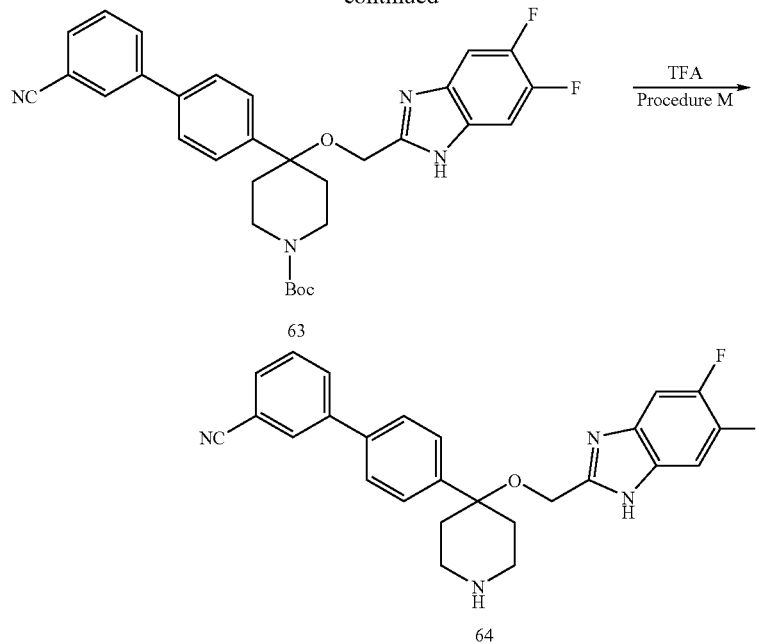
N-linked Alkylbenzimidazoles: 4,4-Disubstituted Piperidines
Benzimidazoles-Carbon-Linked Series, Homologated Piperidine Series:
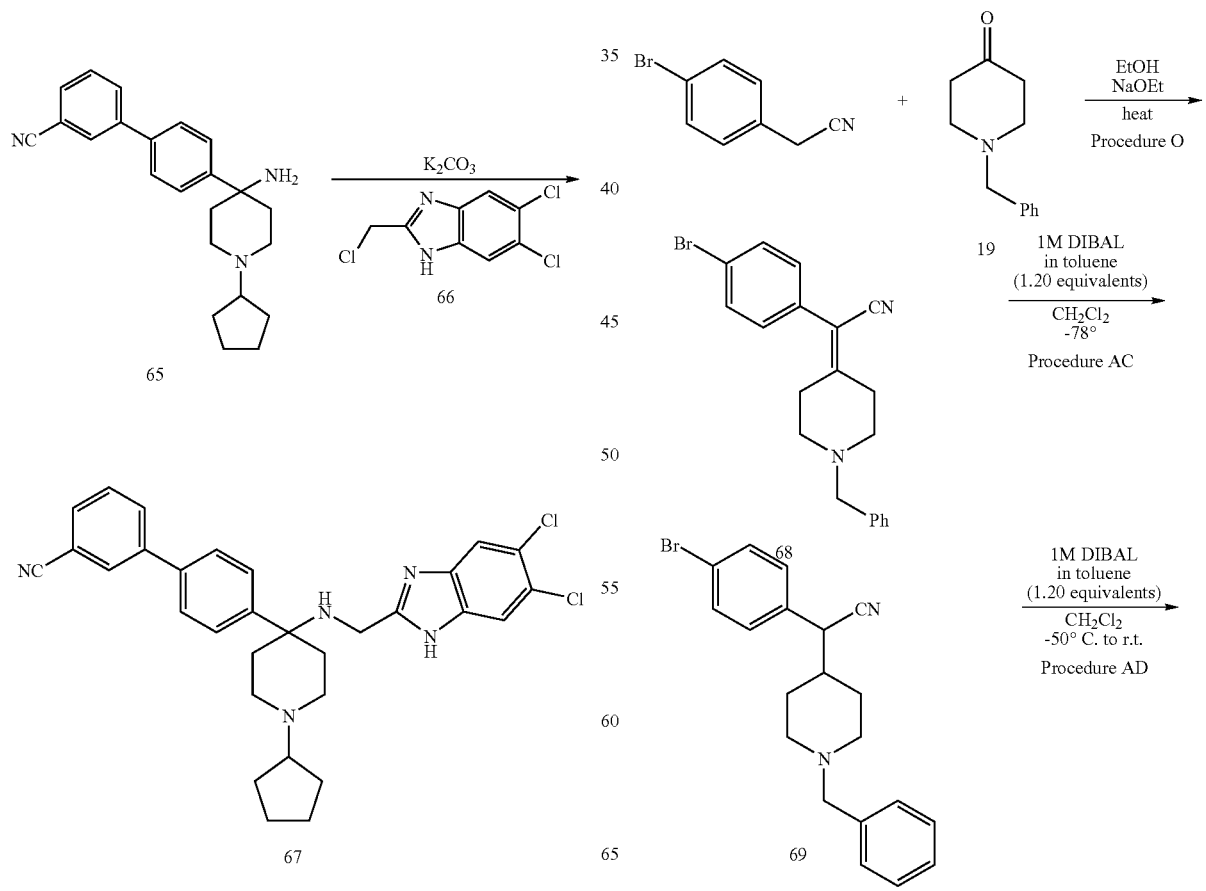

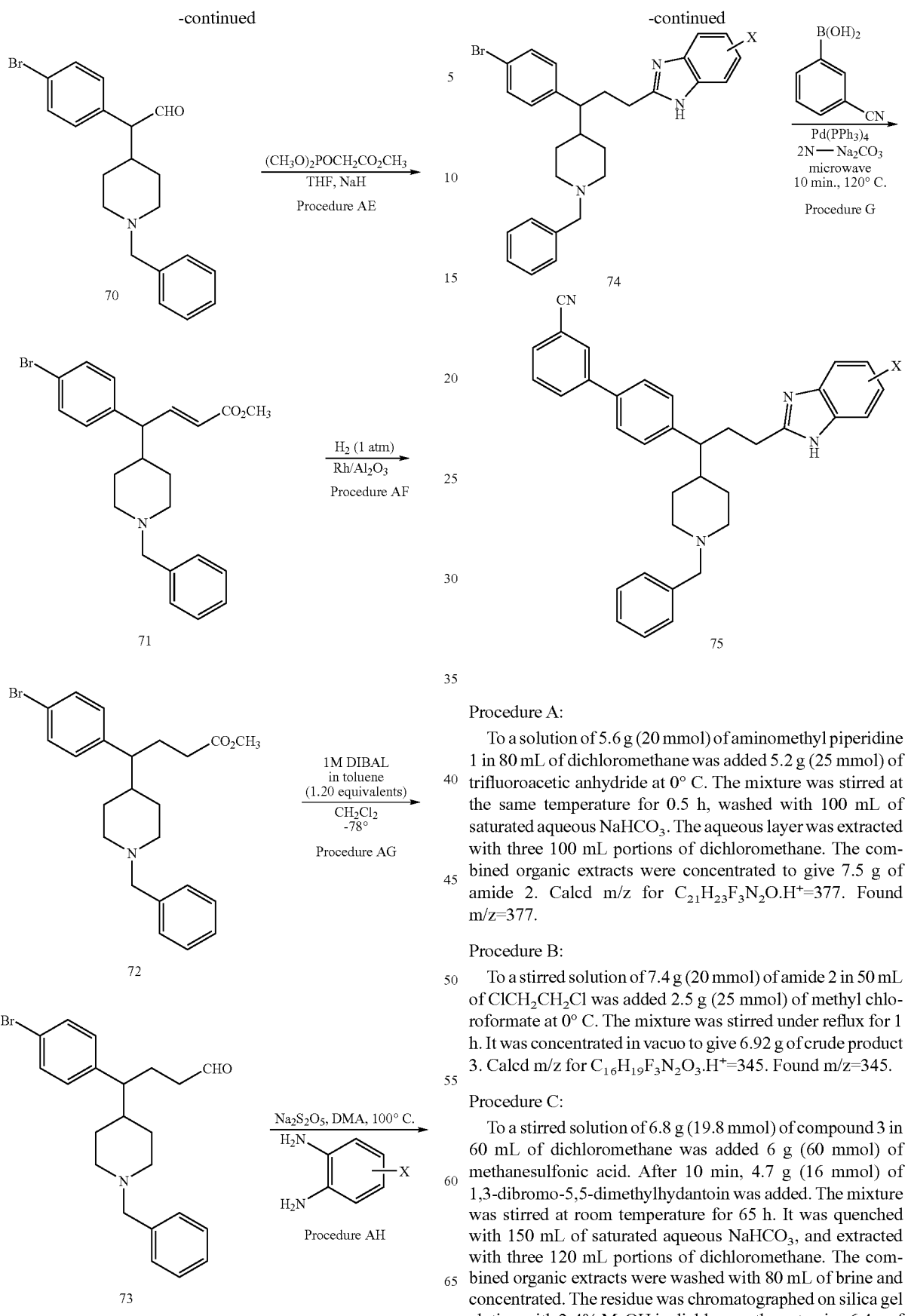

Procedure A:

To a solution of 5.6 g (20 mmol) of aminomethyl piperidine 1 in 80 mL of dichloromethane was added 5.2 g (25 mmol) of trifluoroacetic anhydride at 0° C. The mixture was stirred at the same temperature for 0.5 h, washed with 100 mL of saturated aqueous NaHCO$_3$. The aqueous layer was extracted with three 100 mL portions of dichloromethane. The combined organic extracts were concentrated to give 7.5 g of amide 2. Calcd m/z for $C_{21}H_{23}F_3N_2O.H^+$=377. Found m/z=377.

Procedure B:

To a stirred solution of 7.4 g (20 mmol) of amide 2 in 50 mL of ClCH$_2$CH$_2$Cl was added 2.5 g (25 mmol) of methyl chloroformate at 0° C. The mixture was stirred under reflux for 1 h. It was concentrated in vacuo to give 6.92 g of crude product 3. Calcd m/z for $C_{16}H_{19}F_3N_2O_3.H^+$=345. Found m/z=345.

Procedure C:

To a stirred solution of 6.8 g (19.8 mmol) of compound 3 in 60 mL of dichloromethane was added 6 g (60 mmol) of methanesulfonic acid. After 10 min, 4.7 g (16 mmol) of 1,3-dibromo-5,5-dimethylhydantoin was added. The mixture was stirred at room temperature for 65 h. It was quenched with 150 mL of saturated aqueous NaHCO$_3$, and extracted with three 120 mL portions of dichloromethane. The combined organic extracts were washed with 80 mL of brine and concentrated. The residue was chromatographed on silica gel eluting with 2-4% MeOH in dichloromethane to give 6.4 g of brominated compound 4 contaminated ca. 25% of starting material 3. Calcd m/z for $C_{16}H_{18}BrF_3N_3O_3 \cdot H^+ = 425$. Found m/z=425.

Procedure D:

A mixture of 4.2 g (10 mmol) of compound 4 and 2.8 g (20 mmol) of $K_2CO_3$ in 28 mL of MeOH—$H_2O$ (5:2) was stirred at RT for 20 h and concentrated. The residue was dissolved in 30 mL of $H_2O$, extracted with four 60 mL portions of $CHCl_3$. The combined organic extracts were washed with 30 mL of brine and concentrated. The residue was purified by preparative TLC eluting with 2-4% MeOH in dichloromethane containing 1% $NH_4OH$ to give 1.2 g of pure amine 5 and 2.0 g of amine 5 containing starting material 4. Compound 5: Calcd m/z for $C_{14}H_{19}BrN_2O_2 \cdot H^+ = 327$. Found m/z=327.

Procedure E:

To a stirred solution of 0.54 g (3 mmol) of 1,1'-thiocarbonyldiimidazole and 40 mg (0.6 mmol) of imidazole in 10 mL of acetonitrile was added a solution of 0.65 g (2 mmol) of amine 5 in 8 mL of acetonitrile. The mixture was stirred at room temperature for 3 h, then 0.6 g (4.16 mmol) of 4,5-difluorobenzene-1,2-diamine was added. The reaction was heated at 50° C. for 20 h followed by concentration in vacuo. To the residue in 25 mL of ethanol was added 0.86 g (4 mmol) of HgO (red) and 0.15 g of sulfur. After heating under reflux for 1 h, the mixture was filtered through a pad of celite. The filtrate was concentrated; the residue was chromatographed on silica gel eluting with 1-8% MeOH in dichloromethane containing 1% $NH_4OH$ to give 1.86 g of aminobenzimidazole 6. Calcd m/z for $C_{21}H_{21}BrF_2N_4O_2 \cdot H^+ = 479$. Found m/z=479.

Procedure F:

To a solution of 0.55 g (1.15 mmol) of compound 6 in 5 mL of ethanol was added 15 mL of 6N aqueous HCl. The solution was heated under reflux for 18 h. It was concentrated to a volume of ~15 mL, basified with 25 mL of diluted $NH_4OH$ and extracted with four 50 mL portions of dichloromethane. The combined organic extracts were washed with 30 mL of brine, and concentrated to give 0.43 g of piperidine 7. Calcd m/z for $C_{19}H_{19}BrF_2N_4 \cdot H^+ = 421$. Found m/z=421.

Procedure G:

A mixture of 0.42 g (1 mmol) of compound 7, 0.2 g (1.2 mmol) of 3-cyanophenylboronic acid, 0.1 g (0.01 mmol) of $Pd(PPh_3)_4$ in 1 mL of 1N $Na_2CO_3$ and 4.5 mL of methanol in a sealed tube was heated at 120° C. for 10 min under microwave irradiation. It was diluted with 20 mL of methanol and filtered. The filtrate was concentrated and the residue was purified by preparative TLC eluting with 10% MeOH in dichloromethane containing 1% $NH_4OH$ to give 0.18 g of compound 8A.

The following compounds have been prepared analogously:

| Cpd. # | Structure | Formula $(M + 1)^+$ | calcd m/z | obsd m/z |
|---|---|---|---|---|
| 8A | 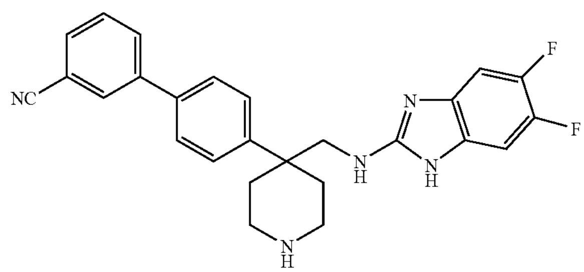 | $C_{26}H_{23}F_2N_5 \cdot H^+$ | 444 | 444 |
| 8D | 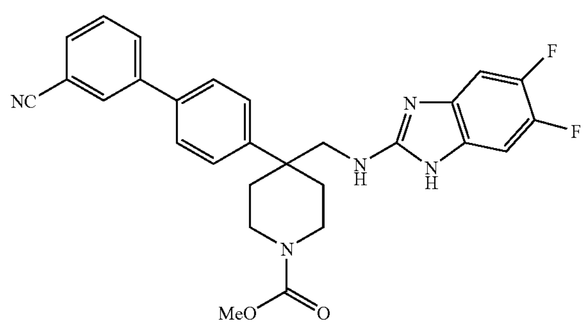 | $C_{28}H_{25}F_2N_5O_2 \cdot H^+$ | 502 | 502 |

Procedure H:

To a stirred solution of 0.044 g (0.1 mmol) of compound 8A and 8 mg (1.2 mmol) of cyclopropanecarboxaldehyde in 2 mL of dichloromethane-methanol (1:1) was added 0.03 g (0.14 mmol) of $NaBH(OAc)_3$. The mixture was stirred art room temperature for 18 h and purified by resin clean-up using Argonaut Technologies, Inc. p-toluene sulfonic acid resin, MP-TsOH (1.29 mmol/g) to give 0.039 g of alkylated piperidine 8B.

The following compounds have been prepared analogously:

| Cpd. # | Structure | Formula (M + 1)+ | calcd m/z | obsd m/z |
|---|---|---|---|---|
| 8B | 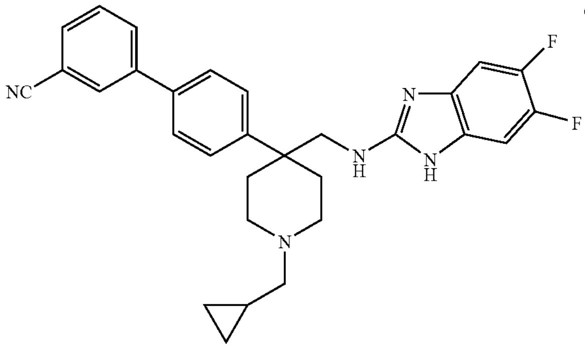 | $C_{30}H_{29}F_2N_5 \cdot H^+$ | 498 | 498 |
| 8C | 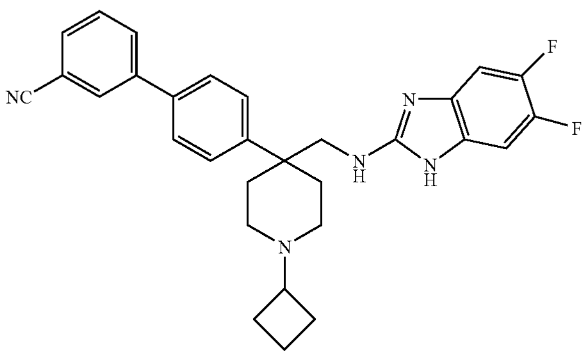 | $C_{30}H_{20}F_2N_5 \cdot H^+$ | 498 | 498 |
| 11A | 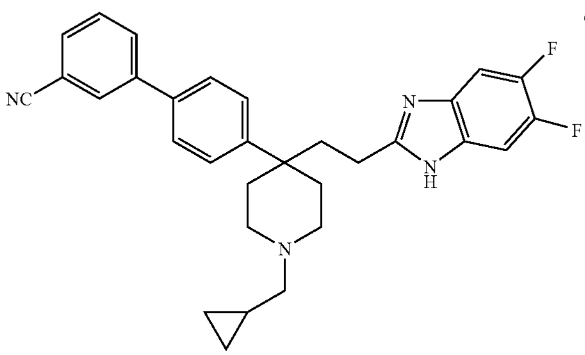 | $C_{31}H_{30}F_2N_4 \cdot H^+$ | 497 | 497 |
| 11B | 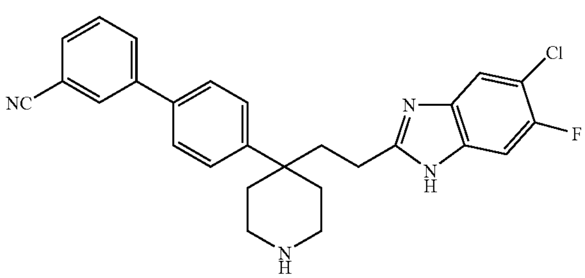 | $C_{27}H_{24}ClFN_4 \cdot H^+$ | 459 | 459 |

-continued

| Cpd. # | Structure | Formula (M + 1)+ | calcd m/z | obsd m/z |
|---|---|---|---|---|
| 11C | 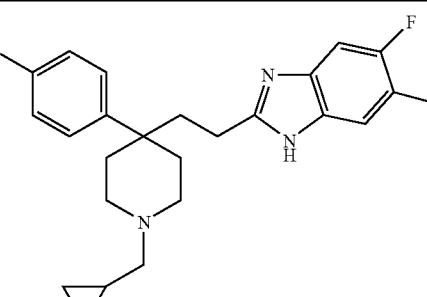 | C31H30ClFN4•H+ | 513 | 513 |

Procedure I:

To a stirred solution of 0.52 g (0 mmol) of 4,5-difluorobenzene-1,2-diamine in 8 mL of toluene was added 5 mL (10 mmol) of AlMe$_3$ in toluene. After 20 min, a solution of 1.0 g (2.6 mmol) of compound 9A (R$_1$=n-Boc) in toluene was introduced. The mixture was stirred under reflux for 18 h and cooled to room temperature. The reaction was quenched with 70 mL of saturated aqueous NaHCO$_3$, and extracted with three 60 mL portions of dichloromethane. The combined organic extracts were washed with 50 mL of brine and concentrated. The residue was chromatographed over silica gel eluting with 1-10% methanol in dichloromethane containing 1% NH$_4$OH to give 0.25 g of compound 10A.

The following compounds have been prepared analogously:

Procedure J:

Step 1:

To a solution of 12 g (33 mmol) of compound 12 (Anandan Palani, et al, *J. Med. Chem.* 2002, 45, 3143) in 100 mL of methanol-H$_2$O (1:3) was added 10 g (72 mmol) of K$_2$CO$_3$. The solution was stirred at room temperature for 18 h and concentrated to a volume of ca. 70 mL. It was diluted with 100 mL of H$_2$O and extracted with three 150 mL portions of dichloromethane. The combined organic extracts were washed with 50 mL of brine and concentrated. The residue was chromatographed on silica gel eluting with 3 to 12% methanol in dichloromethane containing 1% NH$_4$OH to give 7 g of the desired N-unsubstituted piperidine. Calcd m/z for C$_{12}$H$_{14}$BrNO.H$^+$=268. Found m/z=268.

| Cpd. # | Structure | Formula (M + 1)+ | calcd m/z | obsd m/z |
|---|---|---|---|---|
| 10A | 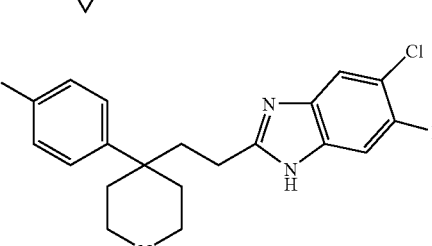 | C24H26BrF2N3•H+ | 476 | 476 |
| 10B | 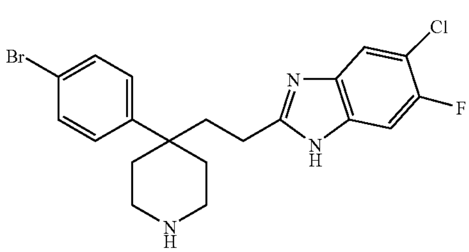 | C20H20BrClFN3•H+ | 438 | 438 |

Step 2:

To a solution of 7 g (26 mmol) of the piperidine from step 1 in 150 mL of methanol was added 6.5 g (30 mmol) of (Boc)$_2$O. The mixture was stirred at room temperature for 2 h and concentrated. The residue was recrystalized from methanol to give N-Boc piperidine. Calcd m/z for C$_{17}$H$_{22}$BrNO$_3$.H$^+$=368. Found m/z=368.

Step 3:

To a solution of the N-Boc protected bromophenyl ketone from step 2 (2.0 g, 5.43 mmol) in dichloroethane (2 mL) was added NH$_4$OAc (5.0 g, 64.0 mmol) and NaCNBH$_4$ (1.0 g, 15.9 mmol, in 2 mL methanol). The reaction mixture was stirred at room temperature for 48 h. Water (100 mL) was added and the mixture was extracted with dichloromethane (2×100 mL). The organic layer was dried using sodium sulfate and removal of the solvent afforded amino compound 13 as an oil in 90% yield. Calcd m/z for C$_{17}$H$_{25}$BrN$_2$O$_2$.H$^+$ =369.1. Found m/z=369.1.

removed in vacuo and the product was isolated by silica gel column chromatography using 5-10% methanol in dichloromethane as eluent to afford compound 14 in 57% yield. Calcd m/z for C$_{24}$H$_{29}$N$_3$O$_3$.H$^+$=392.2. Found m/z=392.1.

Procedure L:

To a solution of compound 14 (0.08 g, 0.204 mmol) in acetonitrile (5 mL) was added K$_2$CO$_3$ (0.2 g, 1.45 mmol) and 6-chloro-2-chloromethyl-5-fluoro-1H-benzimidazole (0.05 g, 0.228 mol) and the contents were stirred at room temperature for 3 h. The reaction mixture was diluted with 50 mL of dichloromethane and filtered through Celite. The solvent was removed in vacuo and the residue was purified by silica gel column chromatography using 5-10% methanol in dichloromethane to give 0.07 g of compound 15B as an oil. Calcd m/z for C$_{32}$H$_{33}$ClFN$_5$O$_2$.H$^+$=574.2. Found m/z=574.1.

The following compounds have been prepared using this or analogous methods:

| Cpd. # | Structure | Formula (M + 1)$^+$ | calcd m/z | obsd m/z |
|---|---|---|---|---|
| 15A | 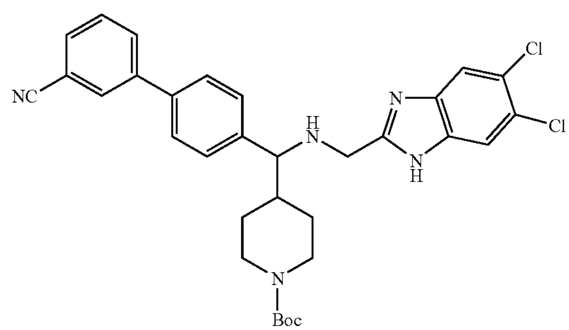 | C$_{32}$H$_{33}$Cl$_2$N$_5$O$_2$•H$^+$ | 590.2 | 590.1 |
| 15B | 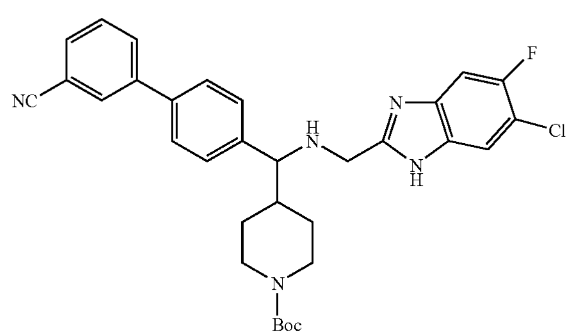 | C$_{32}$H$_{33}$ClFN$_5$O$_2$•H$^+$ | 574.2 | 574.1 |

Procedure K:

To a solution of bromophenyl amine compound 13 (1.66 g, 4.5 mmol) in toluene/methanol (1:1, 50 mL) was added 3-cyanophenyl boronic acid (1.0 g, 6.6 mmol), aq. Na$_2$CO$_3$ (2 N, 5 mL) and Pd(PPh$_3$)$_4$ (0.5 g, 5.6 mol %). The solution was purged with nitrogen for 5 minutes and heated at 90° C. overnight. The reaction mixture was diluted with dichloromethane and filtered through celite. The solvent was Procedure M Trifluoroacetic acid (1 mL) was added to a solution of compound 15B (0.064 g, 0.111 mmol) in 2 mL of dichloromethane and the mixture was stirred for 2 h at room temperature. The solvent was removed in vacuo and the piperidine product 16B was used as such for the next step without any further purification.

The following compounds were prepared using analogously:

| Cpd. # | Structure | Formula (M + 1)+ | calcd m/z | obsd m/z |
|---|---|---|---|---|
| 16A | 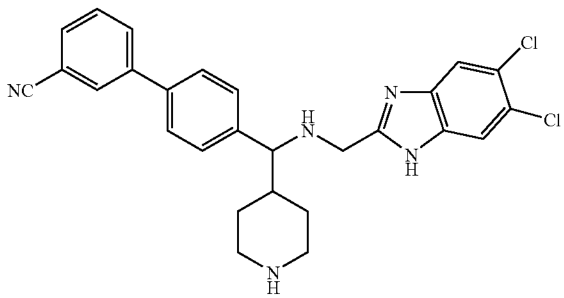 | $C_{27}H_{25}Cl_2N_5 \cdot H^+$ | 490.2 | 490.1 |
| 16B | 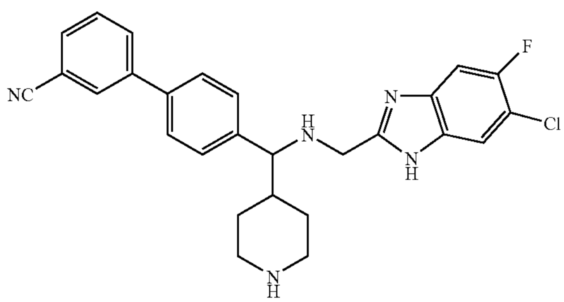 | $C_{27}H_{25}ClFN_5 \cdot H^+$ | 474.2 | 474.1 |

Procedure N

To a solution of piperidine 16B (0.01 g, 0.0142 mmol) in 2 ml of methanol was added cyclopropanecarboxaldehyde (5 mg, 0.071 mmol) and NaCNBH$_3$ (0.01 g, 0.05 mmol) and the contents were stirred at room temperature for 2 h. The residue was purified by prep TLC using 10% methanol in dichloromethane as eluent to give 0.003 mg of the alkylated piperidine product 17A as an oil. Calcd m/z for $C_{31}H_{31}ClFN_5 \cdot H^+$ = 528.2. Found m/z=528.1.

| Cpd. # | Structure | Formula (M + 1)+ | calcd m/z | obsd m/z |
|---|---|---|---|---|
| 17A | 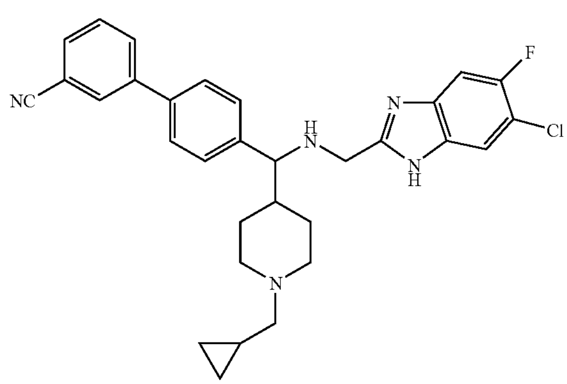 | $C_{31}H_{31}ClFN_5 \cdot H^+$ | 528.2 | 528.1 |

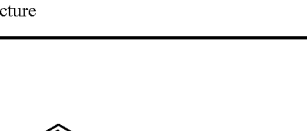

-continued

| Cpd. # | Structure | Formula (M + 1)+ | calcd m/z | obsd m/z |
|---|---|---|---|---|
| 17B | 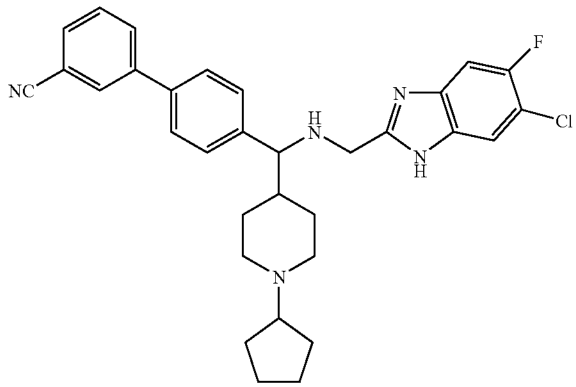 | $C_{32}H_{33}ClFN_5 \cdot H^+$ | 542.2 | 542.1 |

Procedure O:

To a mixture of 4-methoxyphenyl acetonitrile (10 g, 67.9 mmol) and N-benzyl piperidone (13 g, 68.6 mol) in 100 mL of ethanol was added NaOEt (7.0 g, 102.0 mmol) and the contents were heated at 90° C. for 3 h. The reaction mixture was cooled to room temperature and poured into a mixture of acetic anhydride/pyridine (1:1, 200 mL). The mixture was stirred for 2 h and the solvents were removed in vacuo. The residue was purified by silica gel chromatography using 2% methanol in dichloromethane to give 15.0 g of the conjugated nitrile 20 as a light brown solid. Calcd m/z for $C_{21}H_{22}N_2O \cdot H^+=319.2$. Found m/z=319.1.

Procedure P:

To a solution of compound 20 (7.5 g, 23.5 mmol) in 100 mL of methanol was added magnesium turnings (5.7 g, 10 eq) and iodine (500 mg) and the contents were stirred for 3 h at room temperature. The inorganic material was filtered and water was added to the methanol solution. The precipitated gel was extracted with EtOAc (3×200 mL) and isopropanol (2×200 mL). The solvent was removed in vacuo and the residue 21 (6.0 g) was used without further purification for the next step. Calcd m/z for $C_{21}H_{24}N_2O \cdot H^+=321.2$. Found m/z=321.1.

Procedure Q:

To a solution of lithium aluminum hydride (1 M solution in THF, 47 mL, 3 eq) in THF was added $H_2SO_4$ (2.15 mL, 3.2 eq) at 0° C. very slowly. The resulting white slurry was stirred at room temperature for 30 minutes and at 30° C. for 15 minutes. Compound 21 (5.0 g, 15.6 mmol) in 50 mL of THF was cannulated to the alane solution and the resulting mixture was stirred at 55° C. for 3 h. The reaction mixture was cooled to room temperature and quenched with water (1.62 mL), 1N NaOH (3.23 mL) and water (4.85 mL). Dichloromethane (~100 mL) was added and the mixture was filtered through Celite. The solvent was evaporated to give 4.05 g of amine 22 as a colorless solid. Calcd m/z for $C_{21}H_{28}N_2O \cdot H^+=325.2$. Found m/z=325.1.

Procedure R:

Compound 22 (4.05 g, 12.48 mol) was dissolved in 100 mL of dichloromethane and treated with $BBr_3$ (3.54 mL, 37.4 mmol) at −78° C. The reaction mixture was warmed to room temperature and stirred for 3 h. The reaction mixture was cooled to −78° C. and carefully quenched by the addition of 50 mL of methanol. The reaction was slowly warmed to room temperature and heated under reflux for 30 minutes. The solvent was removed in vacuo to give 3.5 g of the desired phenol 23 as a light yellow solid. Calcd m/z for $C_{20}H_{26}N_2O \cdot H^+=311.2$. Found m/z=311.1.

Procedure S:

To a solution of compound 23 (3.5 g, 11.27 mol) in 50 mL of methanol was added triethylamine (2 mL) and $(Boc)_2O$ (2.7 g, 12.3 mol) at room temperature and the mixture was stirred for 4 h. The solvent was removed in vacuo and the product 24 was used without further purification in the next step.

Procedure T:

Phenol 24 (4.6 g, 11.2 mmol) was dissolved in 100 mL of dichloromethane and treated with triethylamine (10 mL) and $PhNTf_2$ (5.0 g, 13.9 mmol) at room temperature and the mixture was stirred for 6 h. The solvent was removed in vacuo to give the triflate as brown oil. To the crude triflate (6.0 g, 11.0 mmol) in 100 mL of toluene/methanol (1:1) was added 3-cyanophenyl boronic acid (3.25 g, 2 eq), aq. $Na_2CO_3$ (2N, 10 mL), and $Pd(PPh_3)_4$ (1.2 g, 10 mol %) and the resulting solution was flushed with nitrogen. The contents were heated at 90° C. overnight and passed through a short pad of Celite. The solids were washed with ethyl acetate and the filtrate was concentrated in vacuo. The residue was purified by silica gel column chromatography eluting with 20-60% ethyl acetate in hexane to give 3.0 g of the desired biaryl 25 as a colorless powder. Calcd m/z for $C_{32}H_{37}N_3O_2 \cdot H^+=496.3$. Found m/z=496.3.

The Boc protecting group was removed analogously to procedure M as follows:

To a solution of compound 25 (0.885 g, 1.785 mmol) in 10 mL of dichloromethane was added 2 mL of trifluoroacetic acid at 0° C. and the mixture stirred for 1 h. The reaction was warmed to room temperature and stirred for an additional 2 h. The reaction mixture was quenched by the addition of $NH_4OH$ and extracted with dichloromethane (2×50 mL). The extracts were concentrated in vacuo and the residue 26 (0.6 g) was used directly in the next step. Calcd m/z for $C_{27}H_{29}N_3 \cdot H^+=396.2$. Found m/z=396.1.

Procedure U:

To a flask containing 0.12 g (0.66 mmol, 1.5eq.) of thiocarbonyldiimidazole and 9 mg of imidazole (0.13 mmol, 0.3eq.) was added 1.5 mL of acetonitrile. The reaction was cooled to 0° C. and then a solution of 1 mL of acetonitrile containing 0.17 g (0.44 mmol, 0.3eq) of 4'-[2-amino-1-(1-benzyl-piperidin-4-yl)-ethyl]-biphenyl-3-carbonitrile was added over ten minutes. After 10 minutes at 0° C. the reaction was stirred for 3 hours at room temperature at which time 0.16 g (0.90 mmol, 2eq.) of 4,5-dichlorophenylenediamine were added. The reaction was heated to 50° C. for 3 hours and then stirred at room temperature overnight. The following morning the reaction was concentrated to give 0.27 g of thiourea 27 as a dark red-brown solid. Calcd m/z for $C_{34}H_{33}Cl_2N_5S.H^+=614.2$. Found m/z=614.1.

Procedure V:

To a flask containing ~0.27 g of the crude thiourea 27 were added 6.0 mL of ethanol, 0.19 g (0.9 mmol, 0.2eq) of HgO, and 9 mg (0.09 mmol, 0.2 eq) of sulfur. The reaction was heated under reflux for two hours and then cooled to room temperature. It was filtered through Celite and concentrated. The product was taken up in a 60% DMSO/30% $CH_3CN$/10% formic acid solution. It was then chromatographed via reverse phase HPLC using a C-18 column eluting with a gradient starting with 95% $CH_3CN$/5% $H_2O$ to 5% $CH_3CN$/95% $H_2O$ both containing 0.10% formic acid. This purification gave 24 mg of the formate salt of the desired aminobenzimidazole 28A as a yellow solid. Calcd m/z for $C_{34}H_{31}Cl_2N_5.H^+=580.2$. Found m/z=580.1.

The following compounds were prepared in analogous fashion:

Procedure W:

Bromophenyl ketone 29 from step 2 of procedure J (1.08 g, 2.9 mmol, A. Palani, et. al. *J. Med. Chem.* 2001, 44, 3339-3342) was dissolved in 10 mL of ethanol and treated with $NaBH_4$ (0.11 g, 2.9 mmol) at 0° C. The reaction mixture was slowly warmed to room temperature and stirred for 2 h. Methanol was added and the mixture stirred for 30 minutes. The solvent was removed and the reaction was purified by silica gel column using 40% ethyl acetate in hexane to give 0.79 g of the desired alcohol 30 as a white solid. Calcd m/z for $C_{17}H_{24}BrNO_3.H^+=370.1$. Found m/z=370.1.

Procedure X:

Step 1: Synthesis of SEM Protected chloromethylbenzimidazole

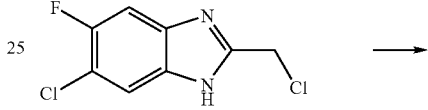

| Cpd. # | Structure | Formula (M + 1)+ | calcd m/z | obsd m/z |
|---|---|---|---|---|
| 28A | ![structure] | $C_{34}H_{31}Cl_2N_5 \cdot H^+$ | 580.2 | 580.1 |
| 28B | ![structure] | $C_{34}H_{31}F_2N_5 \cdot H^+$ | 548.2 | 548.1 |

-continued

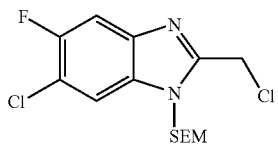

To a solution of 6-chloro-2-chloromethyl-5-fluoro-1H-benzoimidazole (2.0 g, 9.0 mmol) in 20 mL of tetrahydrofuran was added Hünig's base (1.92 mL, 1.2 eq) followed by SEM-CI (2.15 mL, 1.2 eq) at 0° C. The reaction was warmed to room temperature and stirred overnight. More SEM-CI (1 mL) was added and the reaction was stirred an additional 2 h. The solvent was removed in vacuo and the compound was purified by silica gel column using 30% ethyl acetate in hexane to give 0.45 g of the desired protected alkylating agent. Calcd m/z for $C_{14}H_{19}Cl_2FN_2OSi.H^+=349.1$. Found m/z=349.1.

Step 2: Alkylation Conditions:

To a solution of alcohol 30 (0.2 g, 0.54 mmol) in 3 mL of tetrahydrofuran was added NaH (0.023 g, 2eq, 60% in mineral oil) and the reaction was stirred at room temperature for 15 minutes. The SEM protected chloromethylbenzimidazole from Step 1 (0.22 g, 1.2 eq) was dissolved in 1 mL of tetrahydrofuran and added to the reaction mixture. The mixture was stirred for 4 h at room temperature. The reaction was quenched by the addition of methanol followed by concentration in vacuo. The reaction was purified by silica gel chromatography using 30-40% ethyl acetate in hexane mixture as the eluent to give 0.2 g of the ether 31 as an oil Calcd m/z for $C_{31}H_{42}BrClFN_3O_4Si.H^+=682.2$. Found m/z=682.2.

The biaryl molecules were prepared in this sequence analogous to Procedure K as follows:

To a solution of compound 31 (0.2 g, 0.29 mmol) in toluene/ethanol (1:1, 5 mL) was added 3-cyanophenyl boronic acid (0.052 g, 1.2 eq), aq. $Na_2CO_3$ (2N, 0.35 mL) and Pd $(PPh_3)_4$ (0.033 g, 10 mol %). The contents were flushed with nitrogen and heated at 90° C. overnight. The reaction mixture was passed through a pad of Celite and the solvent was removed in vacuo. The product 32 (0.10 g) was isolated by silica gel column using 0-45% ethyl acetate in hexanes as eluent. Calcd m/z for $C_{38}H_{46}ClFN_4O_4Si.H^+=705.3$. Found m/z=705.3.

The deprotection of the amine in this sequence is accomplished analogously to Procedure M as follows:

Compound 32 (0.045 g, 0.0637 mmol) was dissolved in 2 mL of dichloromethane and treated with trifluoroacetic acid (0.5 mL) at 0° C. The reaction was stirred for 3 h. The reaction was purified by prep TLC using 10% methanol in dichloromethane as eluent to give 25 mg of the desired piperidine 33 as a white solid. Calcd m/z for $C_{27}H_{24}ClFN_4O.H^+=475.2$. Found m/z=475.1.

The piperidine nitrogen was alkylated in this sequence analogously to Procedure N as follows:

To a solution of compound 33 (0.01 g, 0.02 mmol) in 1 mL of dichloromethane was added cyclopropane carboxaldehyde (0.014 g, 0.2 mmol) followed by $NaCHBH_3$ (0.013 g, 3eq). The reaction mixture was stirred for 3 h and directly applied to a prep TLC plate. Elution with 5% methanol in dichloromethane afforded 0.004 g compound 34A as a oil. Calcd m/z for $C_{31}H_{30}ClFN_4O.H^+=529.2$. Found m/z=529.1.

The following compounds were prepared using analogous methods:

| Cpd. # | Structure | Formula (M + 1)$^+$ | calcd m/z | obsd m/z |
|---|---|---|---|---|
| 34A | 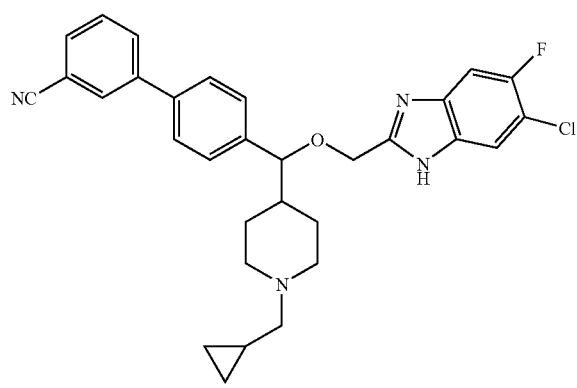 | $C_{31}H_{30}ClFN_4O•H^+$ | 529.2 | 529.1 |

| Cpd. # | Structure | Formula (M + 1)+ | calcd m/z | obsd m/z |
|---|---|---|---|---|
| 34B | 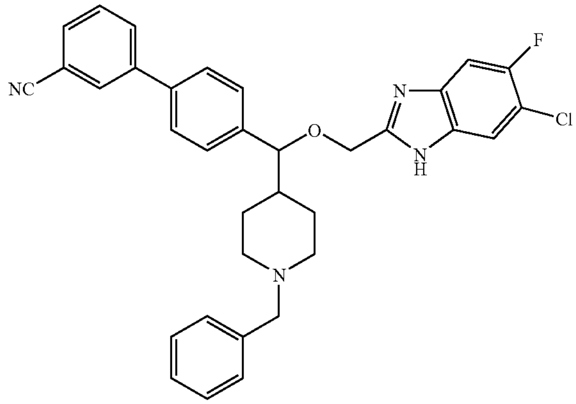 | $C_{34}H_{30}ClFN_4O \cdot H^+$ | 565.2 | 565.1 |
| 34C | 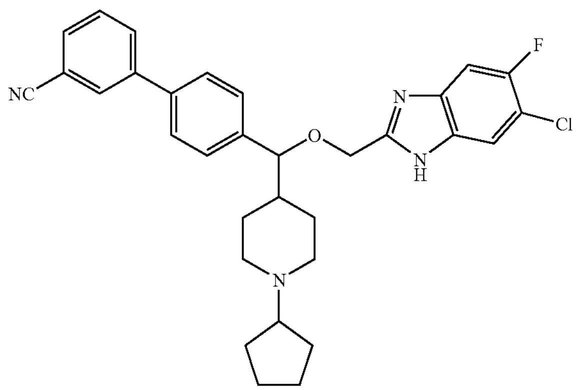 | $C_{32}H_{32}ClFN_4O \cdot H^+$ | 543.2 | 543.1 |
| 34D | 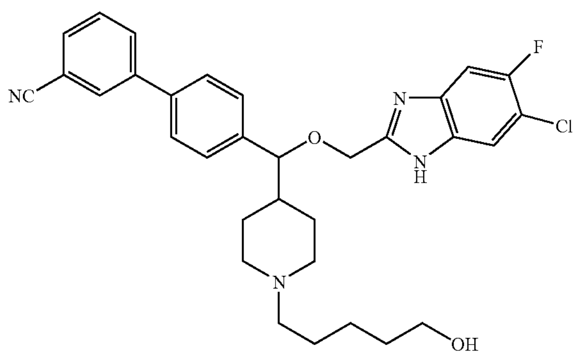 | $C_{32}H_{34}ClFN_4O_2 \cdot H^+$ | 561.2 | 561.1 |

Procedure Y:

The bromophenyl piperidine ketone from step 1 of procedure J (0.12 g, 0.33 mmol) was treated with methanesulfonyl chloride (0.038 mL, 1.5 eq) and diisopropylethyl amine (0.11 mL, 20 eq) in 1 mL of dichloromethane. The reaction mixture was stirred at 0° C. for 2 hours, warmed to room temperature and stirred overnight. The solvent was removed in vacuo and the residue was purified by silica gel column chromatography eluting with 40% ethyl acetate in hexane to give 0.058 g of compound 35 as a white solid. Calcd m/z for $C_{13}H_{16}BrNO_3S$ $H^+$=346.0. Found m/z=346.1.

Compound 35 (0.1 g, 0.29 mmol) was arylated using the Suzuki conditions described in procedure K to give 0.08 g of compound 36 as light brown solid. Calcd m/z for $C_{20}H_{20}N_2O_3S$ $H^+$=369.1. Found m/z=369.1.

Compound 36 (0.08 g, 0.22 mmol) was reduced to the corresponding alcohol according to procedure W to give 0.07 g of compound 37 as a white solid. Calcd m/z for $C_{20}H_{22}N_2O_3S$ $H^+$=371.1. Found m/z=371.1.

Compound 37 (0.035 g, 0.0945 mmol) was treated with 5,6-dichloro-2-chloromethyl-1-(2-trimethylsilanyl-ethoxymethyl)-1H-benzimidazole (0.07 g, 2 eq.) according to procedure X to afford 35 mg of compound 38 as oil. Calcd m/z for $C_{34}H_{40}Cl_2N_4O_4SSi$ $H^+$=699.2. Found m/z=699.2.

Compound 38 (0.035 g, 0.05 mmol) was deprotected according to procedure M to give 20 mg of compound 39 as oil. Calcd m/z for $C_{28}H_{26}Cl_2N_4O_3S$ $H^+$=569.1. Found m/z=569.1.

Procedure Z:

The bromophenyl piperidine ketone from step 1 of procedure J (0.10 g, 0.37 mmol) was treated with acetic anhydride (0.12 mL, 3 eq) in 2 mL of pyridine. The reaction mixture was stirred for 2 hours at room temperature. The solvent was removed in vacuo and the residue was purified by silica gel column chromatography eluting with 10% ethyl acetate in hexane to give 0.12 g of compound 40 as solid. Calcd m/z for $C_{14}H_{16}BrNO_2H^+$=310.04. Found m/z=310.1.

Compound 40 (0.12 g, 0.39 mmol) was arylated using the Suzuki conditions described in procedure K to give 0.123 g of compound 41 as brown solid. Calcd m/z for $C_{21}H_{20}N_2O_3H^+$=333.2. Found m/z=333.1.

Compound 41 (0.123 g, 0.37 mmol) was reduced to the corresponding alcohol according to procedure W to give 0.12 g of compound 42 as white solid. Calcd m/z for $C_{21}H_{22}N_2O_2H^+$=335.2. Found m/z=335.1.

Compound 42 (0.007 g, 0.02 mmol) was treated with 5,6-dichloro-2-chloromethyl-1-(2-trimethylsilanyl-ethoxymethyl)-1H-benzimidazole (0.02 g, 0.054 mmol) according to procedure X to afford 12 mg of compound 43 as oil. Calcd m/z for $C_{35}H_{40}Cl_2N_4O_3Si\ H^+$=663.2. Found m/z=663.1.

Compound 43 (0.012 g, 0.018 mmol) was deprotected according to procedure M to give 8 mg of compound 44 as oil. Calcd m/z for $C_{29}H_{26}Cl_2N_4O_2\ H^+$=533.1. Found m/z=533.1.

Compound 45 (0.5 g, 1.3 mmol) was arylated using the Suzuki conditions described in procedure K to give 0.43 g of compound 46 as oil. Calcd m/z for $C_{25}H_{30}N_2O_3\ H^+$=407.2. Found m/z=407.1.

To a mixture of compound 46 (0.43 g, 1.05 mmol), 6-Chloro-5-fluorobenzimidazole-2-thiol (0.22 g, 1.08 mmol) and triphenylphosphine (0.3 g, 1.14 mmol) in 10 mL of tetrahydrofuran (10 mL) was added a solution of diethylazodicarboxylate (0.2 g, 1.114 mmol in 5 mL tetrahydrofuran) and the mixture was stirred at room temperature for 6 hours. The solvent was removed in vacuo and the residue was purified by silica gel column chromatography using 20% ethyl acetate in hexane to give 0.05 g of compound 47 as oil. Calcd m/z for $C_{32}H_{32}ClFN_4O_2S\ H^+$=590.2. Found m/z=590.1.

Compound 47 (0.02 g, 0.0338 mmol) was deprotected according to procedure M to give 6 mg of compound 48 as white solid. Calcd m/z for $C_{27}H_{24}ClFN_4S\ H^+$=491.5. Found m/z=491.1.

Preparation of 4-(4-Bromo-phenyl)-4-hydroxymethyl-piperidine-1-carboxylic acid tert-butyl ester, 49:

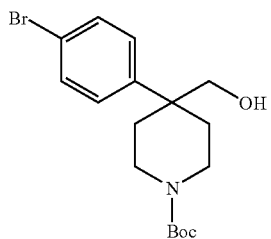

49

Step 1:

To a suspension of bis-(2-chloroethyl)amine hydrochloride (17.85 g, 100 mmol, 1 eq) in 100 mL of dichloromethane was added 100 mL of a 10% aqueous solution of NaOH. The mixture was stirred at room temperature and a solution of (Boc)$_2$O (21.82 g, 100 mmol, 1 eq) in 100 mL of dichloromethane was added. The reaction was stirred at room temperature for 20 h and then extracted with 100 mL of dichloromethane. The organic extracts were combined and dried over Na$_2$SO$_4$, filtered and concentrated by rotary evaporation to give the crude bis-(2-chloroethyl)carbamic acid tert-butyl ester (24.1 g), which was used in the next step without further purification.

Step 2:

To a mixture of bis-(2-chloro-ethyl)-carbamic acid tert-butyl ester from Step 1 (7.26 g, 30 mmol, 1 eq) and 4-bromophenylacetonitrile (5.88 g, 30 mmol, 1 eq) in 38 mL of toluene and 76 mL of H$_2$O was added NaOH (45.6 g, 114 mmol, 10M solution) followed by hexadecyltributylphosphonium bromide (3.0 g, 6.0 mmol, 0.2 eq). The resulting dark mixture was heated to 110° C. for 2 h and then allowed to cool to ambient temperature. It was extracted with three 200 mL portions of ethyl acetate and the combined organic extracts were dried over Na$_2$SO$_4$, filtered and concentrated by rotary evaporation to give the crude product as a black oily residue. Purification by flash column chromatography eluting with a gradient of 5-10% ethyl acetate in hexane gave 5.67 g of 4-(4-bromo-phenyl)-4-cyano-piperidine-1-carboxylic acid tert-butyl ester as a pale yellow foam. $^1$H NMR (300 MHz, CDCl$_3$): δ 7.56-7.48 (d, 2H), 7.36-7.30(d, 2H), 4.40-4.10 (br. s, 2H), 3.27-3.05 (t, 2H), 2.10-1.80 (m, 4H), 1.45 (s, 9H).

Step 3:

To a solution of 4-(4-bromo-phenyl)-4-cyano-piperidine-1-carboxylic acid tert-butyl ester from Step 2 (5.67 g, 15.57 mmol, 1 eq) in 60 mL of dichloromethane was add a solution of DIBAL-H (1M in toluene, 23.36 mL, 23.36 mmol, 1.5 eq) in a drop-wise fashion. The resulting mixture was stirred at room temperature for 20 h and then 15 mL of methanol was added carefully. The mixture was stirred for 0.25 h and a precipitate formed. The resulting mixture was filtered through Celite and the salts were washed several times with ethyl acetate. The filtrate was adsorbed onto silica gel and purified by flash column chromatography eluting with a gradient of 5-20% ethyl acetate in hexane to give 1.78 g of 4-(4-bromo-phenyl)-4-(2-oxo-ethyl)-piperidine-1-carboxylic acid tert-butyl ester and 1.54 g of recovered starting material. $^1$H NMR (300 MHz, CDCl$_3$): δ 9.35 (s, 1H), 7.50-7.46 (d, 2H), 7.15-7.10 (d, 2H), 3.82 (br. s, 2H), 3.11-3.04 (t, 2H), 2.35-2.28 (dt, 2H), 1.90 (br. s, 2H), 1.42 (s, 9H).

Step 4:

To a solution of 1.78 g of 4-(4-bromo-phenyl)-4-hydroxymethyl-piperidine-1-carboxylic acid tert-butyl ester from Step 3 (4.85 mmol, 1 eq) in 25 mL of isopropanol was added NaBH$_4$ (0.201 g, 5.33 mmol, 1.1 eq). The mixture was stirred at room temperature for 20 h and then quenched by the addition of aqueous HCl (20 mL) to pH ~3. The solvent was removed by rotary evaporation and the resulting aqueous mixture was extracted with three 50 mL portions of ethyl acetate. The organic extracts were combined and washed with saturated brine and dried over Na$_2$SO$_4$. Filtration and concentration by rotary evaporation gave the crude product which was purified by flash column chromatography eluting with a gradient of 5-20% ethyl acetate in hexane to give 1.36 g of the title compound 4-(4-bromo-phenyl)-4-hydroxymethyl-piperidine-1-carboxylic acid tert-butyl ester 49 as a pale foam. $^1$H NMR (300 MHz, CDCl$_3$): δ 7.38-7.18 (m, 4H), 4.35-4.19 (br. d, 2H), 2.83-2.76 (t, 2H), 2.70-2.58 (m, 1H), 1.86-1.78 (d, 2H), 1.70-1.58 (m, 3H), 1.50 (s, 9H).

Preparation of 2,5,6-Trichloro-1-(2-trimethylsilanyl-ethoxymethyl)-1H-benzoimidazole, 50

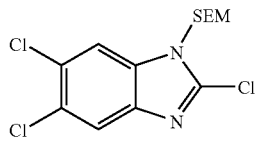

Step 1:

To a solution of 3,4-dichlorophenylenediamine (1.5 g, 8.2 mmol, 1 eq) in 15 mL of tetrahydrofuran was added CO(imid)$_2$ (2.0 g, 12.3 mmol, 1.5 eq). The mixture was stirred at room temperature for 16 h under Argon. The solvent was removed by rotary evaporation and the residue partitioned between 85 mL of ether and 85 mL of 1N NaOH. The aqueous extract was acidified by careful addition of concentrated HCl and the resulting off-white precipitate was filtered, washed with water, then dried under high vacuum to give the crude product. To this material was added 40 mL of POCl$_3$ and the mixture was heated to 120° C. for 2 h. The POCl$_3$ was removed by rotary evaporation and the residue was diluted with 45 mL of water and neutralized by addition of aqueous KHCO$_3$. The aqueous mixture was extracted with three 100 mL portions of 90/10 (v:v) dichloromethane in methanol. The organic extracts were combined and dried over Na$_2$SO$_4$, filtered and concentrated by rotary evaporation to give 2,5,6-trichloro-1H-benzoimidazole as a yellow solid (1.0 g). $^1$H NMR (300 MHz, DMSO): δ 7.82 (s, 2H); MS (ESI): m/z 223.4/225.3 (M+1/M+3).

Step 2:

To a solution of 4.1 g crude 2,5,6-trichloro-1H-benzoimidazole from Step 1 (~18.7 mmol) in 60 mL of tetrahydrofuran under Argon at 0° C. was added diisopropylethyl amine (0.91 mL, 22.44 mmol, 1.2 eq). To this mixture was added SEM-Cl (4.91 mL, 28 mmol, 1.5 eq) in a drop-wise fashion and the mixture was stirred at room temperature for 20 h. Methanol was added (20 mL) and the solvent removed by rotary evaporation. The crude residue was dissolved in dichloromethane, absorbed onto silica gel, and purified by flash column chromatography eluting with 30% ethyl acetate in hexane to give 4.25 g of the title compound 2,5,6-trichloro-1-(2-trimethyl-silanyl-ethoxymethyl)-1H-benzoimidazole, 50 as an off-white solid. $^1$H NMR (300 MHz, DMSO): δ 8.11 (s, 1H), 7.96 (s, 1H), 5.64 (s, 2H), 3.58-3.53 (d, 2H), 0.85-0.80 (t, 2H), 0.03-0.01 (s, 9H).

Procedure AA:

To a solution of 0.075 g of 4-(4-bromo-phenyl)-4-hydroxymethyl-piperidine-1-carboxylic acid tert-butyl ester, 49 (0.18 mmol) in 0.6 mL of DMF at room temperature was added 0.095 g of NaH (0.22 mmol, 1.2 eq). The mixture was stirred at room temperature for 1 h followed by the addition of a 1 mL DMF solution containing 0.070 g of 2,5,6-trichloro-1-(2-trimethylsilanyl-ethoxymethyl)-1H-benzoimidazole 50 (0.198 mmol, 1 eq), 0.020 g of n-Bu$_4$NI (0.054 mmol, 0.3 eq) and 0.012 g of 15-crown-5 (0.054 mmol, 0.3 eq). The resulting mixture was stirred and heated at 50° C. for 20 h. After cooling, the mixture was diluted with 25 mL of ethyl acetate and washed with H$_2$O and saturated brine. The organic extracts were dried over Na$_2$SO$_4$, filtered and concentrated by rotary evaporation to give the crude product which was purified by flash column chromatography eluting with a gradient of 7-20% ethyl acetate in hexane to give 0.105 g of 4-(4-bromo-phenyl)-4-[5,6-dichloro-1-(2-trimethylsilanyl-ethoxymethyl)-1H-benzoimidazol-2-yloxymethyl]-piperidine-1-carboxylic acid tert-butyl ester 51 as a pale foam (0.144 mmol, 80%). $^1$H NMR (300 MHz, CDCl$_3$): δ 7.62-7.59 (m, 2H, 7.41 (m, 1H), 7.26-7.21 (m, 1H), 7.10-7.07 (d 2H), 5.07 (s, 2H), 4.41 (s, 2H), 3.67 (m, 2H), 3.58 (m, 2H), 3.29-3.23 (m, 2H), 2.17-2.13 (m, 2H), 1.86-1.83 (m, 2H), 1.34 (s, 9H), 0.78-0.71 (m, 2H), 0.11 (s, 9H).

Compound 51 was arylated using Suzuki conditions as described in Procedure K as follows:

A mixture of 0.105 g of 4-(4-bromo-phenyl)-4-[5,6-dichloro-1-(2-trimethylsilanyl-ethoxymethyl)-1H-benzoimidazol-2-yloxymethyl]-piperidine-1-carboxylic acid tert-butyl ester 51 (0.144 mmol, 1 eq), 0.024 g of 3-cyanophenyl boronic acid (0.16 mmol, 1.1 eq), and 0.034 g of Pd(PPh$_3$)$_4$ (0.03 mmol, 20 mol %) was mixed with 3 mL of toluene, 2 mL of ethanol and 1 mL of 2M aqueous Na$_2$CO$_3$ and then heated at 80° C. for 20 h while stirring. The reaction was allowed to cool to room temperature, diluted with 25 mL of ethyl acetate and washed with 25 mL of saturated brine. The organic extracts were dried over Na$_2$SO$_4$, filtered and concentrated by rotary evaporation to give the crude product which was purified by flash column chromatography eluting with a gradient of 5-20% ethyl acetate in hexane to give 0.081 g of 4-(3'-cyano-biphenyl-4-yl)-4-[5,6-dichloro-1-(2-trimethylsilanyl-ethoxymethyl)-1H-benzoimidazol-2-yloxymethyl]-piperidine-1-carboxylic acid tert-butyl ester 52 as a pale foam: $^1$H NMR (300 MHz, CDCl$_3$): δ 7.82-7.76 (m, 2H), 7.59-7.48 (m, 7H), 7.13-7.10 (m, 1H), 5.17 (s, 2H), 4.53 (s, 2H), 3.85-3.80 (br. d, 2H), 3.41-3.36 (t, 2H), 3.18-3.10 (t, 2H), 2.36-2.3 (d, 2H), 2.00-1.96 (t, 2H), 1.44 (s, 9H), 0.83-0.77 (t, 2H), 0.10 (s, 9H).

Procedure AB:

To a solution of 0.081 g of 4-(3'-cyano-biphenyl-4-yl)-4-[5,6-dichloro-1-(2-trimethylsilanyl-ethoxymethyl)-1H-benzoimidazol-2-yloxymethyl]-piperidine-1-carboxylic acid tert-butyl ester 52 (0.115 mmol) in 5 mL of tetrahydrofuran at room temperature was added 0.23 mL of a solution of TBAF (1M in THF, 0.23 mmol, 2 eq). The mixture was heated at 60° C. for 6 h. After cooling to room temperature, the mixture was partitioned between 15 mL of ethyl acetate and 15 mL of H$_2$O. The organic layer was separated, washed with saturated brine, dried (Na$_2$SO$_4$), and concentrated by rotary evaporation to give the crude product as a pale foam (0.070 g) which was purified by flash column chromatography eluting with 30% ethyl acetate in hexanes to give 0.035 g of 4-(3'-cyano-biphenyl-4-yl)-4-(5,6-dichloro-1H-benzoimidazol-2-yloxymethyl)-piperidine-1-carboxylic acid tert-butyl ester 53 as a pale foam and 0.024 g of recovered starting material. $^1$H NMR (300 MHz, CDCl$_3$): δ 7.82-7.75 (m, 2H), 7.64-7.52 (dt, 1H), 7.61-7.46 (m, 5H), 7.26 (s, 1H), 4.51 (s, 2H), 3.85-3.83 (d, 2H), 3.18-3.10 (t, 2H), 2.32-2.28 (d, 2H), 2.04-1.98 (t, 2H), 1.42 (s, 9H). MS (ESI): Calcd m/z for C$_{31}$H$_{30}$Cl$_2$N$_4$O$_3$.H$^+$=577.2. Found m/z=576.7/578.7 [(M+1)$^+$/(M+3)$^+$].

4'-[4-(5,6-Dichloro-1H-benzoimidazol-2-yloxymethyl)-piperidin-4-yl]-biphenyl-3-carbonitrile, 54 was prepared analogously to Procedure M as follows

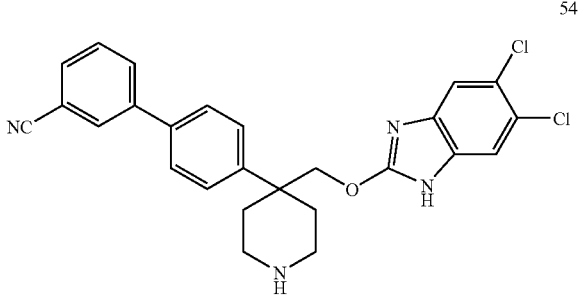

54

To a solution of 0.015 g of 4-(3'-cyano-biphenyl-4-yl)-4-(5,6-dichloro-1H-benzoimidazol-2-yloxymethyl)-piperidine-1-carboxylic acid tert-butyl ester 53 (0.026 mmol) in 3 mL of dichloromethane at 0° C. was added 1 mL of trifluoroacetic acid. The mixture was stirred at 0° C. for 2 h then diluted with 10 mL of toluene and concentrated by rotary evaporation. The resulting residue was dissolved in 25 m) of ethyl acetate and washed with 10% aqueous NaHCO$_3$ and saturated brine. The organic extracts were dried over Na$_2$SO$_4$, filtered and concentrated by rotary evaporation to give the crude product which was purified by reverse phase preparative HPLC to give 0.0113 g of the desired product 4'-[4-(5,6-dichloro-1H-benzoimidazol-2-yloxymethyl)-piperidin-4-yl]-biphenyl-3-carbonitrile 54 as a pale foam. $^1$H NMR (300 MHz, CDCl$_3$/CD$_3$OD): δ 7.85-7.75 (t, 1H), 7.72-7.70 (dt, 1H), 7.57-7.41 (m, 6H), 7.30(s, 2H), 5.19 (s, 2H), 4.31 (s, 2H), 3.33-3.25 (m, 2H), 2.90-2.82 (d, 2H), 2.47-2.34 (m, 2H), MS (ESI): Calcd m/z for C$_{26}$H$_{22}$Cl$_2$N$_4$O.H$^+$=477.1. Found m/z=476.7/478.7 [(M+1)$^+$/(M+3)$^+$].

4'-[4-(5,6-Dichloro-1H-benzoimidazol-2-yloxymethyl)-1-methanesulfonyl-piperidin-4-yl]-biphenyl-3-carbonitrile, 56

56

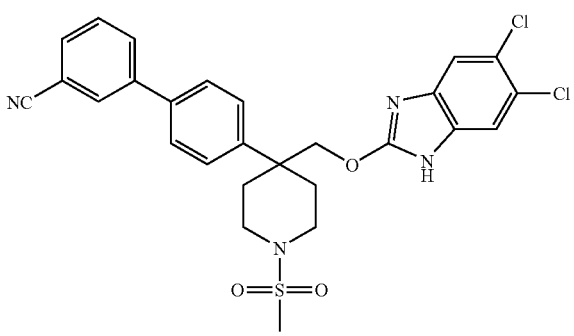

Step 1:

To a solution of 0.035 g of 4-(3'-cyano-biphenyl-4-yl)-4-[5,6-dichloro-1-(2-trimethylsilanyl-ethoxymethyl)-1H-benzoimidazol-2-ylmethoxymethyl]-piperidine-1-carboxylic acid tert-butyl ester 52 (0.05 mmol) in 3 mL of dichloromethane at 0° C. was added 1 mL of trifluoroacetic acid as per Procedure M. The mixture was stirred at 0° C. for 2 h then diluted with 10 mL of toluene and concentrated by rotary evaporation. The resulting residue was dissolved in 25 mL of ethyl acetate, washed with 10% aqueous NaHCO$_3$ and saturated brine, dried (Na$_2$SO$_4$), and concentrated by rotary evaporation to give the crude product which was purified by reverse phase preparative HPLC to give 0.030 g of 4'-{4-[5,6-dichloro-1-(2-trimethylsilanyl-ethoxymethyl)-1H-benzoimidazol-2-yloxymethyl]-piperidin-4-yl}-biphenyl-3-carbonitrile 55 as a pale foam. $^1$H NMR (300 MHz, CDCl$_3$): δ 7.85-7.84 (t, 1H), 7.80-7.77 (d, 1H), 7.63-7.51 (m, 7H), 7.33 (s, 1H), 5.19 (s, 2H), 4.54 (s, 2H), 3.41-3.36 (t, 2H), 3.12-3.05 (d, 2H), 2.92-2.82 (t, 2H), 2.60 (br. s, 1H), 2.40-2.33 (d, 2H), 2.14-2.05 (t, 2H), 0.00 (s, 9H).

Step 2:

To a solution of 0.030 g of 4'-{4-[5,6-dichloro-1-(2-trimethylsilanyl-ethoxymethyl)-1H-benzoimidazol-2-yloxymethyl]-piperidin-4-yl}-biphenyl-3-carbonitrile (0.05 mmol) 55 in 1 mL of dichloromethane was added methanesulfonyl chloride (0.005 mL, 0.053 mmol, 1.1 eq) and DIEA (0.011 mL, 0.06 mmol, 1.2 eq). The resulting mixture was stirred at room temperature for 16 h, diluted with 5 mL of ethyl acetate, and washed with H$_2$O and saturated brine. The organic extracts were combined and dried over Na$_2$SO$_4$, filtered and concentrated by rotary evaporation to give 0.044 g of 4'-{4-[5,6-dichloro-1-(2-trimethylsilanyl-ethoxymethyl)-1H-benzoimidazol-2-yloxymethyl]-1-methanesulfonyl-piperidin-4-yl}-biphenyl-3-carbonitrile as a pale foam. MS (ESI): m/z 684.8/686.8 (M+1/M+3).

Step 3:

To a solution of 0.044 g of crude 4'-{4-[5,6-dichloro-1-(2-trimethylsilanyl-ethoxymethyl)-1H-benzoimidazol-2-yloxymethyl]-1-methanesulfonyl-piperidin-4-yl}-biphenyl-3-carbonitrile from the previous step (~0.05 mmol) in 2 mL of tetrahydrofuran was added tetrabutylammonium fluoride (1M in THF, 0.1 mL, 0.1 mmol, 2 eq) and the resulting mixture was heated to 60° C. for 18 h. After cooling to room temperature, the reaction mixture was diluted with 10 mL of ethyl acetate and washed with H$_2$O and saturated brine. The organic extracts were combined and dried over Na$_2$SO$_4$, filtered and concentrated by rotary evaporation to give the crude product as a pale foam. Purification by flash silica gel chromatography eluting with a gradient of 20-70% ethyl acetate in hexane gave a pale foam which was re-purified by reverse phase preparative HPLC to yield 0.016 g of the desired product 4'-[4-(5,6-dichloro-1H-benzoimidazol-2-yloxymethyl)-1-methanesulfonyl-piperidin-4-yl]-biphenyl-3-carbonitrile 56 as a white foam. $^1$H NMR (300 MHz, CDCl$_3$): δ 7.84-7.83 (t, 1H), 7.80-7.77 (dt, 1H), 7.66-7.44 (m, 8H), 4.54 (s, 2H), 3.64-3.40 (d, 2H), 3.02-2.95 (t, 2H), 2.74 (s, 3H), 2.60 (br. s, 1H), 2.47-2.43 (d, 2H), 2.22-2.12 (t, 2H). MS (ESI): Calcd m/z for C$_{27}$H$_{24}$Cl$_2$N$_4$O$_3$S.H$^+$=554.1. Found m/z=554.6/556.7 [(M+1)$^+$/(M+3)$^+$].

4'-[1-Cyclopropylmethyl-4-(5,6-dichloro-1H-benzoimidazol-2-yloxymethyl)-piperidin-4-yl]-biphenyl-3-carbonitrile, 57

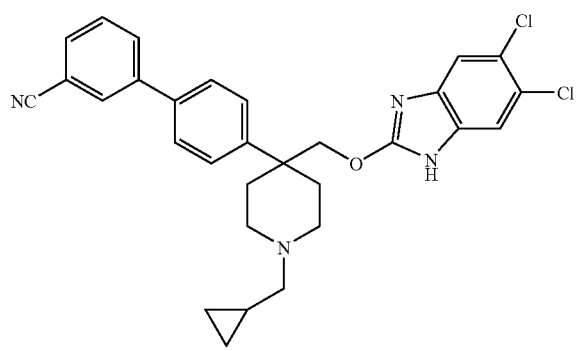

Compound 57 was prepared analogously to procedure H as follows:

To a solution of 0.045 g of 4'-{4-[5,6-dichloro-1-(2-trimethylsilanyl-ethoxymethyl)-1H-benzoimidazol-2-yloxymethyl]-piperidin-4-yl}-biphenyl-3-carbonitrile 55 (0.073 mmol, 1 eq) in 0.5 mL of 1,2-dichloroethane at room temperature was added 6.6 µL of cyclopropanecarboxaldehyde (0.088 mmol, 1.2 eq) and acetic acid (0.005 mL, 1% v/v). The mixture was stirred at room temperature for 1 h followed by the addition of 0.023 g of NaBH(OAc)$_3$ (0.105 mmol, 1.5 eq). The reaction was stirred at room temperature for 16 h and then the solvent was removed by rotary evaporation to yield 0.052 g of the crude product. This intermediate was dissolved in 2 mL of tetrahydrofuran and tetrabutylammonium fluoride on silica gel (1.0-1.5 mmol/g, 0.16 g, 2 eq) was added. The mixture was heated at 60° C. for 16 h then filtered and the resin washed with 10 mL of tetrahydrofuran. The filtrate was concentrated by rotary evaporation and the crude product was purified by flash silica gel chromatography eluting with 1% methanol in dichloromethane with 3% triethylamine to give 0.007 g of the desired product 4'-[1-cyclopropylmethyl-4-(5,6-dichloro-1H-benzoimidazol-2-yloxymethyl)-piperidin-4-yl]-biphenyl-3-carbonitrile 57 MS (ESI): Calcd m/z for $C_{30}H_{28}Cl_2N_4O.H^+$=531.2. Found m/z 530.9/532.9 [(M+1)$^+$/(M+3)$^+$].

4-(3'-Cyano-biphenyl-4-yl)-4-(5,6-dichloro-1H-benzoimidazol-2-yloxymethyl)-piperidine-1-carboxylic acid ethylamide, 58

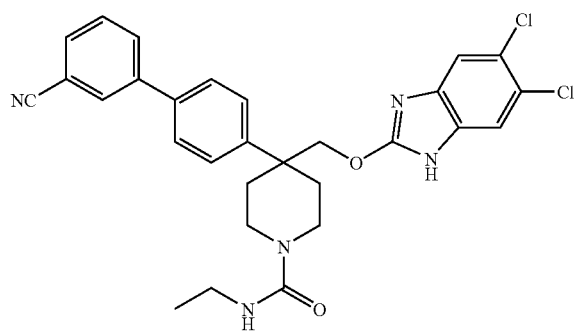

To a solution of 0.045 g of 4'-{4-[5,6-dichloro-1-(2-trimethylsilanyl-ethoxymethyl)-1H-benzoimidazol-2-yloxymethyl]-piperidin-4-yl}-biphenyl-3-carbonitrile (0.073 mmol, 1 eq) in 0.7 mL of dichloromethane was added ethyl isocyanate (6.5 µL, 0.088 mmol, 1.2 eq) and 15.4 µL of diisopropylethyl amine (0.088 mmol, 1.2 eq) and the resulting mixture was stirred at room temperature for 16 h. The solvent was removed by rotary evaporation to yield the crude product which was purified by preparative TLC eluting with 10% methanol in dichloromwthane to give 0.030 g of 4-(3'-cyano-biphenyl-4-yl)-4-[5,6-dichloro-1-(2-trimethylsilanyl-ethoxymethyl)-1H-benzoimidazol-2-yloxymethyl]-piperidine-1-carboxylic acid ethylamide. This intermediate was dissolved in 2 mL of tetrahydrofuran and 0.080 g of tetrabutylammonium fluoride on silica gel (1.0-1.5 mmol/g, 2 eq) was added. The mixture was heated at 60° C. for 16 h then filtered and the resin washed with 10 mL of tetrahydrofuran. The filtrate was concentrated by rotary evaporation and the crude product was purified by flash silica gel chromatography eluting with 1% methanol in dichloromethane with 3% triethylamine to give 0.0054 g of the desired product 4-(3'-cyano-biphenyl-4-yl)-4-(5,6-dichloro-1H-benzoimidazol-2-yloxymethyl)-piperidine-1-carboxylic acid ethylamide 58. MS (ESI): Calcd m/z for $C_{29}H_{27}Cl_2N_5O_2.H^+$=548.2; found m/z=547.8/549.8 [(M+1)$^+$/(M+3)$^+$].

4-(4-Bromo-phenyl)-4-hydroxy-piperidine-1-carboxylic acid tert-butyl ester, 59

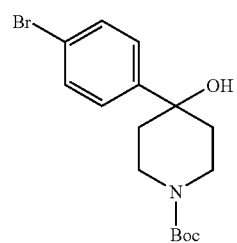

Compound 59 was prepared using procedure S as follows:

To a solution of 5 g of 4-(4-bromophenyl)-4 hydroxy-piperidine (19.52 mmol, 1 eq) in 60 mL of 10% triethylamine in DMF at 0° C. was added (Boc)$_2$O (4.26 g, 19.52 mmol, 1 eq). The mixture was stirred at room temperature for 16 h and then concentrated by rotary evaporation. The resulting slurry was dissolved in 100 mL of ethyl acetate, washed with 1N aqueous HCl and dried over Na$_2$SO$_4$. Filtration and concentration by rotary evaporation gave 7.0 g of the desired 4-(4-bromo-phenyl)-4-hydroxy-piperidine-1-carboxylic acid tert-butyl ester 59 (19.5 mmol, 100%). $^1$H NMR (300 MHz, CDCl$_3$): δ 7.46-7.42 (d, 2H), 7.35-7.31 (d, 2H), 4.00-3.90 (br. d, 2H), 3.22-3.16 (br. t, 2H), 2.34 (br. s, 1H), 1.98-1.80 (br. t, 2H), 1.69-1.64 (br d, 2H), 1.44 (s, 9H).

2-Chloromethyl-5,6-difluoro-1-(2-trimethylsilanyl-ethoxymethyl)-1H-benzoimidazole, 60

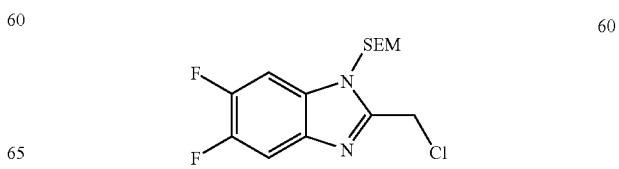

Step 1:

A mixture of 1 g of 3,4-difluoro-1,2-phenylenediamine (6.94 mmol) and 0.983 g of chloro-acetic acid (10.41 mmol, 1.5 eq) in 13 mL of 4N aqueous HCl was heated to 100° C. for 3 h. The mixture was poured onto ice (10 g), neutralized by the addition of NH$_4$OH and extracted with three 30 mL portions of ethyl acetate. The organic extracts were combined and dried over Na$_2$SO$_4$, filtered and concentrated by rotary evaporation to give 1.28 g of 2-chloromethyl-5,6-difluoro-1H-benzoimidazole as a brown solid. $^1$H NMR (300 MHz, CDCl$_3$/CD$_3$OD): δ 7.30-7.25 (m, 2H), 4.68 (s, 2H); MS (ESI): Calcd m/z for C$_8$H$_5$ClF$_2$N$_2$.H$^+$=203.1. Found m/z=203.2/205.2 [(M+1)$^+$/(M+3)$^+$].

Step 2:

To a solution of 1.28 g of the crude 2-chloromethyl-5,6-difluoro-1H-benzoimidazole (~6.34 mmol, 1 eq) in 8 mL of tetrahydrofuran at 0° C. was added 1.33 mL of diisopropyl-ethyl amine (7.61 mmol, 1.2 eq) followed by 1.68 mL of SEM-Cl (9.51 mmol, 1.5 eq). The resulting mixture was stirred and warmed to room temperature over 18 h. The reaction was diluted with 25 mL of ethyl acetate and washed with 20 mL of saturated brine and 20 mL of 1N aqueous HCl. The organic extracts were dried over Na$_2$SO$_4$, filtered and concentrated by rotary evaporation to give 2.3 g of 2-chloromethyl-5,6-difluoro-1-(2-trimethylsilanyl-ethoxymethyl)-1H-benzoimidazole 60. $^1$H NMR (300 MHz, CDCl$_3$): δ 7.85 (s, 1H), 7.61 (s, 1H), 5.57 (s, 2H), 4.84 (s, 2H), 3.58-3.52 (t, 2H), 0.95-0.89 (t, 2H), 0.04 (s, 9H).

4-(3'-Cyano-biphenyl-4-yl)-4-(5,6-difluoro-1H-benzoimidazol-2-ylmethoxy)-piperidine-1-carboxylic acid tert-butyl ester, 63

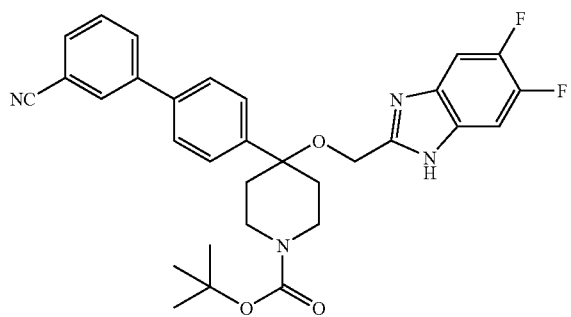

63

Step 1:

Compound 59 was alkylated as per procedure X as follows:

To a suspension of 0.325 g of KH (30% dispersion in mineral oil, 2.43 mmol, 1.2 eq) in 3 mL of tetrahydrofuran at 0° C. was added a solution of 4-(4-bromo-phenyl)-4-hydroxy-piperidine-1-carboxylic acid tert-butyl ester 59 (0.75 g, 2.025 mmol, 1 eq) in 3 mL of tetrahydrofuran. The resulting mixture was stirred for 0.5 h followed by the addition of a solution of 0.874 g of 2-chloromethyl-5,6-difluoro-1-(2-trimethylsilanyl-ethoxymethyl)-1H-benzoimidazole 60 (2.63 mmol, 1.3 eq) in 3 mL of tetrahydrofuran. The reaction mixture was stirred at 0° C. for 0.5 h and then at room temperature for 18 h. The mixture was partitioned between 25 mL of ethyl acetate and 25 mL of H$_2$O, the organic layer separated, and the aqueous layer extracted with two 25 mL portions of ethyl acetate. The combined organic extracts were washed with 25 mL of saturated brine, dried (Na$_2$SO$_4$), and concentrated to give the crude product which was purified by flash silica gel chromatography eluting with 1% methanol in dichloromethane followed by a second chromatography eluting with 35% ethyl acetate in hexane to give 0.116 g of the desired product 4-(4-bromo-phenyl)-4-[5,6-difluoro-1-(2-trimethylsilanyl-ethoxymethyl)-1H-benzoimidazol-2-ylmethoxy]-piperidine-1-carboxylic acid tert-butyl ester 61. MS (ESI): Calcd m/z for C$_{30}$H$_{40}$BrF$_2$N$_3$O$_4$Si.H$^+$=652.2. Found m/z=652.1/654.0 [(M+1)$^+$/(M+3)$^+$].

Step 2:

Compound 61 was arylated as per procedure K as follows:

A mixture of 0.116 g of 4-(4-bromo-phenyl)-4-[5,6-difluoro-1-(2-trimethylsilanyl-ethoxymethyl)-1H-benzoimidazol-2-ylmethoxy]-piperidine-1-carboxylic acid tert-butyl ester 61 (~0.18 mmol, 1 eq), 0.032 g of 3-cyanophenylboronic acid (0.215 mmol, 1.2 eq), and 0.040 g of Pd(PPh$_3$)$_4$ (0.036 mmol, 20 mol %) with 3 mL of toluene, 2 mL of ethanol and 1 mL of 2M aqueous Na$_2$CO$_3$ was heated at 80° C. for 20 h. The reaction was allowed to cool to room temperature, diluted with 25 mL of ethyl acetate and washed with 25 mL of saturated brine. The organic layer was dried over Na$_2$SO$_4$, filtered and concentrated by rotary evaporation to give the crude product which was purified by flash silica gel chromatography eluting with a gradient of 5-50% ethyl acetate in hexane to give 0.042 g of 4-(3'-cyano-biphenyl-4-yl)-4-[5,6-difluoro-1-(2-trimethylsilanyl-ethoxymethyl)-1H-benzoimidazol-2-ylmethoxy]-piperidine-1-carboxylic acid tert-butyl ester 62 as a pale foam.

Step 3:

Compound 62 was deprotected as per procedure AB as follows:

To a solution of 0.033 g of 4-(3'-cyano-biphenyl-4-yl)-4-[5,6-difluoro-1-(2-trimethylsilanyl-ethoxymethyl)-1H-benzoimidazol-2-ylmethoxy]-piperidine-1-carboxylic acid tert-butyl ester 62 (0.05 mmol, 1 eq) in 2.5 mL of tetrahydrofuran was added 0.10 mL tetrabutylammonium fluoride (1M in THF, 0.1 mmol, 2 eq). The reaction was stirred at room temperature for 20 h and then at 60° C. for 5 h. The mixture was allowed to cool to room temperature and then partitioned between 25 mL of ethyl acetate and 20 mL of H$_2$O. The organic layer was separated, washed with saturated brine, dried (Na$_2$SO$_4$), and concentrated to give the crude product which was purified by flash silica gel chromatography eluting with a gradient of 10-50% ethyl acetate in hexane to yield 0.025 g of the desired product 4-(3'-cyano-biphenyl-4-yl)-4-(5,6-difluoro-1H-benzoimidazol-2-ylmethoxy)-piperidine-1-carboxylic acid tert-butyl ester 63 as a pale foam: $^1$H NMR (300 MHz, CDCl$_3$): δ 9.96 (br. s., 1H), 7.82-7.81 (m, 1H), 7.78-7.75 (dt, 1H), 7.65-7.61 (m, 1H), 7.57-7.40 (m, 6H), 7.30-7.24 (m, 1H), 4.43 (s, 2H), 4.00 (d, 2H), 3.31-3.23 (t, 2H), 2.24-2.19 (d, 2H), 2.07-1.97 (td, 2H), 1.48 (s, 9H); MS (ESI): Calcd m/z for C$_{31}$H$_{30}$F$_2$N$_4$O$_3$.H$^+$=545.2. Found m/z=545 (M+1)$^+$.

4'-[4-(5,6-Dichloro-1H-benzoimidazol-2-yl-methoxy)-piperidin-4-yl]-biphenyl-3-carbonitrile, 64

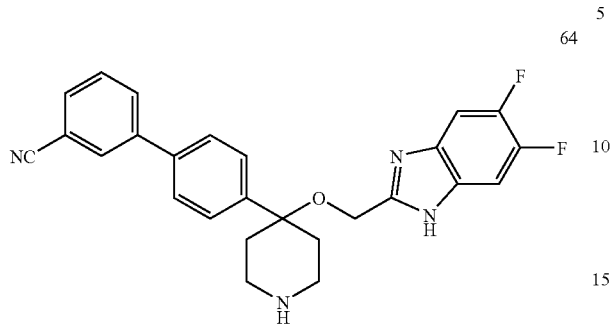

Compound 64 was prepared according to procedure M as follows:

To a solution of 0.010 g of 4-(3'-cyano-biphenyl-4-yl)-4-(5,6-difluoro-1H-benzoimidazol-2-ylmethoxy)-piperidine-1-carboxylic acid tert-butyl ester 63 (0.018 mmol) in 2 mL of dichloromethane at 0° C. was added 0.7 mL of trifluoroacetic acid in a drop-wise fashion. The reaction was stirred at 0° C. for 1 h and then at room temperature for 0.5 h. The mixture was diluted with 10 mL of toluene and concentrated using rotary evaporation. The resulting residue was partitioned between 10 mL of ethyl acetate and saturated 10 mL of aqueous NaHCO$_3$. The organic layer separated, washed with saturated 10 mL of brine, dried (Na$_2$SO$_4$), and concentrated by rotary evaporation to give 0.008 g of the desired product 4'-[4-(5,6-dichloro-1H-benzoimidazol-2-ylmethoxy)-piperidin-4-yl]-biphenyl-3-carbonitrile 64: $^1$H NMR (300 MHz, CDCl$_3$/CD$_3$OD): δ 7.81-7.74 (m, 2H), 7.63-7.49 (m, 6H), 7.37-7.28 (t, 2H), 4.32 (s, 2H), 3.30-3.19 (t, 2H), 3.09-3.00 (br. d, 2H), 2.30-2.20 (d, 2H), 2.11-2.02 (t, 2H); MS (ESI): Calcd m/z for C$_{26}$H$_{22}$F$_2$N$_4$O.H$^+$=445.2. Found m/z=445 (M+1)$^+$.

Preparation of N-linked Alkylbenzimidazoles: 4,4-Disubstituted Piperidines:

4'-{1-Cyclopentyl-4-[(5,6-dichloro-1H-benzoimidazol-2-ylmethyl)-amino]-piperidin-4-yl}-biphenyl-3-carbonitrile, 67

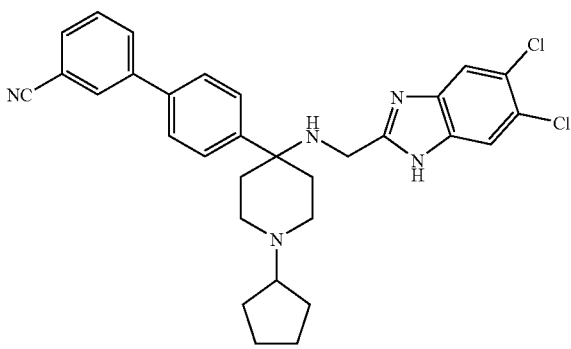

Compound 67 was prepared as per procedure L as follows:

Step 1: Preparation of alkylating agent, 66:

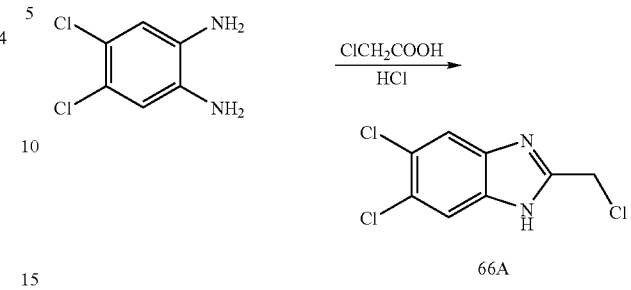

To a solution of 5 g of 4,5-dichlorobenzene-1,2-diamine (0.0282 mol) in 5N aqueous HCl (50 mL) was added 2.5 g of chloroacetic acid (0.0264 mol) and the mixture was heated under reflux overnight. The reaction mixture was cooled to 0° C. and neutralized with aq. NH$_4$OH solution. The product was collected by vacuum filtration and dried in vacuo to get 6.0 g of chloromethyl benzimidazole 66A as brown solid. Calcd m/z for C$_8$H$_5$Cl$_3$N$_2$H$^+$=234.96. Found m/z=236.1.

Step 2:

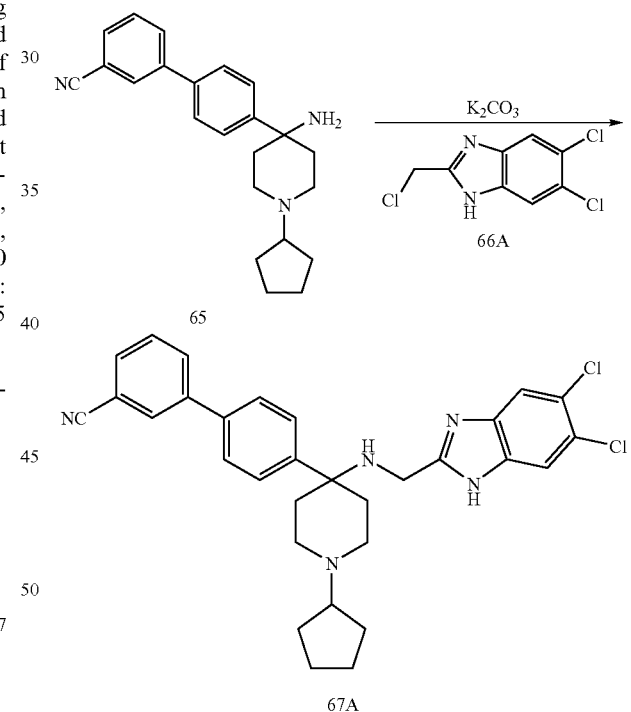

To a solution of 0.044 g of 4'-(4-amino-1-cyclopentyl-piperidin-4-yl)-biphenyl-3-carbonitrile (0.13 mmol) in 2 mL of acetonitrile was added 0.053 g of K$_2$CO$_3$ (3eq) followed by 0.045 g of 5,6-dichloro-2-chloromethyl-1H-benzimidazole (0.19 mmol) and the contents were stirred at 100° C. overnight. The solid inorganic material was removed by filtration and the solvent was removed in vacuo. The product was isolated by prep thin layer chromatography over silica gel eluting with 5% methanol in dichloromethane to get 0.02 g of the product 67A as off-white solid. Calcd m/z for C$_{31}$H$_{31}$Cl$_2$N$_5$H$^+$=544.2. Found m/z=544.1.

The following compounds were prepared in analogous fashion:

| Cpd. # | Structure | Formula (M + 1)+ | calcd m/z | obsd m/z |
|---|---|---|---|---|
| 67A | 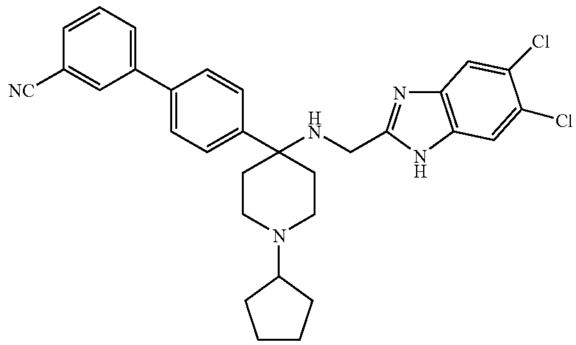 | $C_{31}H_{31}Cl_2N_5H^+$ | 544.2 | 544.1 |
| 67B* | 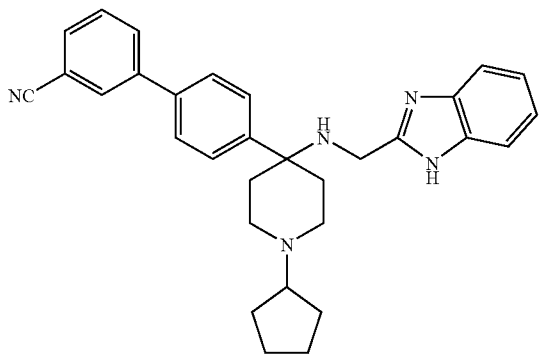 | $C_{31}H_{33}N_5H^+$ | 476.3 | 476.3 |

*Compound 67B was prepared by alkylation of the 4-bromo-phenyl analog followed by Suzuki (procedure K) to introduce the m-CN phenyl group.

Preparation of Carbon-Linked Homologated Piperidines 75:

Step 1:

Nitrile 68 was prepared using procedure O as follows:

Sodium ethoxide (15.27 g, 0.224 moles) was added in portions to a stirring solution of 40.0 g of 4-bromophenyl acetonitrile (0.204 moles) in 350 mL of ethanol at room temperature. After the addition was complete, the reaction was stirred for 1 h at room temperature. A solution of 34.75 g of 1-benzyl-4-piperidone (0.184 mole) in 50 mL of ethanol was added via an addition funnel. The reaction was heated in an oil bath at 80-85° C. for 17 h. The reaction was concentrated to ~100 mL and was poured into 850 mL of ice water with stirring. The mixture was made strongly acidic (pH 1-2) with the portion-wise addition of conc. HCl. The aqueous phase was stirred for 30 min. and was made basic (pH~10) with the addition of 30% NaOH. The aqueous phase was extracted with three 400 mL portions of dichloromethane. The combined organic extracts were dried over anhydrous magnesium sulfate and evaporated to give 70.66 g a thick oil. The residue was purified by flash column chromatography on silica gel eluting with a solvent gradient from 15-30% ethyl acetate in hexanes to give 30.0 g of 68 as a solid: ES MS Calcd m/z for $C_{20}H_{19}BrN_2H^+=367/369$. Found m/z=367/369.

Step 2: The unsaturated nitrile of compound 68 was reduced using procedure AC as exampled below:

The 1M DIBAL in toluene (34.20 mL, 0.0342 moles) was added dropwise to a stirring solution of 10.46 g of compound 68 (0.0285 moles) in 100 mL of dichloromethane at −78° C. The reaction was stirred at −78° C. for an additional 45 min.

The reaction was quenched with the addition of ~12 g of sodium decahydrate in portions. The mixture was allowed to warm to room temperature, diluted with ethyl acetate, and filtered through a layer of Celite. The filter pad was washed with additional ethyl acetate. The combined organic filtrate was evaporated to give 10.64 g of an oil. The material was purified by flash column chromatography on silica gel eluting with a gradient from 5-30% ethyl acetate in hexane to give 5.06 g of the product 69 as an oil. ES MS Calcd m/z for $C_{20}H_{21}BrN_2 H^+=369/371$. Found m/z=369/371.

Step 3: Reduction of nitrile 69 to aldehyde 70 was performed according to procedure AD as exampled below:

The 1M DIBAL in toluene (20.35 mL, 0.0203 moles) was added dropwise to a stirring solution of 5.00 g of compound 69 (0.0135 moles) in 40 mL of dichloromethane at −50 to −60° C. The acetone/dry ice bath was allowed to warm to room temperature over 16 h. The reaction was cooled to 0° C. and ~40 mL of 1N aqueous HCl was added dropwise followed by the addition of 30 mL of water. The mixture was stirred at room temperature for ~40 min. The reaction was made basic with the addition of solid sodium bicarbonate. The aluminum salts were removed by filtration through a layer of Celite. The filter pad was washed with dichloromethane. The layers were partitioned and separated. The aqueous phase was extracted with two 200 mL portions of dichloromethane. The combined organic extracts were dried over anhydrous sodium sulfate and evaporated to give 4.96 g of aldehyde 70 as an oil: ES MS Calcd m/z for $C_{20}H_{22}BrNO$ $H^+=372/374$. Found m/z=372/374.

Step 4: Homologation of aldehyde 70 to give unsaturated ester 71 was accomplished using procedure AE as exampled below;

To a mixture of 0.452 g of NaH (60% NaH in oil, 18.82 mmol) in 110 mL of tetrahydrofuran was cooled to 0° C. was added 2.48 g of trimethyl phosphonoacetate (17.1 mmol) drop-wise. A thick suspension was obtained during the addition. The reaction was stirred an additional 2.5 h. A solution of 4.90 g of 70 (13.2 mmol) in 25 mL of tetrahydrofuran was added dropwise over 30 min. The reaction was stirred at 0° C. for 15 min. and then at room temperature for 5 h. The reaction was concentrated in vacuo and the residue was partitioned between 75 mL of water and 200 mL of ethyl acetate. The layers were separated and the water was extracted with two 100 mL portions of ethyl acetate. The combined ethyl acetate extracts washed with 100 mL of brine, dried over anhydrous sodium sulfate and evaporated to yield 6.04 g of an oil. This material was purified by flash column chromatography on silica gel eluting with a solvent gradient from 20-35% ethyl acetate in hexane to give 3.61 g of unsaturated ester 71 as an oil: ES MS Calcd m/z for $C_{23}H_{26}BrNO_2$ $H^+=428/430$. Found m/z=428/430.

Step 5: Reduction of unsaturated olefin 71 to give ester 72 was accomplished using procedure AF as exampled below:

A solution of 6.27 g of compound 71 (0.0146 moles) in 150 mL of ethanol was stirred with 0.627 g of 5% Rh on alumina under an 1 atmosphere of hydrogen at room temperature. After 1.5 h, the reduction was shown to be complete by tlc analysis (30% ethyl acetate in hexane) and mass spectroscopy. The catalyst was removed by filtration through a layer of Celite. The filter pad was washed with ethanol and the combined ethanol filtrate was evaporated to give 6.20 g of saturated ester 72 as an oil: ES MS Calcd m/z for $C_{23}H_{28}BrNO_2$ $H^+=430/432$. Found m/z=430/432.

Step 6: Reduction of ester 72 to give aldehyde 73 was accomplished using procedure AG as exampled below:

To a solution of 6.15 g of ester 72 (14.3 mmol) in 70 mL of toluene at −78° C. was added 19.80 mL of 1M DIBAL in toluene (19.7 mmol) dropwise over 40 min. The reaction vas stirred at −78° C. for 1.5 h. While maintaining the reaction at −78° C., the reaction was quenched by the addition of ~9 g of sodium sulfate decahydrate in portions. The mixture was stirred at −78° C. for 20 min. and then at room temperature for 40 min. The solids were removed by filtration through a layer of Celite. The filter pad was washed with ethyl acetate. The combined organic filtrate was concentrated to give 5.87 g of an oil. Purification by flash column chromatography on silica gel eluting with a solvent gradient from 35-50% ethyl acetate in hexane gave 3.35 g of aldehyde 73 as an oil: ES MS Calcd m/z for $C_{22}H_{26}BrNO$ $H^+=400/402$. Found m/z=400/402.

Step 7: Benzimidazole formation was accomplished to give compound 74 as exampled in procedure AH below:

A mixture of 0.258 g of aldehyde 73 (0.644 mmol), 0.114 g of 4,5-dichloro-1,2-phenylenediamine (0.644 mmol), and 0.159 g of sodium metabisulfite (0.838 mmol) in 5.5 mL of dimethylacetamide were heated in an oil bath at 100-105° C. for 4 h. The reaction was cooled and poured into 60 mL of water with stirring. The solid thus formed was collected by vacuum filtration and was washed with water. It was fully dried under vacuum to 0.279 g of a powder. The product was purified by flash column chromatography on silica gel eluting with a solvent gradient from 2-5% methanol in dichloromethane containing 0.5% ammonium hydroxide to give 0.118 g of benzimidazole 74A as a solid: ES MS Calcd m/z for $C_{28}H_{28}BrCl_2N_3$ $H^+=556/558$. Found m/z=556/558.

The following compounds were prepared in analogous fashion:

| Cpd. # | Structure | Formula (M + 1)$^+$ | calcd m/z | obsd m/z |
|---|---|---|---|---|
| 74A | 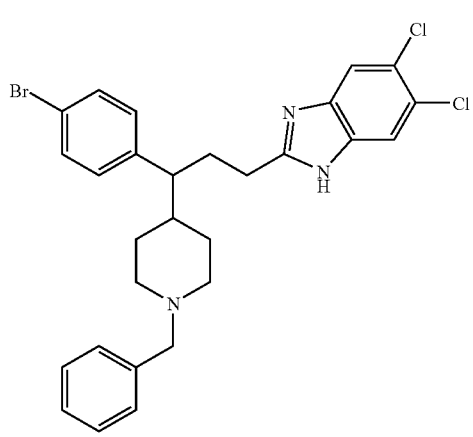 | $C_{28}H_{28}BrCl_2N_3H^+$ | 556/558 | 556/558 |

-continued

| Cpd. # | Structure | Formula (M + 1)+ | calcd m/z | obsd m/z |
|---|---|---|---|---|
| 74B | 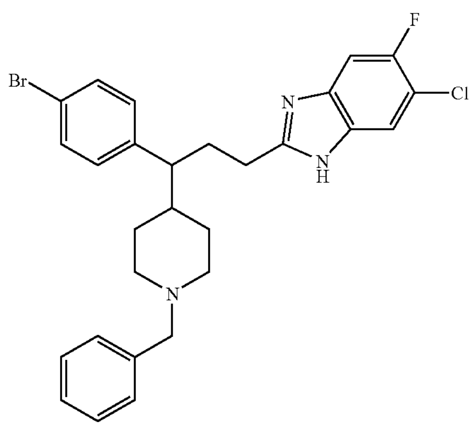 | C$_{28}$H$_{28}$BrCl$_2$N$_3$H$^+$ | 540/542 | 540/542 |

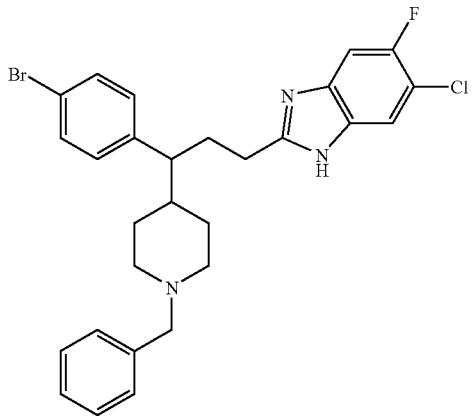

| | | | | |
|---|---|---|---|---|
| 74C | | C$_{28}$H$_{28}$BrCl$_2$N$_3$H$^+$ | 556/558 | 556/558 |

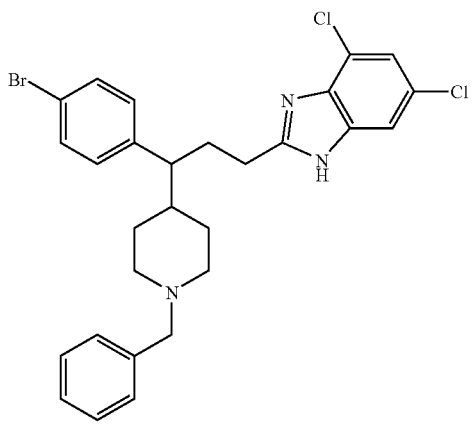

Step 8: Arylation of compound 74A to give compound 75A was accomplished using procedure G as exampled below:

A mixture of 0.118 g of 74A (0.212 mmol), 0.041 g of 3-cyanophenyl boronic acid (0.276 mmol), 0.029 g of tetrakis (triphenylphosphine) palladium (0.025 mmol), and 0.3 mL of 2N aqueous sodium carbonate in 2 mL of toluene and 2 mL of methanol was degassed with argon. The reaction was heated at 120° C. under microwave conditions for 10 min using temperature control. The reaction was diluted with methanol, stirred and filtered through a layer of Celite. The filter pad was washed with methanol. The combined filtrate was evaporated to give 0.219 g of a solid. This residue was purified by flash column chromatography on silica gel eluting with a solvent gradient from 2%-5% methanol in dichloromethane to give 0.075 g of compound 75A as a solid: ES MS Calcd m/z for C$_{35}$H$_{32}$Cl$_2$N$_4$ H$^+$=579/581. Found m/z=579/581.

The following compounds were prepared in analogous fashion:

| Cpd. # | Structure | Formula (M + 1)+ | calcd m/z | obsd m/z |
|---|---|---|---|---|
| 75A | 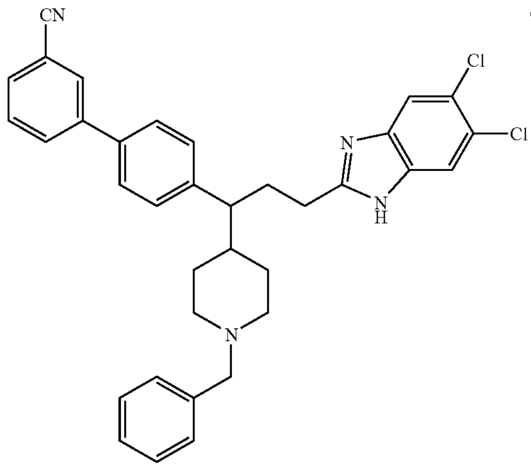 | $C_{35}H_{32}Cl_2N_4H^+$ | 579/581 | 579/581 |
| 75B | 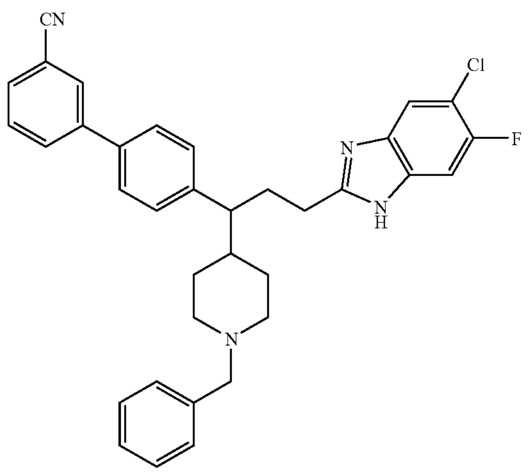 | $C_{35}H_{32}FClN_4H^+$ | 563/565 | 563/565 |
| 75C | 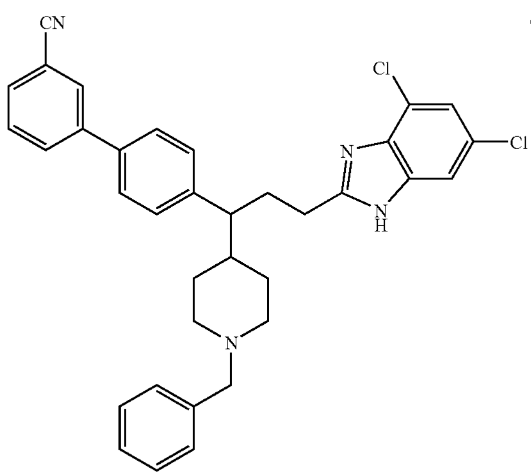 | $C_{35}H_{32}Cl_2N_4H^+$ | 579/581 | 579/581 |

MCH Receptor Binding Assay:

Membranes from CHO cells expressing the MCH receptor were prepared by lysing cells with 5 mM HEPES for 15 min at 4C. Cell lysates were centrifuged (12.5000×g, 15 min) and the pellet was resuspended in 5 mM HEPES. For each 96-well plate (Microlite, Dynex Technologies), 1 mg of cell membranes were incubated with 10 mg of wheat germ agglutinin SPA beads (Amersham) for 5 min at 4 C in a volume of 10 ml of binding buffer (25 mM HEPES, 10 mM MGCl$_2$, 10 mM NaCl, 5 mM MnCl$_2$, 0.1% BSA). The membrane/bead mixture was centrifuged (1500×g, 3.5 min), the supernatant was aspirated, and the pellet was resuspended in 10 ml binding buffer. The centrifugation, aspiration and resuspension were then repeated. The membrane/bead mixture (100 μl) was then added to 96-well plates containing 50 μl of 500 pM [$^{125}$I]-MCH (NEN) and 50 ml of the appropriate concentration of compound (4× the desired final concentration). Nonspecific binding was determined by including 1 μM MCH in the binding reaction. The binding reaction was incubated at room temperature for 2 h. Plates were then analyzed in a TOP-COUNT microplate scintillation counter (Packard). Data was analyzed and Ki values were determined using GraphPad Prism.

Compounds with Ki values greater than 100 nM are designated in the table below as D class compounds.

Compounds with Ki values between 50 and 100 nM are designated in the table below as C class compounds.

Compounds with Ki values between 20 and 50 nM are designated in the table below as B class compounds.

Compounds with Ki values less than 20 nM are designated in the table below as A class compounds.

In a preferred embodiment of the invention, Example 28A, a Ki value of 3 nM was observed.

| Cpd. # | Structure | Class |
|---|---|---|
| 8A | 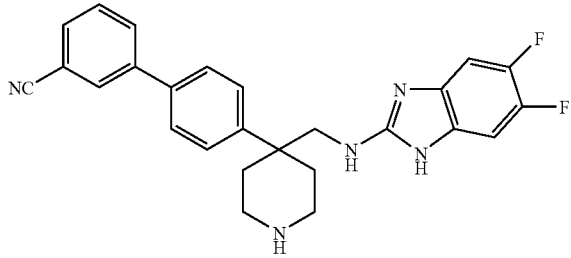 | B |
| 8B | 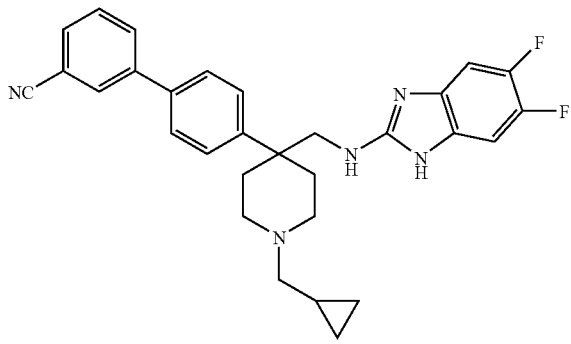 | B |
| 8C | 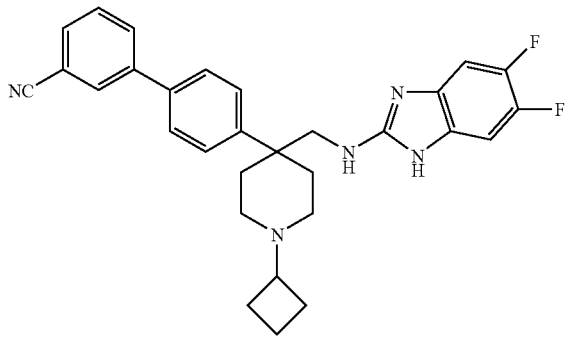 | B |

| Cpd. # | Structure | Class |
|---|---|---|
| 8D | 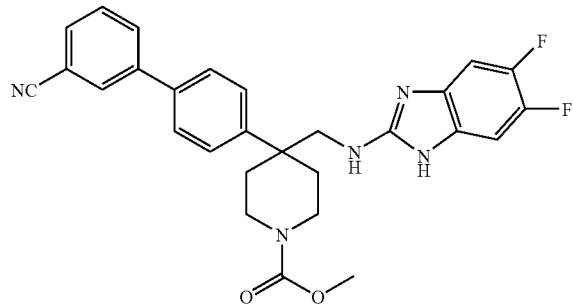 | D |
| 11A | 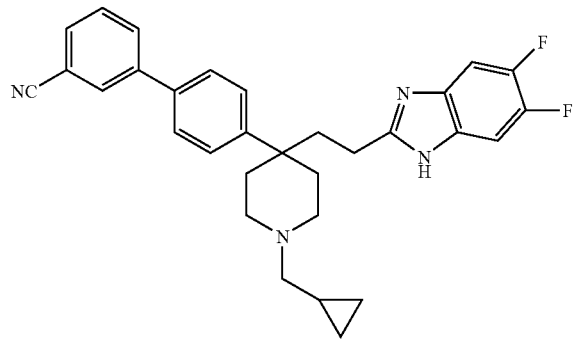 | D |
| 11B | 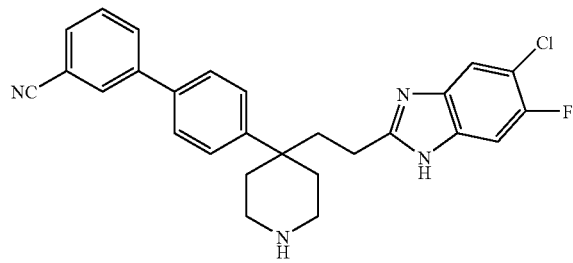 | D |
| 11C | 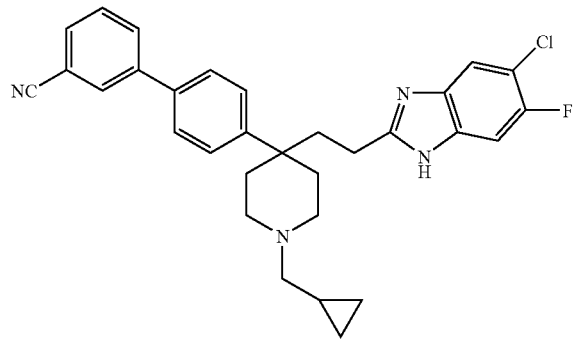 | D |

-continued
| Cpd. # | Structure | Class |
|---|---|---|
| 15A | 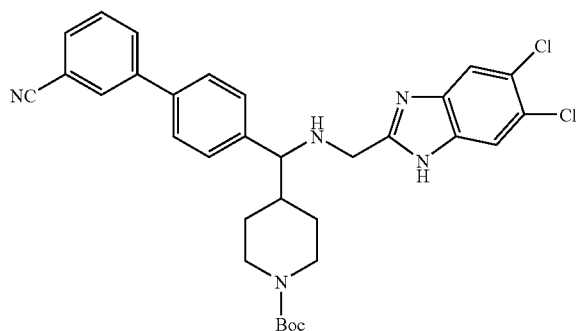 | C |
| 15B | 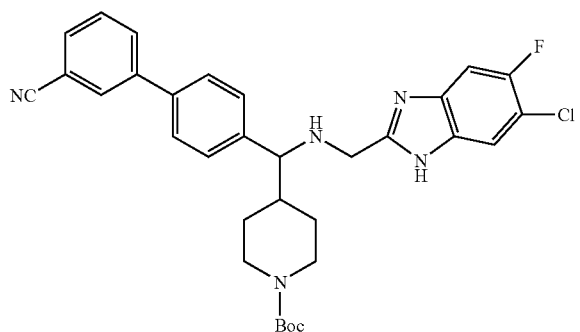 | B |
| 16A | 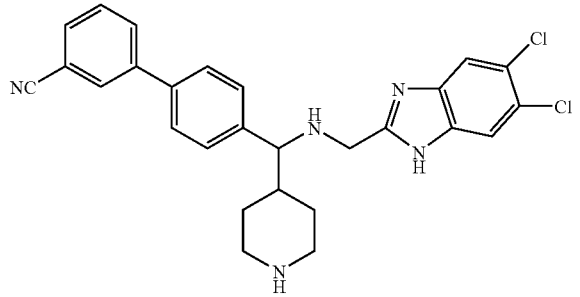 | A |
| 16B | 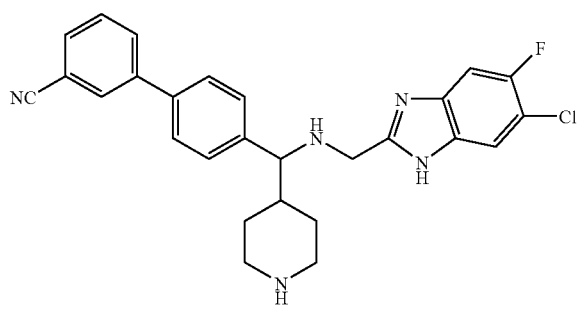 | B |

-continued
| Cpd. # | Structure | Class |
|---|---|---|
| 17A | 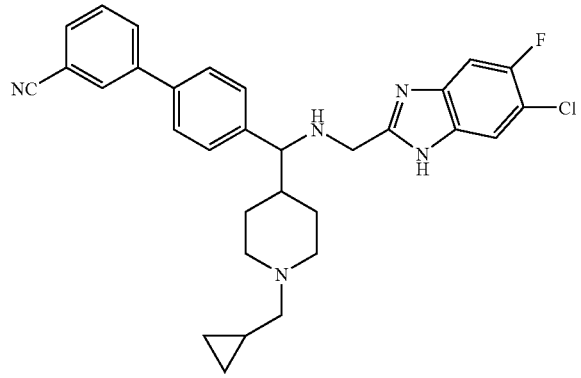 | A |
| 17B | 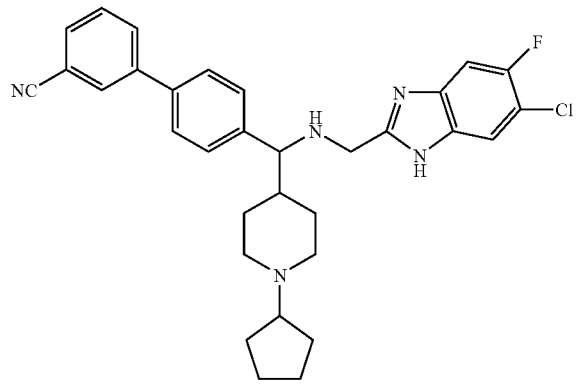 | B |
| 28A | 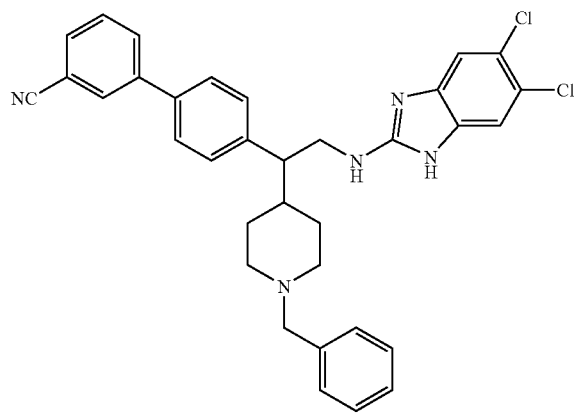 | A |

-continued
| Cpd. # | Structure | Class |
|---|---|---|
| 28B | 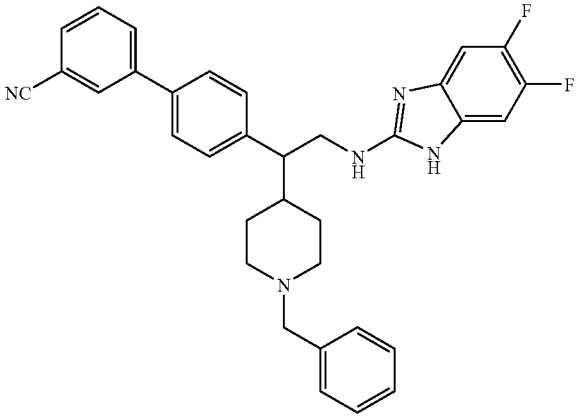 | A |
| 33 | 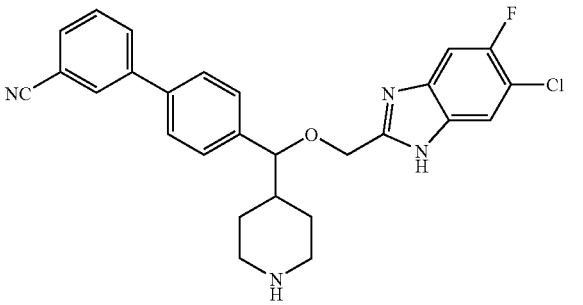 | B |
| 34D | 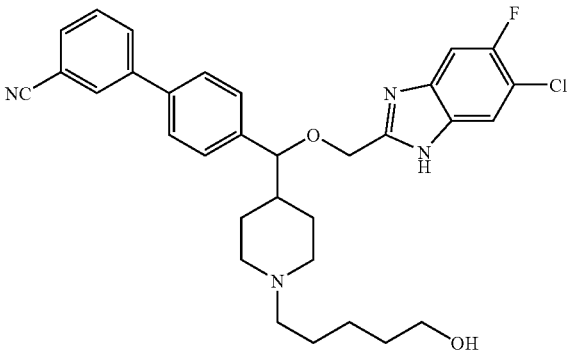 | D |
| 34A | 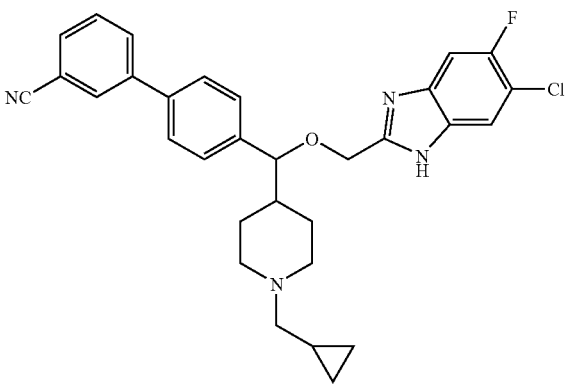 | B |

-continued
| Cpd. # | Structure | Class |
|---|---|---|
| 34B | 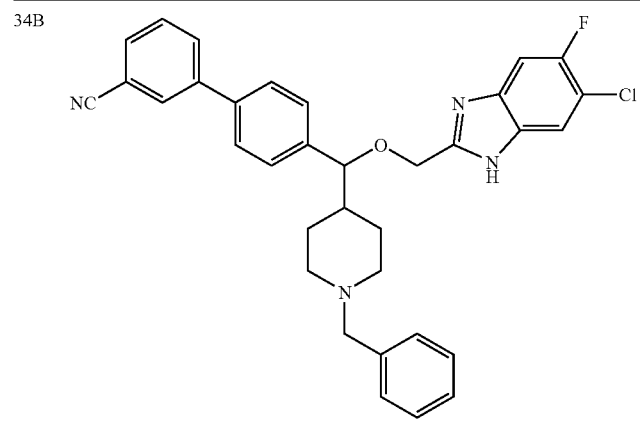 | B |
| 34C | 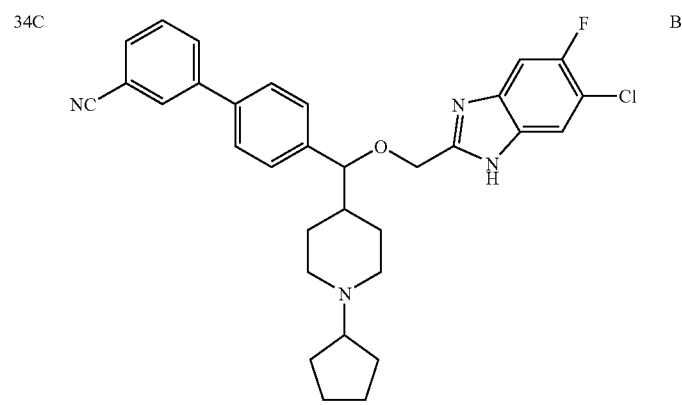 | B |
| 39 | 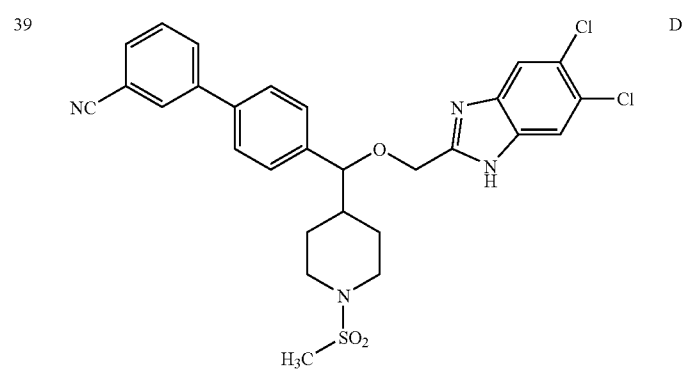 | D |
| 44 | 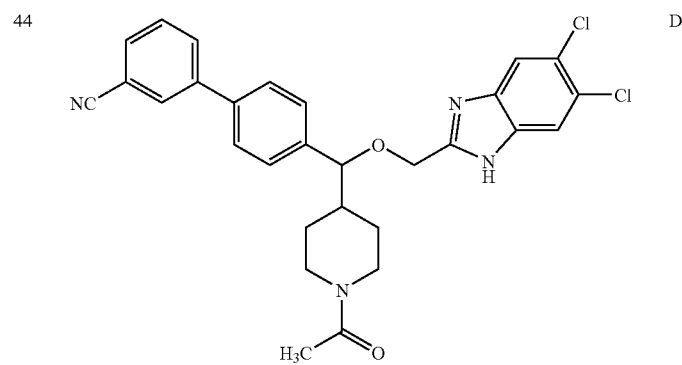 | D |

-continued

| Cpd. # | Structure | Class |
|---|---|---|
| 48 | 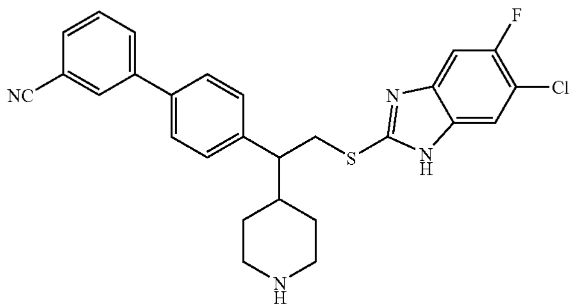 | D |
| 53 | 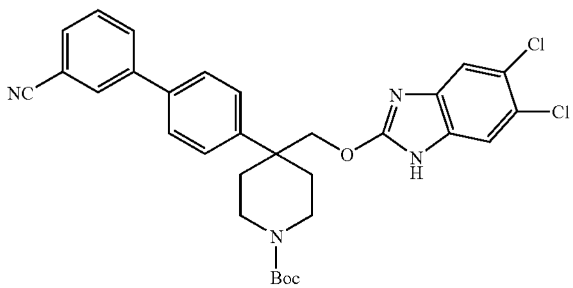 | D |
| 54 | 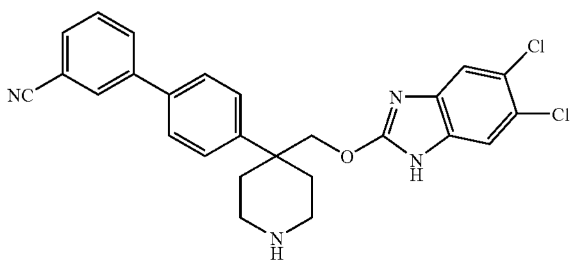 | C |
| 56 | 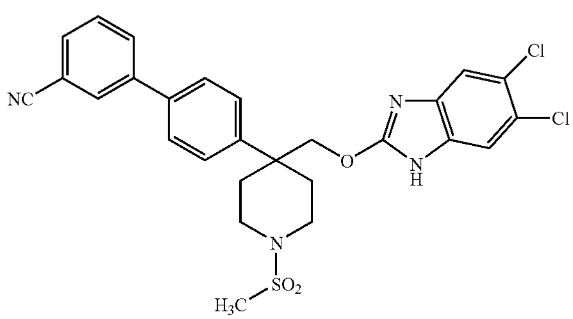 | D |
| 57 | 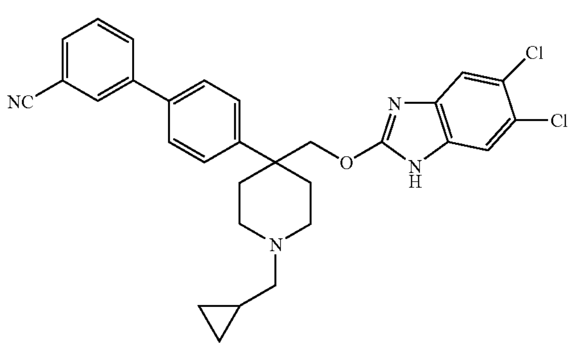 | C |

-continued
| Cpd. # | Structure | Class |
|---|---|---|
| 58 | 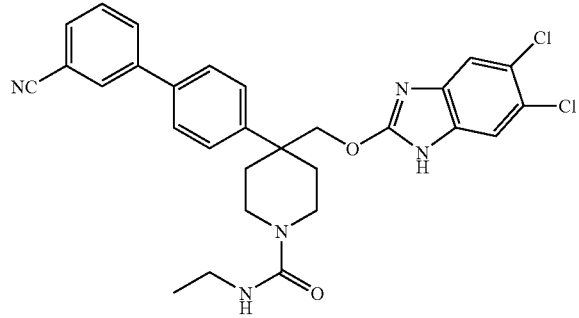 | D |
| 63 | 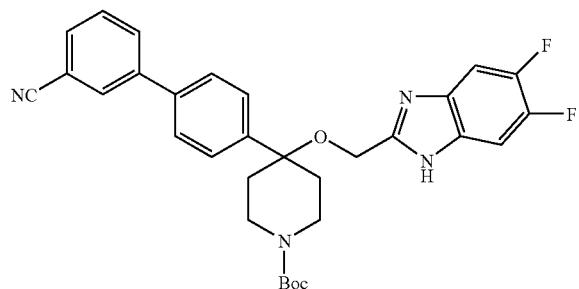 | D |
| 64 | 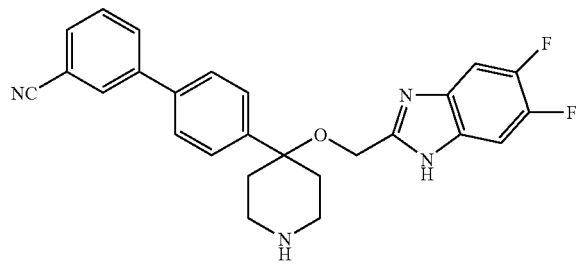 | D |
| 67A | 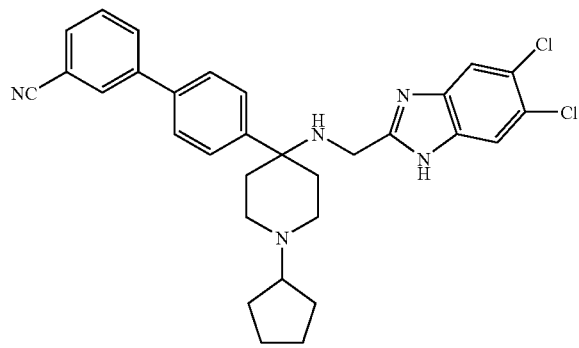 | D |

-continued
| Cpd. # | Structure | Class |
|---|---|---|
| 67B | 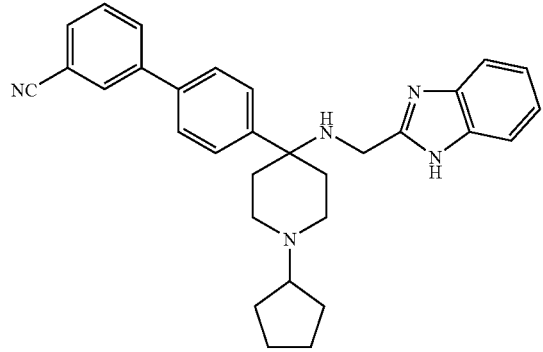 | D |
| 75A | 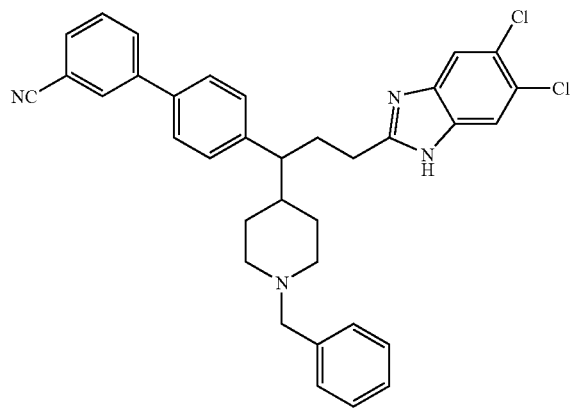 | C |
| 75B | 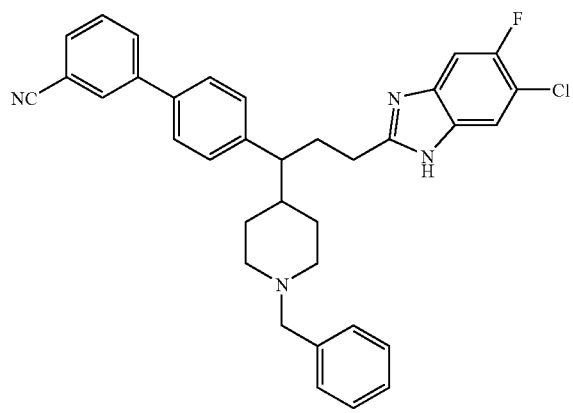 | B |

-continued

| Cpd. # | Structure | Class |
|---|---|---|
| 75C | 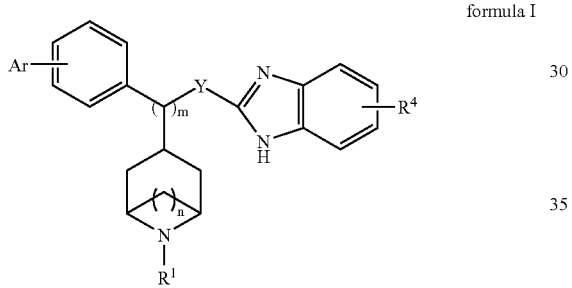 | B |

What is claimed is:

1. A compound represented by the structural formula formula I

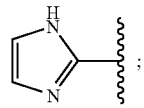

or a pharmaceutically acceptable salt or solvate thereof, wherein

Y is a bond, —$(CR^2R^3)_pNR^8(CH_2)_q$—, —$(CR^2R^3)_t$ $(CHR^{12})$—, —$(CHR^{12})_t(CR^2R^3)$—, —$CHR^{12}CH_2N$—, —$CHR^{12}CH_2S$—, —$CHR^{12}CH_2O$—, —$C(O)(CR^2R^3)_pNR^8$—, —$(CH_2)_pO(CH_2)_q$—, —$(CH_2)_pS(CH_2)_q$—, —$(CR^2R^3)_t$—, —$C(O)(CH_2)_rO$— or —$C(O)(CH_2)_rS$—;

m is 1;
n is 0, 2 or 3;
p is 0 to 4;
q is 0 to 4;
r is 1 to 3;
t is 1 to 6;

Ar is aryl, heteroaryl, $R^6$-substituted aryl or $R^6$-substituted heteroaryl;

$R^1$ is hydrogen, alkyl, cycloalkyl, cycloalkylalkyl-, aralkyl, hydroxyalkyl, —$C(O)R^5$, —$C(O)OR^5$, —$C(O)NR^8R^9$, —$S(O_2)R^5$, —$S(O_2)NR^8R^9$, aryl, —$CF_3$, $R^{10}$-substituted aralkyl, $R^{10}$-substituted aryl, $R^{10}$-substituted alkyl, $R^{10}$-substituted cycloalkyl- or $R^{10}$-substituted cycloalkylalkyl-;

$R^2$ and $R^3$ can be the same or different, each being independently hydrogen or alkyl; or $R^2$ and $R^3$ can be joined together and with the carbon to which they are attached form a 3 to 7-membered ring;

$R^4$ is 1 to 4 substituents, each $R^4$ is independently selected from the group consisting of hydrogen, —OH, alkoxy, —$OCF_3$, —CN, alkyl, halogen, —$NR^8C(O)R^7$, —$C(O)NR^8R^9$, —$NR^8S(O_2)R^7$, —$S(O_2)NR^8R^9$, —$S(O_2)R^7$, —$C(O)R^7$, —$C(O)OR^8$, —$CF_3$, -(alkylene)$NR^8R^9$, -(alkylene)$NR^8C(O)R^7$, CHO, —C=$NOR^8$ or two adjacent $R^4$ groups can be joined together to form a methylene dioxy or ethylene dioxy group;

$R^5$ is alkyl, aryl, aralkyl, cycloalkyl, $R^{11}$-substituted cycloalkyl, or $R^{11}$-substituted aryl;

$R^6$ is 1 to 5 substituents, each $R^6$ is independently selected from the group consisting of hydrogen, —OH, alkoxy, —$OCH_3$, —CN, alkyl, halogen, —$NR^8R^9$, —$NR^8C(O)R^7$, —$C(O)NR^8R^9$, —$NR^8S(O_2)R^7$, —$S(O_2)NR^8R^9$, —$S(O_2)R^7$, —$C(O)R^7$, —$C(O)OR^8$, —$CF_3$, —(alkylene)$NR^8R^9$, —(alkylene)$C(O)NR^8R^9$, —(alkylene)$NR^8C(O)R^7$, -(alkylene)$NR^8S(O_2)R^7$, -(alkylene)$NR^8C(O)NR^8R^9$, —(alkylene)$NR^8C(O)OR^7$, CHO, —C=$NOR^8$ and $R^7$ is alkyl, aryl, aralkyl, or $R^{11}$-substituted aryl;
$R^8$ is hydrogen or alkyl;
$R^9$ is hydrogen, alkyl, aryl, aralkyl, or cycloalkyl;
$R^{10}$ is 1 to 5 substituents, each $R^{10}$ is independently selected from the group consisting of —OH, alkoxy, —$C(O)NR^8R^9$, —$NR^8R^9$, —$NR^8S(O_2)R^5$, —$NR^8C(O)NR^8R^9$, —$NR^8C(O)R^5$, —$NR^8C(O)OR^5$ and —$C(O)OR^9$;
$R^{11}$ is 1 to 5 substituents, each $R^{11}$ being independently selected from the group consisting of hydrogen, —OH, alkoxy, —$OCF_3$, —CN, alkyl, halogen or —$CF_3$; and
$R^{12}$ is hydroxy or alkoxy.

2. The compound of claim 1 wherein $R^1$ is hydrogen, alkyl, aralkyl, cycloalkyl, cycloalkylalkyl-, hydroxyalkyl, $R^{10}$-substituted alkyl, —$S(O_2)R^5$, —$C(O)R^5$, —$C(O)NR^8R^9$ or —$C(O)OR^5$.

3. The compound of claim 1 wherein

Ar is $R^6$-substituted aryl; and $R^6$ is 1 to 5 substituents and each $R^6$ is independently selected from the group consisting of halogen, —$CF_3$, —$OCF_3$, —CN, —CHO, —$S(O_2)R^5$, —$C(O)R^5$, —$C(O)NR^8R^9$, -(alkylene)$C(O)NR^8R^9$,-(alkylene)$NR^8R^9$, -(alkylene)$NR^8C(O)R^5$, -(alkylene)$NR^8S(O_2)R^5$ and

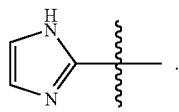

4. The compound of claim 3 wherein $R^6$ is 1 substituent, wherein said $R^6$ is independently selected from the group consisting of halogen, —CN, -(alkylene)$NR^8R^9$, -(alkylene)$C(O)NR^8R^9$, and -(alkylene)$NR^8C(O)R^5$.

5. The compound of claim 3 wherein Ar is $R^6$-substituted phenyl and $R^6$ is at the meta or para position of Ar, relative to the position where Ar is attached to the parent moiety.

6. The compound of claim 4 wherein $R^6$ is at the meta position of Ar, relative to the position where Ar is attached to the parent moiety.

7. The compound of claim 3 wherein $R^6$ is —CN.

8. The compound of claim 4 wherein $R^6$ is —CN.

9. The compound of claim 1 wherein $R^4$ is two substituents and each $R^4$ is independently selected from the group consisting of halogen, —CN and —$CF_3$.

10. The compound of claim 9 wherein $R^4$ is selected from the group consisting of Cl, F and —$CF_3$.

11. The compound of claim 2 wherein $R^1$ is hydrogen, Boc, methyl, ethyl, hydroxyethyl, hydroxypentyl, cyclobutyl, cyclopentyl,

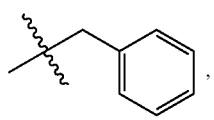

—$S(O_2)CH_3$, —$C(O)CH_3$, —$C(O)CH_2CH_3$, —$C(O)NHCH_2CH_3$, isopropyl or cyclopropylmethyl.

12. A compound selected from the group consisting of

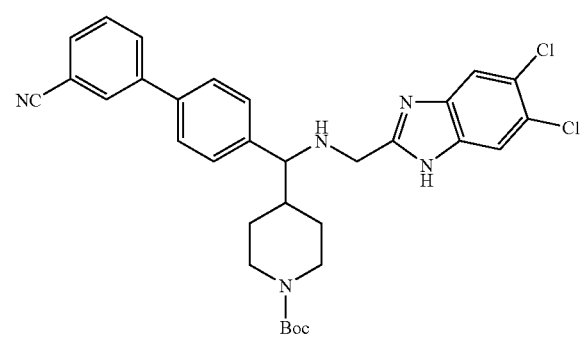

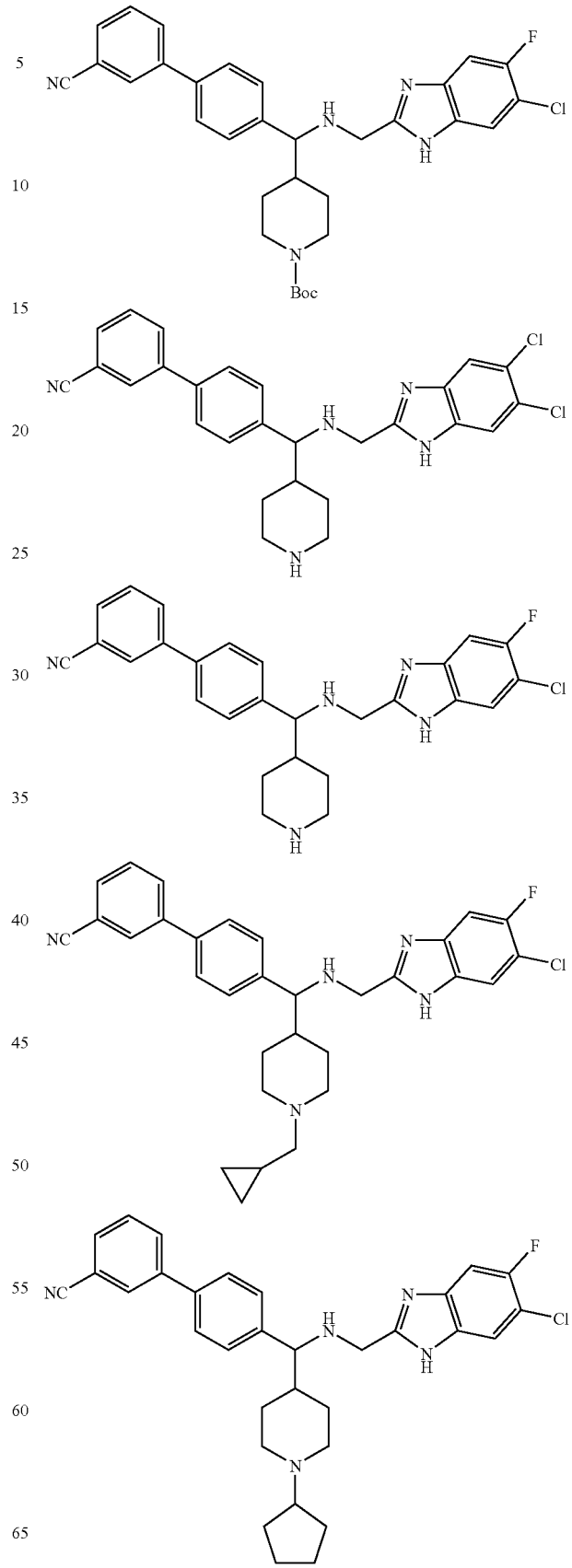

95
-continued
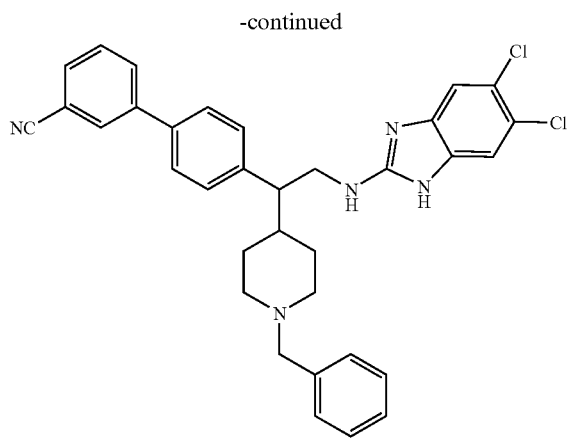
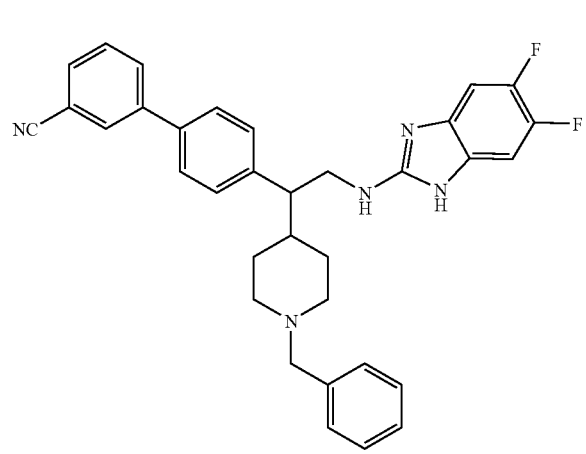
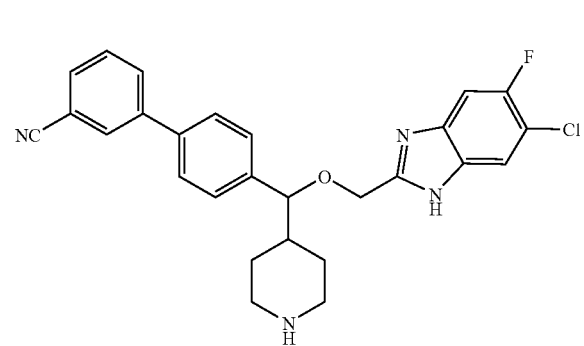
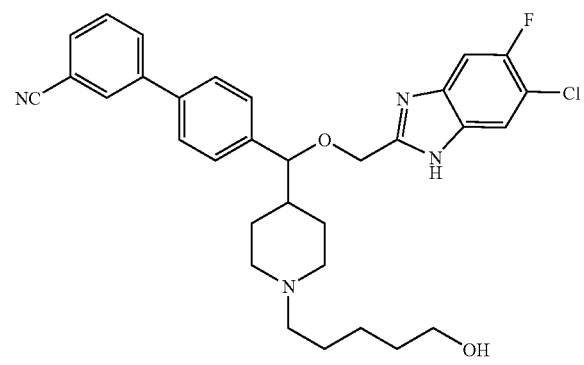
96
-continued
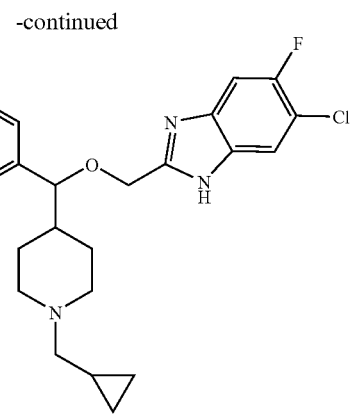
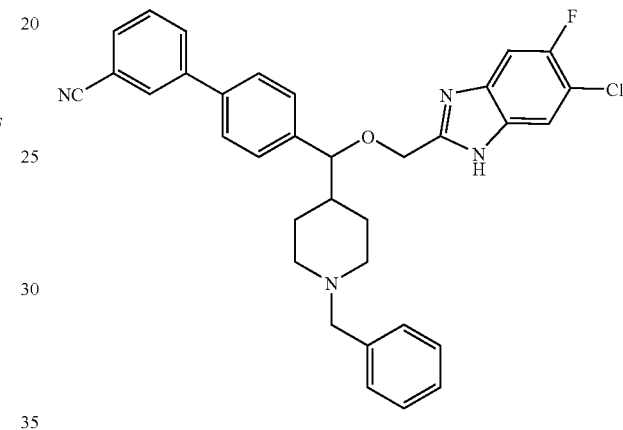
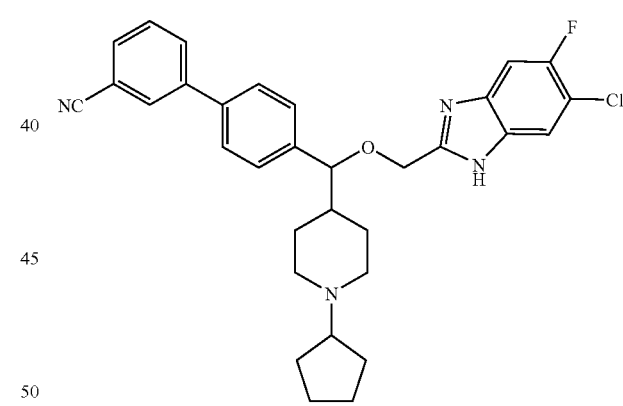
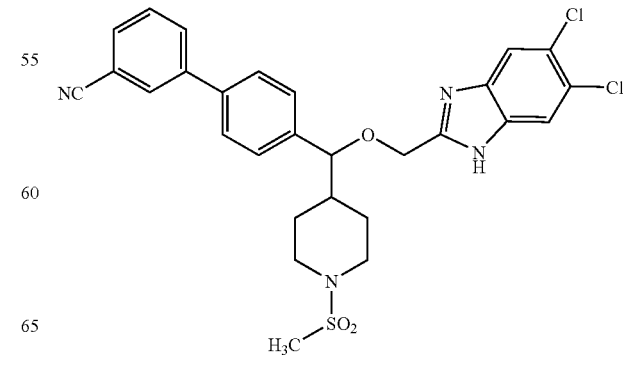

-continued
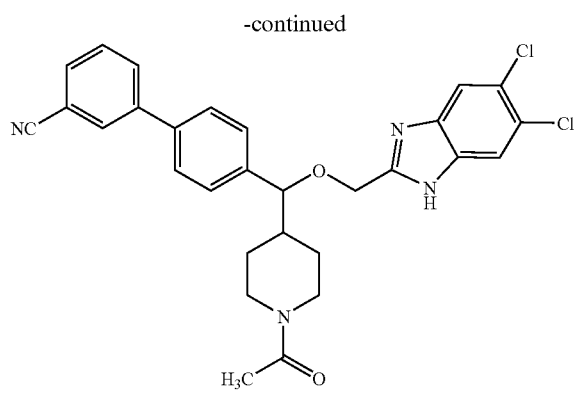
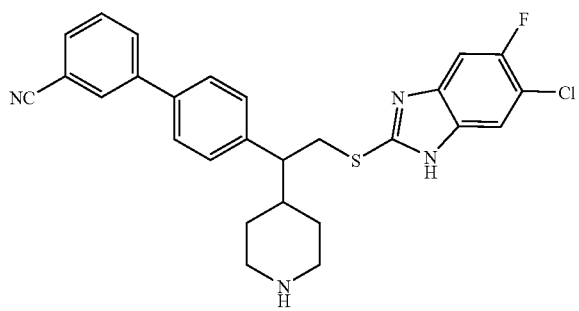
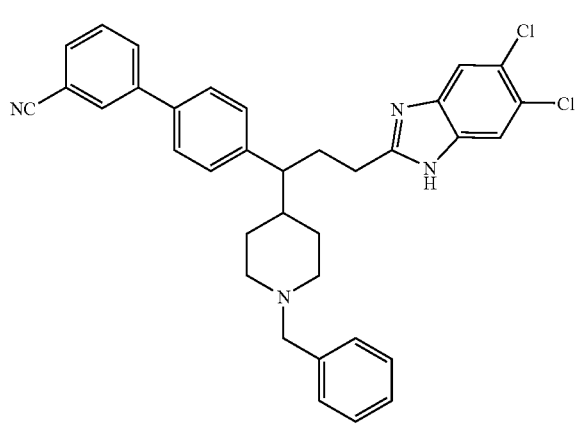
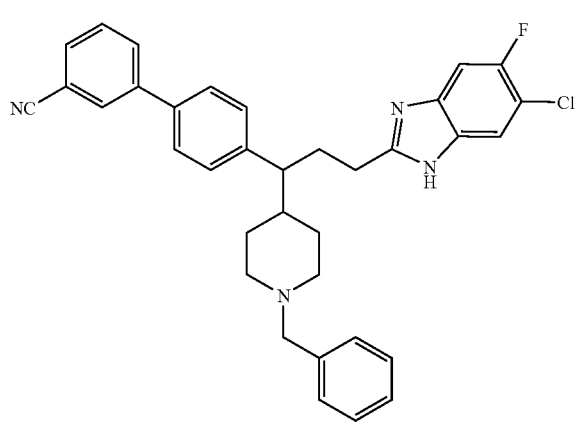
and
-continued
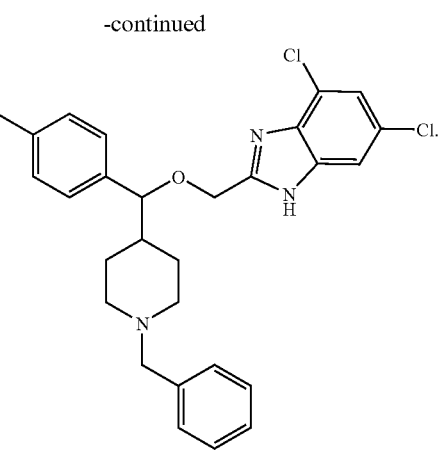
13. A compound of the formula:
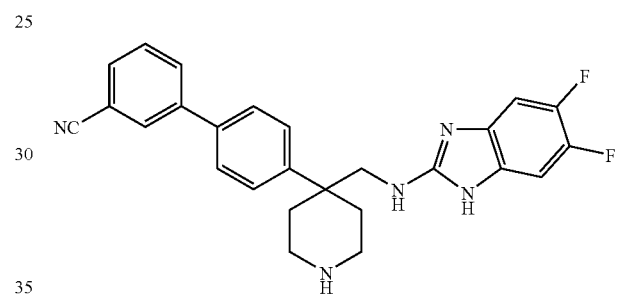
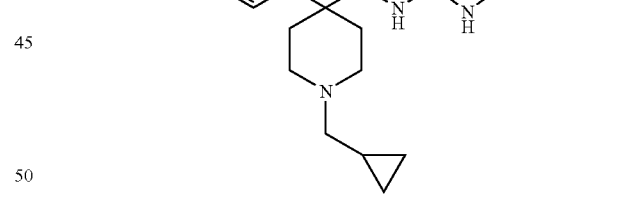

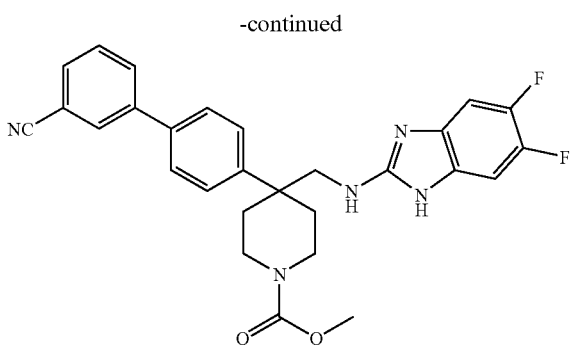
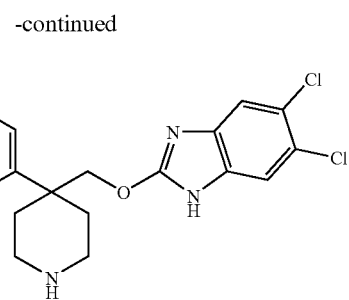
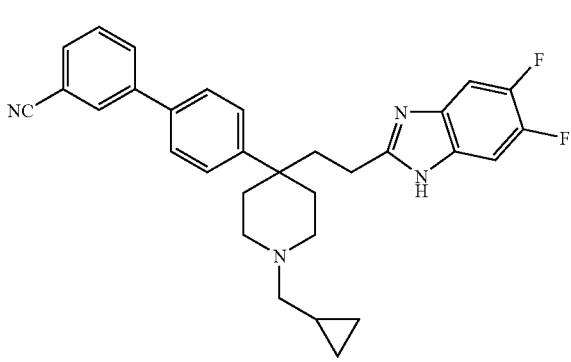
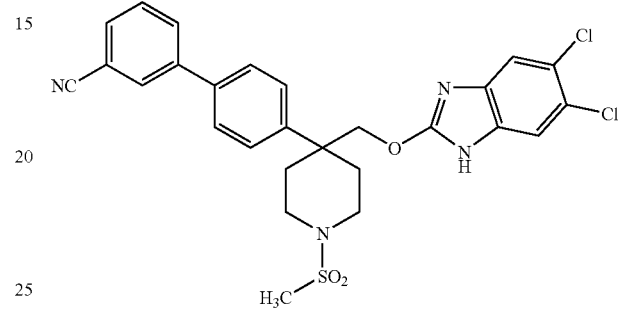
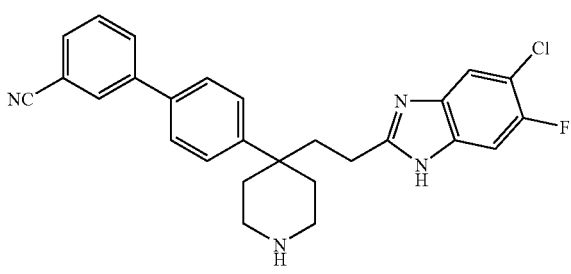
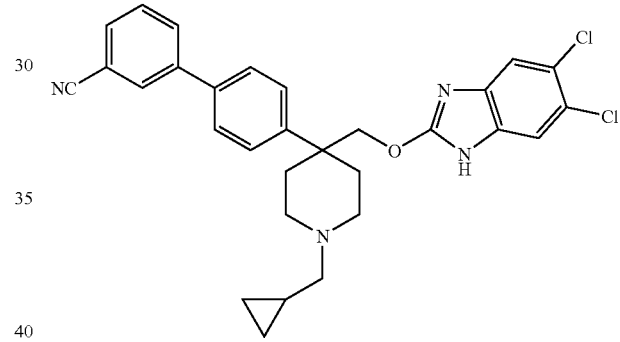
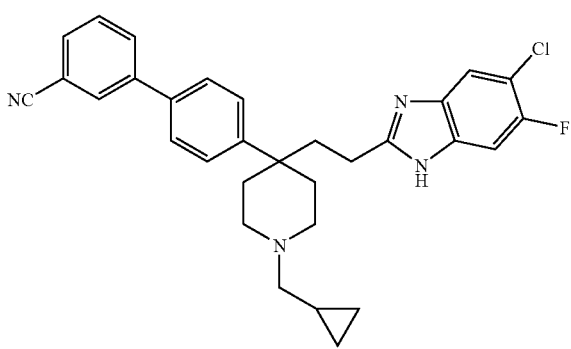
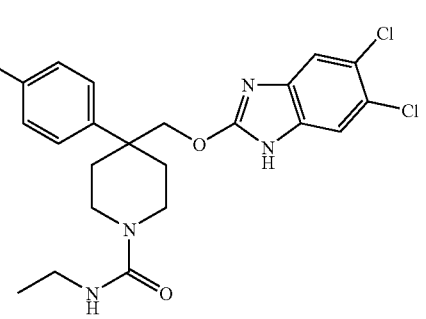
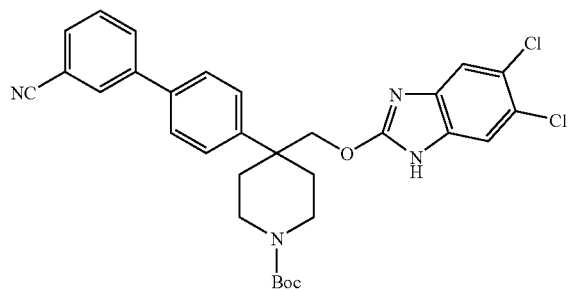
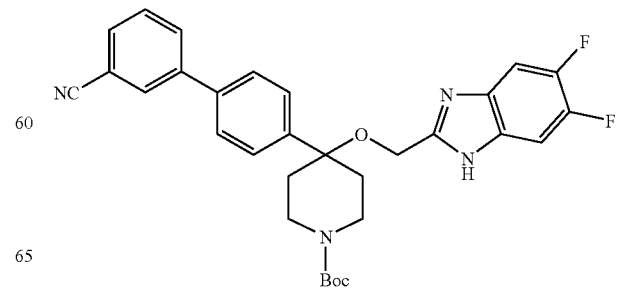

101
-continued
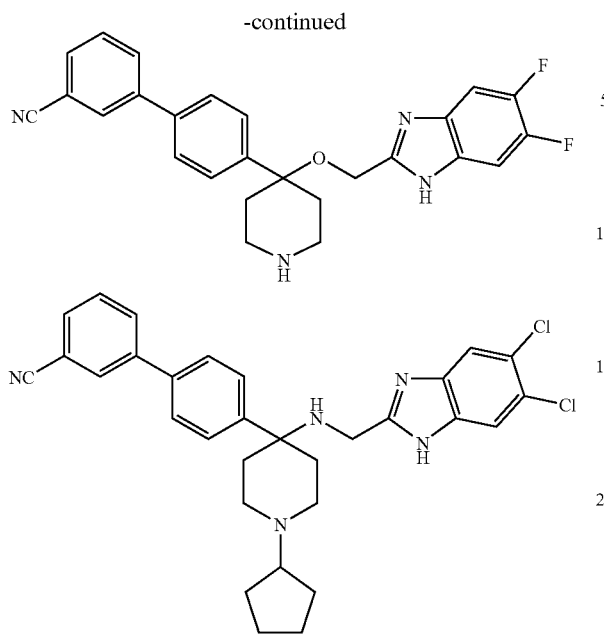
102
-continued
or
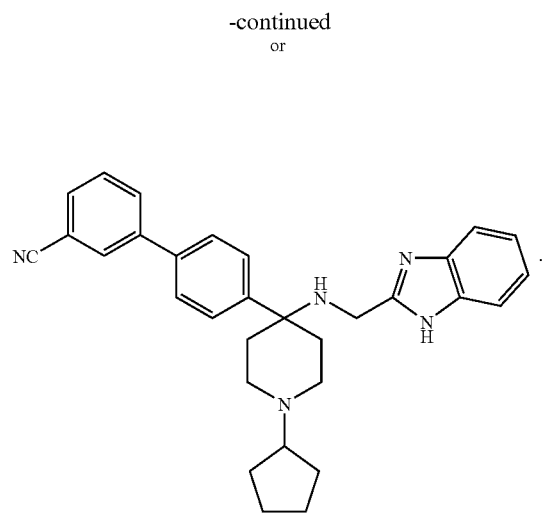
* * * * *

UNITED STATES PATENT AND TRADEMARK OFFICE
CERTIFICATE OF CORRECTION

| | | |
|---|---|---|
| PATENT NO. | : 7,511,146 B2 | Page 1 of 1 |
| APPLICATION NO. | : 10/926557 | |
| DATED | : March 21, 2009 | |
| INVENTOR(S) | : Duane A. Burnett et al. | |

It is certified that error appears in the above-identified patent and that said Letters Patent is hereby corrected as shown below:

In the Claims:

Claim 1, col. 92, line 36: Please correct "-OCH$_3$" to -- -OCF$_3$--.

Signed and Sealed this

Nineteenth Day of January, 2010

David J. Kappos
*Director of the United States Patent and Trademark Office*